US009655991B2

(12) United States Patent
Gousse et al.

(10) Patent No.: US 9,655,991 B2
(45) Date of Patent: May 23, 2017

(54) STABLE HYDROGEL COMPOSITIONS INCLUDING ADDITIVES

(71) Applicant: Allergan Industries, S.A.S., Pringy (FR)

(72) Inventors: Cecile Gousse, Dingy Saint Clair (FR); Pierre F. Lebreton, Annecy (FR); Nicolas Prost, Mornant (FR); Sumit Paliwal, Goleta, CA (US); Dennis Van Epps, Goleta, CA (US)

(73) Assignee: Allergan Industrie, S.A.S., Pringy (FR)

( * ) Notice: Subject to any disclaimer, the term of this patent is extended or adjusted under 35 U.S.C. 154(b) by 0 days.

(21) Appl. No.: 14/797,585

(22) Filed: Jul. 13, 2015

(65) Prior Publication Data

US 2015/0314040 A1  Nov. 5, 2015

Related U.S. Application Data

(63) Continuation of application No. 13/350,518, filed on Jan. 13, 2012, now Pat. No. 9,114,188, which is a continuation-in-part of application No. 13/005,860, filed on Jan. 13, 2011, now abandoned, which is a continuation-in-part of application No. 12/956,542, filed on Nov. 30, 2010, now abandoned, which is a continuation-in-part of application No. 12/714,377, filed on Feb. 26, 2010, now abandoned, which is a continuation-in-part of application No. 12/687,048, filed on Jan. 13, 2010, now abandoned.

(51) Int. Cl.
*A61L 27/20* (2006.01)
*A61L 27/52* (2006.01)
*A61L 27/54* (2006.01)

(52) U.S. Cl.
CPC ............... *A61L 27/20* (2013.01); *A61L 27/52* (2013.01); *A61L 27/54* (2013.01); *A61L 2300/204* (2013.01); *A61L 2300/216* (2013.01); *A61L 2300/40* (2013.01); *A61L 2300/402* (2013.01); *A61L 2300/418* (2013.01); *A61L 2300/428* (2013.01); *A61L 2300/802* (2013.01); *A61L 2400/06* (2013.01); *A61L 2430/34* (2013.01)

(58) Field of Classification Search
CPC .......... A61L 27/20; A61L 27/52; A61L 27/54; A61L 2400/06; A61L 2430/34
See application file for complete search history.

(56) References Cited

U.S. PATENT DOCUMENTS

| 2,128,827 A | 8/1938 | Killian |
| 3,548,056 A | 12/1970 | Eigen |
| 3,763,009 A | 10/1973 | Suzuki et al. |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs et al. |
| 4,642,117 A | 2/1987 | Nguyen et al. |
| 4,713,448 A | 12/1987 | Balazs et al. |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,084,563 A | 1/1992 | Sakai et al. |
| 5,087,446 A | 2/1992 | Suzuki et al. |
| 5,091,171 A | 2/1992 | Yu et al. |
| 5,137,723 A | 8/1992 | Yamamoto et al. |
| 5,143,724 A | 9/1992 | Leshchiner |
| 5,246,698 A | 9/1993 | Leshchiner et al. |
| 5,252,722 A | 10/1993 | Mandai et al. |
| 5,272,136 A | 12/1993 | Mandai et al. |
| 5,278,059 A | 1/1994 | Sugimoto et al. |
| 5,314,874 A | 5/1994 | Miyata et al. |
| 5,328,955 A | 7/1994 | Rhee et al. |

(Continued)

FOREIGN PATENT DOCUMENTS

CA        0949965        6/1974
CH   WO 2004073759 A1 *  9/2004  ............. A61L 27/20

(Continued)

OTHER PUBLICATIONS

Wahl, "European evaluation of a new hyaluronic acid filler incorporating lidocaine", 2008, Journal of Cosmetic Dermatology, vol. 7, pp. 298-303.*
Millay et al., "Vasoconstrictors in Facial Plastic Surgery", Feb. 1991, Arch. Otolaryngol. Head Neck Surg., vol. 117, pp. 160-163.*
Gold, "Use of hyaluronic acid fillers for the treatment of the aging face", 2007, Clinical Interventions in Aging, vol. 2, issue 3, pp. 369-376.*
Adams, Mark, An Analysis of Clinical Studies of the Use of Crosslinked Hyaluronan, Hylan, in the Treatment of Osteoarthritis, The Journal of Rheumatology, 1993, 16-18, 20 (39).
Aesthetic Buyers Guide, Juvederm Raises Standards, 2007, 1, 4-7; www.miinews.com.

(Continued)

*Primary Examiner* — Michael B Pallay
(74) *Attorney, Agent, or Firm* — Barbara C. Potts

(57) ABSTRACT

Dermal filler hydrogel compositions, methods of making them, and methods of using them to treat soft tissue conditions, such as wrinkles, are provided. The compositions contain a crosslinked hyaluronic acid-based polymer and one or more additional ingredients, and are stable to sterilization by heat and/or pressure treatment. The additional ingredients include vasoconstrictive agents, antioxidant agents, such as a ascorbic acid agents, and/or anesthetic agents.

20 Claims, 7 Drawing Sheets

(56) References Cited

U.S. PATENT DOCUMENTS

| | | | |
|---|---|---|---|
| 5,338,420 A | 8/1994 | Aga et al. |
| 5,356,883 A | 10/1994 | Kuo et al. |
| 5,399,351 A | 3/1995 | Leshchiner et al. |
| 5,407,812 A | 4/1995 | Sakai et al. |
| 5,428,024 A | 6/1995 | Chu et al. |
| 5,432,161 A | 7/1995 | Sakai et al. |
| 5,468,850 A | 11/1995 | Mandai et al. |
| 5,508,391 A | 4/1996 | Sakai et al. |
| 5,531,716 A | 7/1996 | Luzio et al. |
| 5,545,587 A | 8/1996 | Sugimoto et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto et al. |
| 5,616,689 A | 4/1997 | Shenoy et al. |
| 5,630,923 A | 5/1997 | Aga et al. |
| 5,633,001 A | 5/1997 | Agerup |
| 5,643,464 A | 7/1997 | Rhee et al. |
| 5,676,964 A | 10/1997 | Della Valle et al. |
| 5,759,532 A | 6/1998 | Galin |
| 5,767,149 A | 6/1998 | Yamamoto et al. |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai et al. |
| 5,880,107 A | 3/1999 | Buenter |
| 5,886,042 A | 3/1999 | Yu et al. |
| 5,935,164 A | 8/1999 | Iversen |
| 5,972,326 A | 10/1999 | Galin et al. |
| 5,980,930 A | 11/1999 | Fenton et al. |
| 6,013,679 A | 1/2000 | Kuo et al. |
| 6,066,325 A | 5/2000 | Wallace et al. |
| 6,224,857 B1 | 5/2001 | Romeo et al. |
| 6,248,905 B1 | 6/2001 | Fujinami et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,444,647 B1 | 9/2002 | Robinson et al. |
| 6,521,223 B1 | 2/2003 | Calias et al. |
| 6,544,503 B1 | 4/2003 | Vanderhoff et al. |
| 6,576,446 B2 | 6/2003 | Yamasaki et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci et al. |
| 6,767,924 B2 | 7/2004 | Yu et al. |
| 6,767,928 B1 | 7/2004 | Murphy et al. |
| 6,852,255 B2 | 2/2005 | Yang et al. |
| 6,893,466 B2 | 5/2005 | Trieu |
| 6,903,199 B2 | 6/2005 | Moon et al. |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg et al. |
| 7,196,180 B2 | 3/2007 | Aeschlimann et al. |
| 7,314,636 B2 | 1/2008 | Caseres et al. |
| 7,491,709 B2 | 2/2009 | Carey |
| 7,741,476 B2 | 6/2010 | Lebreton |
| 7,812,049 B2 | 10/2010 | Shanler |
| 7,902,171 B2 | 3/2011 | Reinmuller et al. |
| 8,114,898 B2 | 2/2012 | Shanler et al. |
| 8,124,120 B2 | 2/2012 | Sadozai et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0165079 A1 | 7/2005 | Shanler |
| 2005/0181007 A1 | 8/2005 | Hunter et al. |
| 2005/0186261 A1 | 8/2005 | Avelar et al. |
| 2005/0186673 A1 | 8/2005 | Geistlich et al. |
| 2005/0227936 A1 | 10/2005 | McSwiggen |
| 2005/0240147 A1* | 10/2005 | Makower ............... A61B 17/24 604/96.01 |
| 2005/0271729 A1 | 12/2005 | Wang |
| 2005/0276830 A1 | 12/2005 | DeJovin |
| 2005/0281880 A1 | 12/2005 | Wang |
| 2005/0287180 A1 | 12/2005 | Chen |
| 2006/0040894 A1* | 2/2006 | Hunter ................... A61K 31/19 514/54 |
| 2006/0095137 A1 | 5/2006 | Chung et al. |
| 2006/0122147 A1 | 6/2006 | Wohlrab et al. |
| 2006/0141049 A1 | 6/2006 | Lyons |
| 2006/0147483 A1 | 7/2006 | Chaouk et al. |
| 2006/0189516 A1 | 8/2006 | Yang et al. |
| 2006/0194758 A1* | 8/2006 | Lebreton ................ A61L 27/20 514/54 |
| 2006/0246137 A1 | 11/2006 | Hermitte et al. |
| 2006/0247722 A1 | 11/2006 | Maschino |
| 2006/0257488 A1 | 11/2006 | Hubbard |
| 2006/0264515 A1 | 11/2006 | Dejovin et al. |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0082070 A1 | 4/2007 | Stookey |
| 2007/0203095 A1 | 8/2007 | Sadozai et al. |
| 2007/0212385 A1 | 9/2007 | David |
| 2007/0224247 A1 | 9/2007 | Chudzik et al. |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0050335 A1 | 2/2008 | Faour et al. |
| 2008/0057091 A1 | 3/2008 | Abdellaoui et al. |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons et al. |
| 2008/0268051 A1 | 10/2008 | Hughes et al. |
| 2008/0274946 A1 | 11/2008 | Giampapa |
| 2008/0279806 A1 | 11/2008 | Cho |
| 2008/0293637 A1 | 11/2008 | Schroeder et al. |
| 2009/0018102 A1 | 1/2009 | Moutet et al. |
| 2009/0022808 A1 | 1/2009 | Champion et al. |
| 2009/0028817 A1 | 1/2009 | Niklason et al. |
| 2009/0036403 A1 | 2/2009 | Stroumpoulis et al. |
| 2009/0042834 A1 | 2/2009 | Karageozian |
| 2009/0054638 A1 | 2/2009 | Shelby |
| 2009/0060852 A1 | 3/2009 | DeJovin et al. |
| 2009/0093755 A1 | 4/2009 | Schroeder et al. |
| 2009/0110671 A1 | 4/2009 | Miyata et al. |
| 2009/0110736 A1 | 4/2009 | Boutros |
| 2009/0130027 A1 | 5/2009 | Shanler et al. |
| 2009/0143331 A1 | 6/2009 | Stroumpoulis et al. |
| 2009/0143348 A1 | 6/2009 | Tezel et al. |
| 2009/0148527 A1 | 6/2009 | Robinson et al. |
| 2009/0155314 A1 | 6/2009 | Tezel et al. |
| 2009/0155362 A1 | 6/2009 | Longin et al. |
| 2009/0169615 A1 | 7/2009 | Pinsky |
| 2009/0192533 A1 | 7/2009 | Dlugos |
| 2009/0192541 A1 | 7/2009 | Ortiz |

(56) References Cited

U.S. PATENT DOCUMENTS

| | | |
|---|---|---|
| 2009/0222065 A1 | 9/2009 | Dlugos |
| 2009/0263447 A1 | 10/2009 | Asius et al. |
| 2009/0291986 A1 | 11/2009 | Puppas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0130502 A1 | 5/2010 | Dejovin |
| 2010/0136070 A1 | 6/2010 | Dobak et al. |
| 2010/0226982 A1 | 9/2010 | Malessa |
| 2010/0226988 A1 | 9/2010 | Lebreton |
| 2010/0227867 A1 | 9/2010 | DeJovin |
| 2010/0255068 A1 | 10/2010 | Stroumpoulis et al. |
| 2010/0291171 A1 | 11/2010 | Crescenzi et al. |
| 2010/0316683 A1 | 12/2010 | Piron et al. |
| 2011/0034684 A1 | 2/2011 | Yokokawa et al. |
| 2011/0077737 A1 | 3/2011 | Stroumpoulis et al. |
| 2011/0091726 A1 | 4/2011 | Shibuya et al. |
| 2011/0118206 A1 | 5/2011 | Lebreton |
| 2011/0171286 A1 | 7/2011 | Cecile et al. |
| 2011/0171311 A1 | 7/2011 | Gousse et al. |
| 2011/0201571 A1 | 8/2011 | Gavard Molliard |
| 2011/0224164 A1 | 9/2011 | Lebreton |
| 2011/0224216 A1 | 9/2011 | Andres |
| 2011/0229574 A1 | 9/2011 | Guillen et al. |
| 2011/0286945 A1 | 11/2011 | DeJovin |
| 2011/0288096 A1 | 11/2011 | Graeber |
| 2012/0010146 A1 | 1/2012 | Han et al. |
| 2012/0034462 A1 | 2/2012 | Stroumpoulis et al. |
| 2012/0071437 A1 | 3/2012 | Stroumpoulis et al. |
| 2012/0135937 A1 | 5/2012 | Bertholon |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189591 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2012/0283428 A1 | 11/2012 | Lee et al. |
| 2012/0295870 A1 | 11/2012 | Lebreton |

FOREIGN PATENT DOCUMENTS

| | | |
|---|---|---|
| EP | 0273823 | 7/1988 |
| EP | 0416250 | 3/1991 |
| EP | 0416846 | 3/1991 |
| EP | 0555898 | 10/1993 |
| EP | 1247522 | 10/2002 |
| EP | 1398131 | 3/2004 |
| EP | 1419792 | 5/2004 |
| EP | 1532991 | 5/2005 |
| EP | 1726299 | 11/2006 |
| EP | 2236523 | 6/2010 |
| EP | 2435045 | 4/2012 |
| EP | 2435083 | 4/2012 |
| EP | 2484387 | 8/2012 |
| EP | 2207424 | 6/2014 |
| FR | 2733427 | 10/1996 |
| FR | 2920000 | 2/2009 |
| FR | 2924615 | 6/2009 |
| JP | 550153711 | 11/1980 |
| JP | 2007502645 | 2/2007 |
| JP | 2007063177 | 3/2007 |
| JP | 2007525541 | 9/2007 |
| JP | 2012508217 | 4/2012 |
| WO | 8600079 | 1/1986 |
| WO | 8600912 | 2/1986 |
| WO | 9200105 | 1/1992 |
| WO | 9220349 | 11/1992 |
| WO | 9401468 | 1/1994 |
| WO | 9402517 | 3/1994 |
| WO | 9633709 | 10/1996 |
| WO | 9633751 | 10/1996 |
| WO | 9704012 | 6/1997 |
| WO | 9835639 | 8/1998 |
| WO | 9835640 | 8/1998 |
| WO | 9949878 | 10/1999 |
| WO | 0001428 | 1/2000 |
| WO | 0179342 | 10/2001 |
| WO | 0205753 | 1/2002 |
| WO | 0206350 | 1/2002 |
| WO | 0209792 | 2/2002 |
| WO | 0217713 | 3/2002 |
| WO | 03007782 | 1/2003 |
| WO | 2004020473 | 3/2004 |
| WO | 2004022603 | 3/2004 |
| WO | 2004073759 | 9/2004 |
| WO | 2004092223 | 10/2004 |
| WO | 2005040224 | 6/2005 |
| WO | 2005067994 | 7/2005 |
| WO | 2005074913 | 8/2005 |
| WO | 2005112888 | 12/2005 |
| WO | 2006023645 | 3/2006 |
| WO | 2006031555 | 3/2006 |
| WO | 2006067608 | 6/2006 |
| WO | 2006102626 | 9/2006 |
| WO | 2007018124 | 2/2007 |
| WO | 2007070617 | 6/2007 |
| WO | 2007077399 | 7/2007 |
| WO | 2007128923 | 11/2007 |
| WO | 2007136738 | 11/2007 |
| WO | 2008015249 | 2/2008 |
| WO | 2008034176 | 3/2008 |
| WO | 2008068297 | 6/2008 |
| WO | 2008072230 | 6/2008 |
| WO | 2008077172 | 7/2008 |
| WO | 2008098019 | 8/2008 |
| WO | 2008139122 | 11/2008 |
| WO | 2008148967 | 12/2008 |
| WO | 2008157608 | 12/2008 |
| WO | 2009005790 | 1/2009 |
| WO | 2009024719 | 2/2009 |
| WO | 2009026158 | 2/2009 |
| WO | 2009028764 | 3/2009 |
| WO | 2009034559 | 3/2009 |
| WO | 2009073437 | 6/2009 |
| WO | 2010003797 | 1/2010 |
| WO | 2010015900 | 2/2010 |
| WO | 2010027471 | 3/2010 |
| WO | 2010028025 | 3/2010 |
| WO | 2010029344 | 3/2010 |
| WO | 2010038771 | 4/2010 |
| WO | 2010051641 | 5/2010 |
| WO | 2010052430 | 5/2010 |
| WO | 2010053918 | 5/2010 |
| WO | 2010061005 | 6/2010 |
| WO | 2010136585 | 12/2010 |
| WO | 2010136594 | 12/2010 |
| WO | 2011086458 | 7/2011 |
| WO | 2012104419 | 8/2012 |
| WO | 2012113529 | 8/2012 |

OTHER PUBLICATIONS

Albano, Emanuele et al., Hydroxyethyl Radicals in Ethanol Hepatotoxicity, Frontiers in Bioscience, 1999, 533-540, 4.

Allemann, Inja Bogdan, Hyaluronic Acid Gel (Juvederm) Preparations in the Treatment of Facial Wrinkles and Folds, Clinical Interventions in Aging, 2008, 629-634, 3 (4).

American Society for Aesthetic Plastic Surgery, http://www.surgery.org/media/news-release/115-million-cosmetic-procedures-in-2006; Mar. 9, 2007.

Anatelli, Florencia et al, Amorphous Basophilic Deposit in the Superficial Dermis of the Lip in an 80 Year Old, Am J Dermatophathol, 2010, 306-309, 32(3).

(56) References Cited

OTHER PUBLICATIONS

Antunes, Alberto et al., Efficacy of Intrarectal Lidocaine Hydrochloride Gel for Pain Control in Patients Undergoing Transrectal Prostate Biopsy, Clinical Urology, 2004, 380-383, 30.
Atanassoff, Peter et al., The Effect of Intradermal Administration of Lidocaine and Morphine on the Response to Thermal Stimulation, Anesth Analg, 1997, 1340-1343, 84.
Basran, G.S. et al, Adrenoceptor-Agonist Inhibition of the Histamine-Induced Cutaneuos Response in Man, British Journal of Dermatology, 1982, 140-142, 107.
Baumann, Leslie et al., Comparison of Smooth-Gel Hyaluronic Acid Dermal Fillers with Cross-linked Bovine collagen: A Multicenter, Double-Masked, Randomized, Within-Subject Study, Dermatologic Surgery, 2007, S128-135, 33 (2).
Beasley, Karen et al, Hyaluronic Acid Fillers: A Comprehensive Review, Facial Plastic Surgery, 2009, 86-94, 25 (2).
Beasley, Karen et al., Soft Tissue Augmentation Using a Two-Way Connector to Supplement Hyaluronic Acid Filler with 1% Lidocaine Hydrochloric Acid With Epinephrine 1:100000: Our Experience and Observations, Dermatol Surg, 2008, 524-526, 35.
Beer, Kenneth, Dermal Fillers and Combinations of Fillers for Facial Rejuvenation, Dermatologic Clin, 2009, 127-432, 27 (4).
Belda, Jose et al., Hyaluronic Acid Combined With Mannitol to Improve Protection Against Free-Radical Endothelial Damage: Experimental Model, J Cataract Refract Surg, 2005, 1213-1218, 31.
Bircher, Andres et al., Delayed-type Hypersensitivity to Subcutaneous Lidocaine With Tolerance to Articaine: Confirmation by In Vivo and In Vitro Tests, Contact Dermatitis, 1996, 387-389, 34.
Bluel, K. et al, Evaluation of Reconstituted Collagen Tape as a Model for Chemically Modified Soft Tissues, Biomat. Med. Dev. Art. Org., 1981, 37-46, 9 (1).
Buck, Donald, Injectable Fillers for Facial Rejuvenation: A Review, Journal of Plastic, Reconstructive & Aesthetic Surgery, 2009, 11-18, 62.
Busso, Mariano et al, An Investigation of Changes in Physical Properties of Injectable Calcium Hydroxylapatite in a Carrier Gel When Mixed with Lidocaine and with Lidocaine/Epinephrine, Dermatol Surg, 2008, S16-S24, 34.
Capozzi, Angelo et al., Distant Migration of Silicone Gel From a Ruptured Breast Implant, Silicone Gel Migration, 1978, 302-3, 62 (2).
Carlin, G. et al., Effect of Anti-Inflammatory Drugs on Xanthine Oxidase and Xanthine Oxidase Induced Depolymerization of Hyaluronic Acid, Agents and Actions, 1985, 377-384, 16 (5).
Carruthers, Alastair et al, Botulinum Toxin Type A: History and Current Cosmetic Use in the Upper Face, Semin Cutan Med Surg, 2001, 71-84, 20(2).
Carruthers, Jean et al, The Science and Art of Dermal Fillers for Soft-Tissue Augmentation, Journal of Drugs in Dermatology, 2009, 335-350, 8 (4).
Carruthers, Jean et al, Volumizing the Glabella and Forehead, Dermatol Surg, 2010, 1905-1909, 36.
Cassidy, James et al, Epinephrine: Systemic Effects and Varying Concentrations in Local Anesthesia, Anesth Prog, 1986, 289-297, 33(6).
Champion, Julie et al., Role of Target Geometry in Phagocytosis, Proc. Nat. Acad. Sci., 2006, 4930-4934, 103 (13).
Chemical Abstract Registry, RN 220644-17-7, RN 39479-63-5, 1 Page, 2016.
Chin, Thomas et al., Allergic Hypersensitivity to Lidocaine Hydrochloride, International Society of Tropical Dermatology, 1980, 147-148.
Chvapil, Milos, Collagen Sponge: Theory and Practice of Medical Applications, J. Biomed. Mater. Res., 1977, 121-741, 11.
Clark, D. Dick et al., The Influence of Triamcinolone Acetonide on Joint Stiffness in the Rat, The Journal of Bone and Joint Surgery, 1971, 1409-1414, 53A (7).
Cohen, Miriam et al., Organization and Adhesive Properties of the Hyaluronan Pericellular Coat of Chondrocytes and Epithelial Cells, Biophysical Journal, 2003, 1996-2005, 85.
Cui, Yu et al., The Comparison of Physicochemical Properties of Four Cross-linked Sodium Hyaluronate Gels With Different Cross-linking Agents, Advanced Materials Research, 2012, 1506-1512, 396-398.
Deland, Frank, Intrathecal Toxicity Studies with Benzyl Alcohol, Toxicology and Applied Pharmacology, 1973, 153-6, 25, Academic Press, Inc.
Desai, UR et al., Molecular Weight of Heparin Using 13C Nuclear Magnetic Resonance Spectroscopy, J Pharm Sci., 1995, 212-5, 84 (2).
Egbert, L.D. et al, Reduction of Bleeding by the Addition of Vasoconstrictor Drugs to Local Anesthetics, Annals of Surgery, 1962, 20-24, 155.
Eyre, David et al, Collagen Cross-Links, Top Curr Chem, 2005, 207-229, 247, Springer-Verlag, Berlin Heidelberg.
Fagien, Steven, Variable Reconstitution of Injectable Hyaluronic Acid With Local Anesthetic for Expanded Applications in Facial Aesthetic Enhancement, Dermatol Surg, 2010, 815-821, 36.
Falcone, Samuel et al, Temporary Polysaccharide Dermal Fillers: A Model for Persistence Based on Physical roperties, Dermatologic Surgery, 2009, 1238-1243, 35 (8).
Falcone, Samuel et al., Crosslinked Hyaluronic Acid Dermal Fillers: A Comparison of Rheological Properties, Journal of Biomedical Materials Research, 2008, 264-271, 87 (1).
Farley, Jon et al., Diluting Lidocaine and Mepivacaine in Balanced Salt Solution Reduces the Pain of Intradermal Injection, Regional Anesthesia, 1994, 48-51, 19 (1).
Folwaczny, C. et al, Influence of Prophylactic Local Administration of Epinephrine on Bleeding Complications After Polypectomy, Endoscopy, 1996, 31-33, 28.
Frati, Elena et al., Degradation of Hyaluronic Acid by Photosensitized Riboflavin In Vitro. Modulation of the Effect by Transition Metals, Radical Quenchers, and Metal Chelators, Free Radical Biology Medicine, 1996, 1139-1144, 22 (7).
Fujinaga, Masahiko et al., Reproductive and Teratogenic Effects of Lidocaine in Sprague-Dawley Rats, Anesthesiology, 1986, 626-632, 65.
Funt, David, Avoiding Malar Edema During Midface/Check Augmentation with Dermal Fillers, J Clin Aesthet Dermatol, Dec. 2011, 32-36, 4(12).
Gammaitoni, Arnold et al., Pharmacokinetics and Safety of Continuously Applied Lidocaine Patches 5%, Am J Health Syst Pharm, 2002, 2215-2220, 59.
Gassner, Holger et al, Addition of an Anesthetic Agent to Enhance the Predictability of the Effects of Botulinum Toxin Type A Injections: A Randomized Controlled Study, Mayo Clin Proc, 2000, 701-704, 75(7).
Ginshicel MH, Hydroxy Propyl Methyl Cellulose, Retrieved on Nov. 12, 2008 http://www.ginshicel.cn/MHPC.html, 2007, p. 1-3, 2 (3).
Gold, Michael, Use of Hyaluronic Acid Fillers for the Treatment of the Aging Face, Clin. Interventions Aging, 2007, 369-376, 2 (3).
Goldberg, David, Breakthroughs in US dermal fillers for facial soft-tissue augmentation, Journal of Cosmetic and Laser Therapy, 2009, 240-247, 11, Informa UK Ltd.
Graefe, Hendrik et al., Sensitive and Specific Photometric Determination of Mannitol, Clin Chem Lab Med, 2003, 1049-1055, 41 (8).
Grecomoro, G. et al., Intra-articular treatment with sodium hyaluronate in gonarthrosis: a controlled clinical trial iersus placebo, Pharmatherapeutica, 1987, 137-141, 5 (2).
Grillo, Hermes et al., Thermal Reconstitution of Collagen From Solution and the Response to Its Heterologous Implantation, JSR, 1962, 69-82, 2 (1).
Hantash, Basil et al, A Pilot Study on the Effect of Epinephrine on Botulinum Toxin Treatment for Periorbital Rhytides, Dermatologic Surgery, 2007, 461-468, 33.
Hassan, HG et al., Effects of Adjuvants to Local Anaesthetics on Their Duration. III. Experimental Studies of Hyaluronic Acid, Acta Anaesthesiol Scand., 1985, 1, 29 (4).
Hayashibara, AA2G, Sep. 23, 2007, Retrieved on Jan. 17, 2012, http://web.archive.org/web/20070923072010/http://www.hayashibara-intl.com/cosmetics/aa2g.html.

(56) References Cited

OTHER PUBLICATIONS

Helary, Christophe et al., Concentrated Collagen Hydrogels as Dermal Substitutes, Biomaterials, 2010, 481-490, 31.
Helliwell, Philip, Use of an objective measure of articular stiffness to record changes in finger joints after intra-articular injection of corticosteroid, Annals of Rheumatic Diseases, 1997, 71-73, 56.
Hertzberger-Ten, Cate et al., Intra-articular steroids in pauciarticular juvenile chronic arthritis, type 1, European Journal of Pediatrics, 1991, 170-172, 150.
Hetherington, NJ et al., Potential for Patient Harm from Intrathecal Administration of Preserved Solutions, Med J Aug. 2000, 1, 173(3).
Hong, Samin et al, Effect of Prophylactic Brimonidine Instillation on Bleeding During Strabismus Surgery in Adults, Am J Ophthalmol, 2007, 469-470, 144.
Hurst, E., Adhesive Arachnoiditis and Vascular Blockage Caused by Detergents and Other Chemical Irritants: An Expenmental Study, J Path. Bact., 1955, 167, 70.
Intramed (PTY) LTD, Intramed Mannitol 20% m/v Infusion, Package Insert, Jan. 1979, 4 pages, 12-214/8-94, ZA.
Jones, Adrian et al, Intra-articular Hyaluronic Acid Compared to Intra-articular Triamcinolone Hexacetonide in Inflammatory Knee Osteoarthritis, Osteoarthritis and Cartilage, 1995, 269-273, 3.
Jones, Derek, Semipermanent and Permanent Injectable Fillers, Dermatol Clin, 2009, 433-444, 27.
Kablik, Jeffrey et al, Comparative Physical Properties of Hyaluronic Acid Dermal Fillers, Dermatol Surg, 2009, 302-312, 35.
Klein, A., Skin Filling Collagen and Other Injectables of the Skin, Fundamentals of Cosmetic Surgery, 2001, 491-508, 3 (19).
Kopp, et al., The Short-term Effect of Intra-articular Injections of Sodium Hyaluronate and Corticosteroid on Temporomandibular Joint Pain and Dysfunction, Journal of Oral and Maxillofacial Surgery, 1985, 429-435, 43.
Kulicke, Werner-Michael et al., Visco-Elastic Properties of Sodium Hyaluronate Solutions, Institute for Technical and Macromolecular Chemistry, 2008, 585-587, DE.
Laeschke, Klaus, Biocompatibility of Microparticles Into Soft Tissue Fillers, Semin Cutan Med Surg, 2004, 214-217, 23.
Lamar, PD et al., Antifibrosis Effect of Novel Gels in Anterior Ciliary Sclerotomy (ACS), 2002, 1 Page, The Association for Research in Vision and Ophthalmology, Inc.
Levy, Jaime et al., Lidocaine Hypersensitivity After Subconjunctival Injection, Can J Ophthalmol, 2006, 204-206, 41.
Lindgren, Bjorn et al, Inhibitory Effects of Clonidine on Allergic Reactions in Guinea-Pig Skin, European Journal of Pharmacology, 1987, 339-343, 134.
Lindvall, Sven et al., Influence of Various Compounds on the Degradation of Hyaluronic Acid by a Myeloperoxidase System, Chemico-Biological Interactions, 1994, 1-12, 90.
Lundeberg, T. et al, Epinephrine Reduces the Severity of Catheter-Induced Urethral Inflammation by Action at the α2-Adrenoceptors, British Journal of Urology, 1993, 349-352, 72.
Lupo, Mary, Hyaluronic Acid Fillers in Facial Rejuvenation, Seminars in Cutaneous Medicine and Surgery, 2006, 122-126, 25.
Mackley, Christine et al., Delayed-Type Hypersensitivity to Lidocaine, Arch Dermatol, 2003, 343-346, 139.
Mancinelli, Laviero et al., Intramuscular High-dose Triamcinolone Acetonide in the Treatment of Severe chronic Asthma, West J Med, 1997, 322-329, 167 (5).
Maniglia-Ferreira, Claudlo et al, Clinical Evaluation of the Use of Three Anesthetics in Endodontics, Acta Odontol Latinoam, 2009, 21-26, 22(1).
Martin, Donna et al, Fine Rhytides Treated with Porcine Collagen-Derived Filler Mixed with Anesthetic, Dermatol Surg, 2010, 270-272, 36(2).
Matsumoto, Alan et al., Reducing the Discomfort of Lidocaine Administration Through pH Buffering, Journal of Vascular and Interventional Radiology, 1994, 171-175, 5 (1).
McCarty, Daniel et al, Inflammatory Reaction after Intrasynovial Injection of Microcrystalline Adrenocorticosteroid Esters, Arthritis and Rheumatism, 1964, 359-367, 7 (4).
McCleland, Marcee et al., Evaluation of Artecoll Polymethylmethacrylate Implant for Soft-Tissue Augmentation: Biocompatibility and Chemical Characterization, Plastic & Reconstructive Surgery, 1997, 1466-1474, 100 (6).
McPherson, John et al., Development and Biochemical Characterization of Injectable Collagen, Journal of Dermatol Surg Oncol, 1988, 13-20, 14 (Suppl 1) 7.
Menon, Harikumar et al, Low Dose of Hyaluronidase to Treat Over Correction by HA Filler—A Case Report, Journal of Plastic, Reconstructive & Aesthetic Surgery, 2010, e416-e417, 63.
Michael S. McCracken, Hyaluronic Acid Gel (Restylane) Filler for Facial Rhytids: Lessons Learned From American Society of Ophthalmic Plastic and Reconstructive Surgery Member Treatment of 286 Patients, Ophthalmic Plastic and Reconstructive Surgery, 2006, 188-191, 22 (3).
Millay, Donna et al., Vasoconstrictors in Facial Plastic Surgery, Arch Otolaryngol Head Neck Surg., 1991, 160-163, 117.
Naoum, Christos et al, Dermal Filler Materials and Botulin Toxin, International Journal of Dermatology, 2001, 509-621, 40.
Orvisky, E. et al., High-molecular-weight Hyaluronan—a Valuable Tool in Testing the Antioxidative Activity of Amphiphilic Drugs Stobadine and Vinpocetine, Journal of Pharm. Biomed. Anal., 1997, 419-424, 16.
Osmitrol (generic name Mannitol), Official FDA Information, side effects and uses, http://www.drugs.com/pro/osmitrol.html, 2010, 10 Pages.
Palmon, Sally et al, The Effect of Needle Gauge and Lidocaine pH on Pain During Intradermal Injection, Anesth Analg, 1998, 379-381, 86.
Park, Si-Nae et al., Biological Characterization of EDC-Crosslinked Collagen-Hyaluronic Acid Matrix in Dermal Tissue Restoration, Biomaterials, 2003, 1631-1641, 24.
Park, Si-Nae et al., Characterization of Porous Collagen/Hyaluronic Acid Scaffold Modified by 1-Ethyl-3-(3-Dimethylaminopropyl)Carbodiimide Cross-Linking, Biomaterials, 2002, 1205-1212, 23.
Phenylephrine. Open Drug Data and Drug Target Database 2013; http://www.drugbank.ca/drugsIDB00388. Accessed May 6, 2013.
Powell, Michael, Stability of Lidocaine in Aqueous Solution: Effect of Temperature, pH, Buffer, and Metal Ions on Amide Hydrolysis, Pharmaceutical Research, 1987, 42-45, 4 (1).
Prestwich, Glenn, Evaluating Drug Efficacy and Toxicology in Three Dimensions: Using Synthetic Extracellular Matrices in Drug Discovery, Accounts of Chemical Research, Jan. 2008, 139-148, 41(1).
Rehakova, Milena et al., Properties of Collagen and Hyaluronic Acid Composite Materials and Their Modification by Chemical Crosslinking, Journal of Biomedical Materials Research, 1996, 369-372, 30, US.
Remington's Pharmaceutical Sciences, 1980, 16th Edition, Mack Publishing Company, Easton, Pennsylvania.
Romero-Sandoval, Alfonso et al, Clonidine Reduces Hypersensitivity and Alters the Balance of Pro- and Anti-Inflammatory Leukocytes After Local Injection at the Site of Inflammatory Neuritis, Brain Behav Immun, Jul. 2007, 569-580, 21(5).
Rosenblatt, J. et al., Chain Rigidity and Diffusional Release in Biopolymer Gels, Controlled Release Society, 1993, 264-265, 20.
Rosenblatt, J. et al., The Effect of Collagen Fiber Size Distribution on the Release Rate of Proteins From collagen Matrices by Diffusion, J Controlled Release, 1989, 195-203, 9.
Sannino, A. et al., Crosslinking of Cellulose Derivatives and Hyaluronic Acid With Water-Soluble Carbodiimide, Polymer, 2005, 11206-11212, 46.
Sculptra ® Aesthetic (injectable poly-L-lactic acid) Directions for Use, Product Insert, Jul. 2009, 12 Pages, Dermik Laboratories.
Segall, A.I. et al, Stability of Vitamin C Derivatives in Topical Formulations Containing Lipoic Acid, Vitamins A and E, International Journal of Cosmetic Science, 2008, 453-458, 30.
Segura, Tatiana et al., Crosslinked Hyaluronic Acid Hydrogels: A Strategy to Functionalize and Pattern, Biomaterials, 2005, 359-371, 26 (4).
Selvi, Enrico et al., Arthritis Induced by Corticosteroid Crystals, The Journal of Rheumatology, 2004, 622, 31 (3).

(56) References Cited

OTHER PUBLICATIONS

Serban, et al., Modular Extracellular Matrices: Solutions for the Puzzle, Methods, 2008, 93-98, 45 (1).

Shoroghi, Mehrdad et al, Effect of Different Epinephrine Concentrations on Local Bleeding and Hemodynamics During Dermatologic Surgery, Acta Dermatovenerol Croat, 2008, 209-214, 16(4).

Shu, Xiao et al, Synthesis and evaluation of injectable, in situ crosslinkable synthetic extracellular matrices for tissue engineering, Journal of Biomedical Materials Research, 2006, 902-912, 79A.

Silver, Frederick et al., Physical Properties of Hyaluronic Acid and Hydroxypropylmethylcellulose in Solution: Evaluation of Coating Ability, Journal of Applied Biomaterials, 1994, 89-98, 5.

Skardal, Aleksander et al., Bioprinting Vessel-Like Constructs Using Hyaluronan Hydrogels Crosslinked With Tetrahedral Polyethylene Glycol Tetracrylates, Biomaterials, 2010, 6173-6181, 31.

Smith, Kevin et al., Five Percent Lidocaine Cream Applied Simultaneously to the Skin and Mucosa of the Lips Creates Excellent Anesthesia for Filler Injections, Dermatol Surg, 2005, 1635-1637, 31.

Tezel, Ahmet et al., The science of hyaluronic acid dermal fillers, Journal of Cosmetic and Laser Therapy, 2008, 35-42, 10.

Visiol, TRB Chemedica Ophthalmic Line, Product Info, May 2014, p. 1-2, Geneva, CH.

Visiol, Viscoelstic Gel for Use in Ocular Surgery, http://www.trbchemedica.com/index.php/option=com_content&tas, 2010, 1 Page.

Vivawoman, Sodium Ascorbyl Phosphate: A Stable Vitamin C, Nov. 3, 2010, 13 Pages, http://www.vivawoman.net/2010/11/sodium-ascrobyl-phosphate-a-stable-vitamin-c/.

Wahl, Gregor, European Evaluation of a New Hyaluronic Acid Filler Incorporating Lidocaine, Journal of Cosmetic Dermatology, 2008, 298-303, 7.

Waraszkiewicz, Sigmund et al., Stability-Indicating High-Performance Liquid Chromatographic Analysis of Lidocaine Hydrochloride and Lidocaine Hydrochloride with Epinephrine Injectable Solutions, Journal of Pharmaceutical Sciences, 1981, 1215-1218, 70 (11).

Weidmann, Michael, New Hyaluronic Acid Filler for Subdermal and Long-lasting Volume Restoration of the Face, European Dermatology, 2009, 65-68.

Kia, Yun et al., Comparison of Effects of Lidocaine Hydrochloride, Buffered Lidocaine, Diphenhydramine, and Normal Saline After Intradermal Injection, Journal of Clinical Anesthesia, 2002, 339-343, 14.

Yeom, Junseok et al., Effect of Cross-Linking Reagents for Hyaluronic Acid Hydrogel Dermal Fillers on Tissue Augmentation and Regeneration, Bioconjugate Chemistry, 2010, 240-247, 21, American Chemical Society.

Yoshimura, Kotaro et al., Cell-Assisted Lipotransfer for Cosmetic Breast Augmentation: Supportive Use of Adipose-Derived Stem/Stromal Cells, Aesth. Plast. Surg., 2008, 48-55, 32.

Yui, Nobuhiko et al., Inflammation Responsive Degradation of Crosslinked Hyaluronic Acid Gels, Journal of Controlled Release, 1992, 105-116, 26.

Yui, Nobuhiko et al., Photo-Responsive Degradation of Heterogeneous Hydrogels Comprising Crosslinked Hyaluronic Acid and Lipid Microspheres for Temporal Drug Delivery, Journal of Controlled Release, 1993, 141-145, 26.

Yun, Yang H. et al., Hyaluronan Microspheres for Sustained Gene Delivery and Site-Specific Targeting, Biomaterials, 2004, 147-157, 25, US.

Zheng et al., In Situ Crosslinkable Hyaluronan Hydrogels for Tissue Engineering, Biomaterials, 2004, 1339-1348, 25.

Zulian, F. et al., Triamcinolone Acetonide and Hexacetonide Intra-Articular Treatment of Symmetrical Joints in Juvenile Idiopathic Arthritis: A Double-Blind Trial, Rheumatology, 2004, 1288-1291, 43.

* cited by examiner

STABLE HYDROGEL COMPOSITIONS INCLUDING ADDITIVES

CROSS REFERENCE

This patent application is a continuation of U.S. patent application Ser. No. 13/350,518, filed on Jan. 13, 2012, which is a continuation-in-part of U.S. patent application Ser. No. 13/005,860, filed Jan. 13, 2011, which is a continuation-in-part of U.S. patent application Ser. No. 12/956,542, filed on Nov. 30, 2010, which is a continuation-in-part of U.S. patent application Ser. No. 12/714,377, filed on Feb. 26, 2010, which is a continuation-in-part of U.S. patent application Ser. No. 12/687,048, filed Jan. 13, 2010, the disclosure of each of these applications incorporated in its entirety by this reference.

BACKGROUND

Skin aging is a progressive phenomenon, occurs over time and can be affected by lifestyle factors, such as alcohol consumption, tobacco and sun exposure. Aging of the facial skin can be characterized by atrophy, slackening, and fattening. Atrophy corresponds to a massive reduction of the thickness of skin tissue. Slackening of the subcutaneous tissues leads to an excess of skin and ptosis and leads to the appearance of drooping cheeks and eye lids. Fattening refers to an increase in excess weight by swelling of the bottom of the face and neck. These changes are typically associated with dryness, loss of elasticity, and rough texture.

Hyaluronan, also known as hyaluronic acid (HA) is a non-sulfated glycosaminoglycan that is distributed widely throughout the human body in connective, epithelial, and neural tissues. Hyaluronan is abundant in the different layers of the skin, where it has multiple functions such as, e.g., to ensure good hydration, to assist in the organization of the extracellular matrix, to act as a filler material; and to participate in tissue repair mechanisms. However, with age, the quantity of hyaluronan, collagen, elastin, and other matrix polymers present in the skin decreases. For example, repeated exposed to ultra violet light, e.g., from the sun, causes dermal cells to both decrease their production of hyaluronan as well as increase the rate of its degradation. This hyaluronan loss results in various skin conditions such as, e.g., imperfects, defects, diseases and/or disorders, and the like. For instance, there is a strong correlation between the water content in the skin and levels of hyaluronan in the dermal tissue. As skin ages, the amount and quality of hyaluronan in the skin is reduced. These changes lead to drying and wrinkling of the skin.

Dermal fillers are useful in treating soft tissue condition and in other skin therapies because the fillers can replace lost endogenous matrix polymers, or enhance/facilitate the function of existing matrix polymers, in order to treat these skin conditions. In the past, such compositions have been used in cosmetic applications to fill wrinkles, lines, folds, scars, and to enhance dermal tissue, such as, e.g., to plump thin lips, or fill-in sunken eyes or shallow cheeks. One common matrix polymer used in dermal filler compositions is hyaluronan. Because hyaluronan is natural to the human body, it is a generally well tolerated and a fairly low risk treatment for a wide variety of skin conditions.

Originally, compositions comprising hyaluronan where made from naturally-occurring polymers, which exist in an uncrosslinked state. Although exhibiting excellent biocompatibility and affinity for water molecules, naturally-occurring hyaluronan exhibits poor biomechanical properties as a dermal filler. Tezel and Fredrickson, *The Science of Hyaluronic Acid Dermal Fillers*, J. Cosmet. Laser Ther. 10(1): 35-42 (2008); Kablik, et al., *Comparative Physical Properties of Hyaluronic Acid Dermal Fillers*, Dermatol. Surg. 35 Suppl 1: 302-312 (2009); Beasley, et al., *Hyaluronic Acid Fillers: A Comprehensive Review*, Facial Plast. Surg. 25(2): 86-94 (2009); each of which is hereby incorporated by reference in its entirety. One primary reason is that because this polymer is uncrosslinked, it is highly soluble and, as such, is cleared rapidly when administered into a skin region. Tezel, supra, 2008; Kablik, supra, 2009; Beasley, supra, 2009. This in vivo clearance is primarily achieved by rapid degradation of the polymers, principally enzymatic degradation via hyaluronidase and chemical degradation via free-radicals. Thus, while still in commercial use, compositions comprising uncrosslinked hyaluronan polymers tend to degrade within a few days after administration and thus require fairly frequent reinjection to maintain their skin improving effect.

To minimize the effect of these in vivo degradation pathways, matrix polymers are crosslinked to one another to form a stabilized hydrogel. Because hydrogels comprising crosslinked matrix polymers are a more solid substance, dermal fillers comprising such hydrogels remain in place at the implant site longer. Tezel, supra, 2008; Kablik, supra, 2009; Beasley, supra, 2009. In addition, these hydrogels are more suitable as a dermal filler because it's more solid nature improves the mechanical properties of the filler, allowing the filler to better lift and fill a skin region. Tezel, supra, 2008; Kablik, supra, 2009; Beasley, supra, 2009. Hyaluronan polymers are typically crosslinked with a crosslinking agent to form covalent bonds between hyaluronan polymers. Such crosslinked polymers form a less water soluble hydrogel network that is more resistant to degradation, and thus requires less frequent reinjection, than the non-crosslinked hyaluronan compositions.

Current dermal fillers can be associated with a variety of side effects. For example, administration of a dermal filler to an individual is typically performed using a syringe or needle. Such administration could result in one or more unwanted side-effects, such as, e.g., pain and discomfort to the individual, bleeding in and under the site of administration, and itching, inflammation and irritation in the vicinity of the administration site during and after the administration of the dermal filler. The dermal fillers disclosed in the present specification address these and other unwanted side-effects by providing hydrogel compositions comprising agents that reduce, step, or prevent one or more of these side-effects.

Additionally, a dermal filler formulation must be capable of withstanding sterilization which is a strict requirement before the product can be sold (the product must be sterile). Sterilization can be carried out by steam sterilization, filtration, microfiltration, gamma radiation, ETO light or by a combination of these methods. It is known that a dermal filler can be steam sterilized (autoclaved) without substantial degradation of physical properties, but when a dermal filler formulation contains an additional labile ingredient (such as an antioxidant, anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, or a moisturizing agent) the entire dermal filler formulation or at least the additional (heat labile) agent is traditionally sterilized by a non-heat treatment such as by a filtration sterilization method. Thus, a known dermal filler product (REVITACARE® Bio-Revitalisation, REVITACARE® Laboratory, Saint-Ouen-l'Aumône, France) is sold in two separate vials or containers, one vial containing the HA (which is autoclave sterilized)) and the second vial containing any additional ingredients (the second vial contents are sterilized by filtration). Another known dermal filler product NCTF® 135HA (Laboratoires Filorga, Paris, France) is sold in a single container holding both hyaluronan and any additional ingredients, all having been sterilized by microfiltration. The dermal fillers disclosed in the present specification addresses this issue by developing dermal fillers that are entirely sterilized by a heat treatment, i.e., in some embodiments of this invention, none of the components are sterilized solely using a non-heat treatment such as, e.g., filtration.

SUMMARY

The present specification provides novel dermal fillers useful for treating skin conditions that remain stable after a heat treatment used to sterilize the compositions. One aspect of the disclosed dermal fillers, and a significant distinction over known dermal fillers, is that dermal fillers disclosed herein are prepared by: 1) mixing glycosaminoglycan polymers and the additional agents(s) disclosed herein, and then; (2) heat treating the dermal filler composition to at least 100° C. (no filtration sterilization of any component); (3) where such treatment maintains the desired properties of the hydrogel compositions. The disclosed hydrogel compositions do not exhibit any significant degradation as shown by pre and post autoclaved testing. The disclosed hydrogel compositions are substantially heat stable as determined by the retention of one or more of the following characteristics after sterilization: clarity (transparency and translucency), homogeneousness, extrusion force, cohesiveness, hyaluronan concentration, agent(s) concentration, osmolarity, pH, or other rheological characteristics desired by the hydrogel before the heat treatment.

The hydrogel compositions disclosed herein can also exhibit greater stability than a hydrogel composition without the additional constituent. Without wishing to be bound by theory it may be that the hydrogel matrix of the cross-linked glycosaminoglycan polymers used in our formulation sequesters, renders non-reactive and thereby prevents the additional ingredient (as set forth in Examples following) from degrading and causes degradation of the dermal filler formulation during steam sterilization. Additionally, the additional ingredient can be hydrophilic and provides protection to the glycosaminoglycan polymers from degradation during steam sterilization and/or after administration of the dermal filler formulation to a patient. Without wishing to be bound by theory, the incorporation of an additional ingredient in the dermal filler formulation may inhibit free-radical scavenging at the injection/implant site, thereby prolonging dermal filler duration after patient administration. After steam sterilization, the additional ingredient can, upon administration (as by subdermal injection), be released from the dermal filler formulation for cosmetic or therapeutic effect.

Thus, aspects of the present specification provide a hydrogel composition comprising a glycosaminoglycan polymer and at least one agent selected from an antioxidant, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, or a moisturizing agent. Glycosaminoglycan polymers useful to make such compositions include, without limitation, chondroitin sulfate polymers, dermatan sulfate polymers, keratan sulfate polymers, and hyaluronan polymers.

Other aspects of the present specification provide a method of preparing a hydrogel composition disclosed herein, the method comprising a) mixing the glycosaminoglycan polymer and the at least one agent; and b) heat treating the mixture; wherein the heat treatment maintains the desired hydrogel properties disclosed herein.

Yet other aspects of the present specification provide a method of treating a skin condition in an individual in need thereof, the method comprising the steps of administering a hydrogel composition disclosed herein into a dermal region of the individual, wherein the administration improves the skin condition. Skin conditions treated by the disclosed compositions include, without limitation, augmentations, reconstructions, diseases, disorders, defects, or imperfections of a body part, region or area. In one aspect, a skin condition treated by the disclosed compositions include, without limitation, a facial augmentation, a facial reconstruction, a facial disease, a facial disorder, a facial defect, or a facial imperfection. In one aspect, a skin condition treated by the disclosed compositions include, without limitation, skin dehydration, a lack of skin elasticity, skin roughness, a lack of skin tautness, a skin stretch line or mark, skin paleness, a dermal divot, a sunken cheek, a thin lip, a retro-orbital defect, a facial fold, or a wrinkle.

In other aspects of the invention, a hydrogel composition comprising a hyaluronic acid-based polymer and at least one additional agent selected from the group consisting of an antihemorrhagic agent and a vasoconstrictor agent is provided, wherein the hydrogel composition is sterilized by heat treatment and/or pressure treatment, for example, by autoclaving, for example, is sterilized in a process comprising a heat treatment of at least 100° C. Advantageously, the heat sterilized composition is substantially stable at room temperature for up to at least about 3 months, for example, at least about 12 months, at least about 24 months, or at least about 36 months.

In some embodiments, the antihemorrhagic agent is an antifibrinolytic agent selected from the group ε-aminocaproic acid, tranexamic acid, and a serpin. In some embodiments, the antifibrinolytic agent is tranexamic acid present in an amount of about 0.1% (w/w) to about 1.0% (w/w) of the total composition.

In some embodiments, the vasoconstrictor agent is naphazoline, epinephrine, methoxamine, methylnorepinephrine, norepinephrine, oxymetazoline, phenylephrine, pseudoephedrine, synephrine, cirazoline, xylometazoline, an analog or a derivative thereof, or any combination thereof. In some embodiments, phenylephrine is present at a concentration of about 0.001% (w/w) to about 0.1% (w/w). In some embodiments, the phenylephrine is present in an amount of between about 100 ppm to about 500 ppm, for example, between about 300 ppm and about 400 ppm. In some embodiments, phenylephrine is present in an amount of about 400 ppm. In some embodiments, the composition further comprises an anesthetic agent, for example, lidocaine or a similar agent, present in an amount of about 0.1% (w/w) to about 1.0% (w/w) of the total composition. In some embodiments, lidocaine is present in an amount of about 0.3% w/w. In some embodiments, the composition further comprises an antioxidant agent, for example, mannitol present in an amount of about 0.01% (w/w) to about 5% (w/w) of the total composition.

In a one embodiment, an injectable dermal filler composition is provided comprising a crosslinked hyaluronic acid-based polymer and phenylephrine present at a concentration of about 300 ppm to about 400 ppm. In some embodiments, the composition has been sterilized, for example, heat sterilized, in a process comprising a heat treatment of at least 100° C., and is substantially stable at room temperature for at least 6 months or more, for example, for at least 12 months. The composition may further comprise lidocaine mixed with the crosslinked hyaluronic acid-based polymer and phenylephrine. The lidocaine may be present in an amount of between about 0.1% and about 1.0% w/w. For example, the lidocaine may be present in an amount of about 0.3% w/w.

In some embodiments, the hyaluronic acid-based polymer is present at a concentration of about 5 mg/g to about 40 mg/g, and comprises a low molecular weight hyaluronan polymer having a mean molecular weight greater than 300,000 Da and less than about 800,000 Da, for example, a mean molecular weight greater than 2,000,000 Da and less than about 5,000,000 Da. In some embodiments, the hyaluronic acid-based polymer comprises both high molecular weight hyaluronan and low molecular weight hyaluronan, wherein the high molecular weight hyaluronan has a molecular weight greater than 2,000,000 Da and wherein the low molecular weight hyaluronan has a molecular weight of less than 1,000,000 Da.

DETAILED DESCRIPTION

Figure 1:
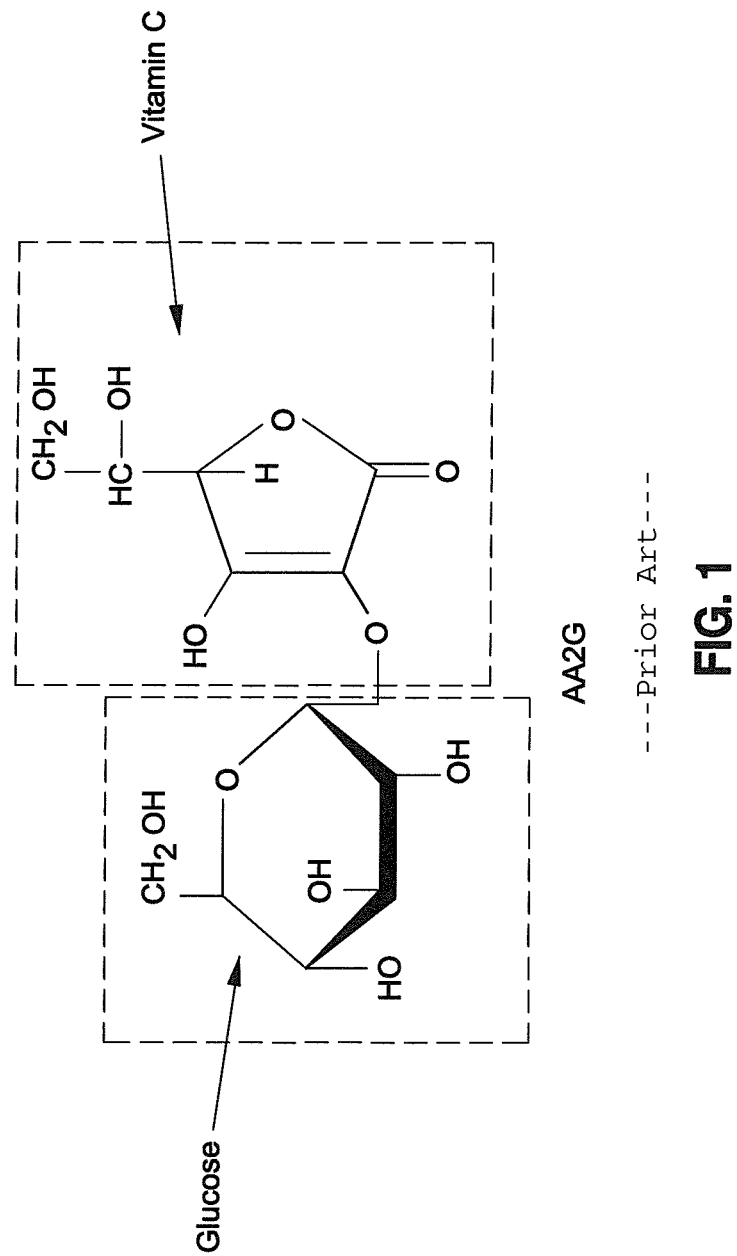
FIG. 1 is a representation of the structure of an ascorbyl-2-glucoside, also known as AA2G™ (Hayashibara International, Okayama, Japan).

Aspects of the present specification provide, in part, a hydrogel composition comprising a glycosaminoglycan polymer. The hydrogel composition disclosed herein can further comprise two or more different glycosaminoglycan polymers. As used herein, the term "glycosaminoglycan" is synonymous with "GAG" and "mucopolysaccharide" and refers to long unbranched polysaccharides consisting of a repeating disaccharide units. The repeating unit consists of a hexose (six-carbon sugar) or a hexuronic acid, linked to a hexosamine (six-carbon sugar containing nitrogen) and pharmaceutically acceptable salts thereof. Members of the GAG family vary in the type of hexosamine, hexose or hexuronic acid unit they contain, such as, e.g., glucuronic acid, iduronic acid, galactose, galactosamine, glucosamine) and may also vary in the geometry of the glycosidic linkage. Any glycosaminoglycan polymer is useful in the hydrogel compositions disclosed herein with the proviso that the glycosaminoglycan polymer improves a condition of the skin. Non-limiting examples of glycosaminoglycans include chondroitin sulfate, dermatan sulfate, keratan sulfate, hyaluronan. Non-limiting examples of an acceptable salt of a glycosaminoglycans includes sodium salts, potassium salts, magnesium salts, calcium salts, and combinations thereof. Glycosaminoglycan and their resulting polymers useful in the hydrogel compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety. GAGs useful in the hydrogel compositions and methods disclosed herein are commercially available, such as, e.g., hyaluronan-based dermal fillers JUVEDERM®, JUVEDERM® 30, JUVEDERM® Ultra, JUVEDERM® Ultra Plus, JUVEDERM® Ultra XC, and JUVEDERM® Ultra Plus XC (Allergan Inc, Irvine, Calif.). Table 1 lists representative GAGs.

TABLE 1

Examples of GAGs

| Name | Hexuronic acid/Hexose | Hexosamine | Glycosidic linkage geometry | Unique features |
|---|---|---|---|---|
| Chondroitin sulfate | GlcUA or GlcUA(2S) | GalNAc or GalNAc(4S) or GalNAc(6S) or GalNAc(4S,6S) | -4GlcUAβ1-3GalNAcβ1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUAβ1-3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1-4GlcNAc(6S)β1- | Keratan sulfate type II may be fucosylated. |
| Heparin | GlcUA or IdoUA(2S) | GlcNAc or GlcNS or GlcNAc(6S) or GlcNS(6S) | -4IdoUA(2S)α1-4GlcNS(6S)α1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organised into distinct sulfated and non-sulfated domains. |
| Hyaluronan | GlcUA | GlcNAc | -4GlcUAβ1-3GlcNAcβ1- | The only GAG that is exclusively non-sulfated |

GlcUA = β-D-glucuronic acid
GlcUA(2S) = 2-O-sulfo-β-D-glucuronic acid
IdoUA = α-L-iduronic acid
IdoUA(2S) = 2-O-sulfo-α-L-iduronic acid
Gal = β-D-galactose
Gal(6S) = 6-O-sulfo-β-D-galactose
GalNAc = β-D-N-acetylgalactosamine
GalNAc(4S) = β-D-N-acetylgalactosamine-4-O-sulfate
GalNAc(6S) = β-D-N-acetylgalactosamine-6-O-sulfate
GalNAc(4S,6S) = β-D-N-acetylgalactosamine-4-O, 6-O-sulfate
GlcNAc = α-D-N-acetylglucosamine
GlcNS = α-D-N-sulfoglucosamine
GlcNS(6S) = α-D-N-sulfoglucosamine-6-O-sulfate Aspects of the present specification provide, in part, a hydrogel composition comprising a chondroitin sulfate polymer. As used herein, the term "chondroitin sulfate polymer" refers to an unbranched, sulfated polymer of variable length comprising disaccharides of two alternating monosaccharides of D-glucuronic acid (GlcA) and N-acetyl-D-galactosamine (GalNAc) and pharmaceutically acceptable salts thereof. A chondroitin sulfate polymer may also include D-glucuronic acid residues that are epimerized into L-iduronic acid (IdoA), in which case the resulting disaccharide is referred to as dermatan sulfate. A chondroitin sulfate polymer can have a chain of over 100 individual sugars, each of which can be sulfated in variable positions and quantities. Chondroitin sulfate polymers are an important structural component of cartilage and provide much of its resistance to compression. Any chondroitin sulfate polymer is useful in the compositions disclosed herein with the proviso that the chondroitin sulfate polymer improves a condition of the skin. Non-limiting examples of pharmaceutically acceptable salts of chondroitin sulfate include sodium chondroitin sulfate, potassium chondroitin sulfate, magnesium chondroitin sulfate, calcium chondroitin sulfate, and combinations thereof.

Aspects of the present specification provide, in part, a hydrogel composition comprising a keratan sulfate polymer. As used herein, the term "keratan sulfate polymer" refers to a polymer of variable length comprising disaccharide units, which themselves include β-D-galactose and N-acetyl-D-galactosamine (GalNAc) and pharmaceutically acceptable salts thereof. Disaccharides within the repeating region of keratan sulfate may be fucosylated and N-Acetylneuraminic acid caps the end of the chains. Any keratan sulfate polymer is useful in the compositions disclosed herein with the proviso that the keratan sulfate polymer improves a condition of the skin. Non-limiting examples of pharmaceutically acceptable salts of keratan sulfate include sodium keratan sulfate, potassium keratan sulfate, magnesium keratan sulfate, calcium keratan sulfate, and combinations thereof.

Aspects of the present specification provide, in part, a hydrogel composition comprising a hyaluronan polymer. As used herein, the term "hyaluronic acid polymer" is synonymous with "HA polymer", "hyaluronic acid polymer", and "hyaluronate polymer" refers to an anionic, non-sulfated glycosaminoglycan polymer comprising disaccharide units, which themselves include D-glucuronic acid and D-N-acetylglucosamine monomers, linked together via alternating β-1,4 and β-1,3 glycosidic bonds and pharmaceutically acceptable salts thereof. Hyaluronan polymers can be purified from animal and non-animal sources. Polymers of hyaluronan can range in size from about 5,000 Da to about 20,000,000 Da. Any hyaluronan polymer is useful in the compositions disclosed herein with the proviso that the hyaluronan improves a condition of the skin. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a hydrogel composition comprising a crosslinked glycosaminoglycan polymer. As used herein, the term "crosslinked" refers to the intermolecular bonds joining the individual polymer molecules, or monomer chains, into a more stable structure like a gel. As such, a crosslinked glycosaminoglycan polymer has at least one intermolecular bond joining at least one individual polymer molecule to another one. The crosslinking of glycosaminoglycan polymers typically result in the formation of a hydrogel. Such hydrogels have high viscosity and require considerable force to extrude through a fine needle. Glycosaminoglycan polymers disclosed herein may be crosslinked using dialdehydes and disulfides crosslinking agents including, without limitation, multifunctional PEG-based crosslinking agents, divinyl sulfones, diglycidyl ethers, and bis-epoxides, biscarbodiimide. Non-limiting examples of hyaluronan crosslinking agents include multifunctional PEG-based crosslinking agents like pentaerythritol tetraglycidyl ether (PETGE), divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), (phenylenebis-(ethyl)-carbodiimide and 1,6 hexamethylenebis (ethylcarbodiimide), adipic dihydrazide (ADH), bis(sulfosuccinimidyl)suberate (BS), hexamethylenediamine (HMDA), 1-(2,3-epoxypropyl)-2,3-epoxycyclohexane, or combinations thereof. Other useful cross-linking agents are disclosed in Stroumpoulis and Tezel, Tunably Crosslinked Polysaccharide Compositions, U.S. patent application Ser. No. 12/910,466, filed Oct. 22, 2010, which is incorporated by reference in its entirety. Non-limiting examples of methods of crosslinking glycosaminoglycan polymers are described in, e.g., Glycosaminoglycan polymers useful in the compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety.

In accordance with the present specification, "%" in a formulation is defined as weight by weight (i.e., w/w) percentage. As an example: 1% (w/w) means a concentration of 10 mg/g.

In an embodiment, a hydrogel composition comprises a crosslinked glycosaminoglycan polymer where the crosslinked glycosaminoglycan polymer is present in an amount sufficient to improve a skin condition as disclosed herein. In aspect of this embodiment, a composition comprises a crosslinked chondroitin sulfate polymer, a crosslinked dermatan sulfate polymer, a crosslinked keratan sulfate polymer, a crosslinked heparan polymer, a crosslinked heparan sulfate polymer, or a crosslinked hyaluronan polymer. In other aspects of this embodiment, a composition comprises a crosslinked glycosaminoglycan where the crosslinked glycosaminoglycan represents, e.g., about 1% by weight, about 2% by weight, about 3% by weight, about 4% by weight, about 5% by weight, about 6% by weight, about 7% by weight, about 8% by weight, or about 9%, or about 10% by weight, of the total glycosaminoglycan present in the composition. In yet other aspects of this embodiment, a composition comprises a crosslinked glycosaminoglycan where the crosslinked glycosaminoglycan represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total glycosaminoglycan present in the composition. In still other aspects of this embodiment, a composition comprises a crosslinked glycosaminoglycan where the crosslinked glycosaminoglycan represents, e.g., about 0% to about 20% by weight, about 1% to about 17% by weight, about 3% to about 15% by weight, or about 5% to about 10% by weight, for example, about 11% by weight, about 15% by weight or about 17% by weight, of the total glycosaminoglycan present in the composition.

In aspects of this embodiment, a hydrogel composition comprises a crosslinked glycosaminoglycan where the crosslinked glycosaminoglycan is present at a concentration of, e.g., about 2 mg/g, about 3 mg/g, about 4 mg/g, about 5 mg/g, about 6 mg/g, about 7 mg/g, about 8 mg/g, about 9 mg/g, about 10 mg/g, about 11 mg/g, about 12 mg/g, about 13 mg/g, about 13.5 mg/g, about 14 mg/g, about 15 mg/g, about 16 mg/g, about 17 mg/g, about 18 mg/g, about 19 mg/g, or about 20 mg/g. In other aspects of this embodiment, a composition comprises a crosslinked glycosaminoglycan where the crosslinked glycosaminoglycan is present at a concentration of, e.g., at least 1 mg/g, at least 2 mg/g, at least 3 mg/g, at least 4 mg/g, at least 5 mg/g, at least 10 mg/g, at least 15 mg/g, at least 20 mg/g, or at least 25 mg/g, or about 40 mg/g. In yet other aspects of this embodiment, a composition comprises a crosslinked glycosaminoglycan where the crosslinked glycosaminoglycan is present at a concentration of, e.g., at most 1 mg/g, at most 2 mg/g, at most 3 mg/g, at most 4 mg/g, at most 5 mg/g, at most 10 mg/g, at most 15 mg/g, at most 20 mg/g, at most 25 mg/g, or at most 40 mg/g. In still other aspects of this embodiment, a composition comprises a crosslinked glycosaminoglycan where the crosslinked glycosaminoglycan is present at a concentration of, e.g., about 7.5 mg/g to about 19.5 mg/g, about 8.5 mg/g to about 18.5 mg/g, about 9.5 mg/g to about 17.5 mg/g, about 10.5 mg/g to about 16.5 mg/g, about 11.5 mg/g to about 15.5 mg/g, or about 12.5 mg/g to about 14.5 mg/g, up to about 40 mg/g.

Aspects of the present specification provide, in part, a hydrogel composition comprising hyaluronan polymers of low molecular weight, hyaluronan polymers of high molecular weight, or hyaluronan polymers of both low and high molecular weight. As used herein, the term "high molecular weight" when referring to "hyaluronan" refers to hyaluronan polymers having a mean molecular weight of 1,000,000 Da or greater. Non-limiting examples of a high molecular weight hyaluronan polymers include hyaluronan polymers about 1,500,000 Da, about 2,000,000 Da, about 2,500,000 Da, about 3,000,000 Da, about 3,500,000 Da, about 4,000,000 Da, about 4,500,000 Da, and about 5,000,000 Da. As used herein, the term "low molecular weight" when referring to "hyaluronan" refers to hyaluronan polymers having a mean molecular weight of less than 1,000,000 Da. Non-limiting examples of a low molecular weight hyaluronan polymers include hyaluronan polymers of about 200,000 Da, about 300,000 Da, about 400,000 Da, about 500,000 Da, about 600,000 Da, about 700,000 Da, of about 800,000 Da, and about 900,000 Da.

In an embodiment, a composition comprises crosslinked hyaluronan polymers of low molecular weight. In aspects of this embodiment, a composition comprises crosslinked hyaluronan polymers having a mean molecular weight of, e.g., about 100,000 Da, about 200,000 Da, about 300,000 Da, about 400,000 Da, about 500,000 Da, about 600,000 Da, about 700,000 Da, about 800,000 Da, or about 900,000 Da. In yet other aspects of this embodiment, a composition comprises crosslinked hyaluronan polymers having a mean molecular weight of, e.g., at most 100,000 Da, at most 200,000 Da, at most 300,000 Da, at most 400,000 Da, at most 500,000 Da, at most 600,000 Da, at most 700,000 Da, at most 800,000 Da, at most 900,000 Da, or at most 950,000. In still other aspects of this embodiment, a composition comprises crosslinked hyaluronan polymers having a mean molecular weight of, e.g., about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In another embodiment, a composition comprises crosslinked hyaluronan polymers of high molecular weight. In aspects of this embodiment, a composition comprises a crosslinked hyaluronan polymers having a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a composition comprises a crosslinked hyaluronan polymers having a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a composition comprises a crosslinked hyaluronan polymers having a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da.

In yet another embodiment, a composition comprises a crosslinked hyaluronan polymers where the crosslinked hyaluronan polymers comprise a combination of both high molecular weight hyaluronan polymers and low molecular weight hyaluronan polymers, in various ratios. In aspects of this embodiment, a composition comprises a crosslinked hyaluronan polymers where the crosslinked hyaluronan polymers comprises a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel composition comprising a crosslinked glycosaminoglycan polymer having a degree of crosslinking. As used herein, the term "degree of crosslinking" refers to the percentage of glycosaminoglycan polymer monomeric units, such as, e.g., the disaccharide monomer units of hyaluronan that are bound to a cross-linking agent. The degree of crosslinking is expressed as the percent weight ratio of the crosslinking agent to glycosaminoglycan.

Aspects of the present specification provide, in part, a hydrogel composition comprising an uncrosslinked glycosaminoglycan polymer. As used herein, the term "uncrosslinked" refers to a lack of intermolecular bonds joining the individual glycosaminoglycan polymer molecules, or monomer chains. As such, an uncrosslinked glycosaminoglycan polymer is not linked to any other glycosaminoglycan polymer by an intermolecular bond. In aspects of this embodiment, a composition comprises an uncrosslinked chondroitin sulfate polymer, an uncrosslinked dermatan sulfate polymer, an uncrosslinked keratan sulfate polymer, an uncrosslinked heparan polymer, an uncrosslinked heparan sulfate polymer, or an uncrosslinked hyaluronan polymer. Uncrosslinked glycosaminoglycan polymers are water soluble and generally remain fluid in nature. As such, uncross-linked glycosaminoglycan polymers are often mixed with a glycosaminoglycan polymer-based hydrogel composition as a lubricant to facilitate the extrusion process of the composition through a fine needle.

In an embodiment, a composition comprises an uncrosslinked glycosaminoglycan polymer where the uncrosslinked glycosaminoglycan polymer is present in an amount sufficient to improve a skin condition as disclosed herein. In aspects of this embodiment, a composition comprises an uncrosslinked glycosaminoglycan where the uncrosslinked glycosaminoglycan is present at a concentration of, e.g., about 2 mg/g, about 3 mg/g, about 4 mg/g, about 5 mg/g, about 6 mg/g, about 7 mg/g, about 8 mg/g, about 9 mg/g, about 10 mg/g, about 11 mg/g, about 12 mg/g, about 13 mg/g, about 13.5 mg/g, about 14 mg/g, about 15 mg/g, about 16 mg/g, about 17 mg/g, about 18 mg/g, about 19 mg/g, about 20 mg/g, about 40 mg/g, or about 60 mg/g. In other aspects of this embodiment, a composition comprises an uncrosslinked glycosaminoglycan where the uncrosslinked glycosaminoglycan is present at a concentration of, e.g., at least 1 mg/g, at least 2 mg/g, at least 3 mg/g, at least 4 mg/g, at least 5 mg/g, at least 10 mg/g, at least 15 mg/g, at least 20 mg/g, at least 25 mg/g at least 35 mg/g, or at least 40 mg/g. In yet other aspects of this embodiment, a composition comprises an uncrosslinked glycosaminoglycan where the uncrosslinked glycosaminoglycan is present at a concentration of, e.g., at most 1 mg/g, at most 2 mg/g, at most 3 mg/g, at most 4 mg/g, at most 5 mg/g, at most 10 mg/g, at most 15 mg/g, at most 20 mg/g, or at most 25 mg/g. In still other aspects of this embodiment, a composition comprises an uncrosslinked glycosaminoglycan where the uncrosslinked glycosaminoglycan is present at a concentration of, e.g., about 1 mg/g to about 60 mg/g, about 10 mg/g to about 40 mg/g, about 7.5 mg/g to about 19.5 mg/g, about 8.5 mg/g to about 18.5 mg/g, about 9.5 mg/g to about 17.5 mg/g, about 10.5 mg/g to about 16.5 mg/g, about 11.5 mg/g to about 15.5 mg/g, or about 12.5 mg/g to about 14.5 mg/g.

In an embodiment, a composition comprises uncrosslinked hyaluronan polymers of low molecular weight. In aspects of this embodiment, a composition comprises a uncrosslinked hyaluronan having a mean molecular weight of, e.g., about 100,000 Da, about 200,000 Da, about 300,000 Da, about 400,000 Da, about 500,000 Da, about 600,000 Da, about 700,000 Da, about 800,000 Da, or about 900,000 Da. In yet other aspects of this embodiment, a composition comprises uncrosslinked hyaluronan polymers having a mean molecular weight of, e.g., at most 100,000 Da, at most 200,000 Da, at most 300,000 Da, at most 400,000 Da, at most 500,000 Da, at most 600,000 Da, at most 700,000 Da, at most 800,000 Da, at most 900,000 Da, or at most 950,000. In still other aspects of this embodiment, a composition comprises uncrosslinked hyaluronan polymers having a mean molecular weight of, e.g., about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In another embodiment, a composition comprises uncrosslinked hyaluronan polymers of high molecular weight. In aspects of this embodiment, a composition comprises an uncrosslinked hyaluronan having a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In other aspects of this embodiment, a composition comprises an uncrosslinked hyaluronan polymers having a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In yet other aspects of this embodiment, a composition comprises an uncrosslinked hyaluronan polymers having a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da. In still other aspects, a composition comprises an uncrosslinked hyaluronan polymers having a mean molecular weight of, e.g., greater than 2,000,000 Da and less than about 3,000,000 Da, greater than 2,000,000 Da and less than about 3,500,000 Da, greater than 2,000,000 Da and less than about 4,000,000 Da, greater than 2,000,000 Da and less than about 4,500,000 Da, greater than 2,000,000 Da and less than about 5,000,000 Da.

In another embodiment, a composition comprises uncrosslinked hyaluronan polymers where the uncrosslinked hyaluronan comprises a combination of both high molecular weight hyaluronan polymers and low molecular weight hyaluronan polymers, in various ratios. In aspects of this embodiment, a composition comprises an uncrosslinked hyaluronan polymers where the uncrosslinked hyaluronan polymers comprises a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel composition comprising a substantially uncrosslinked glycosaminoglycan polymer. As sued herein, the term "substantially uncrosslinked" refers to the presence of uncrosslinked glycosaminoglycan polymers in a composition disclosed herein at a level of at least 90% by weight of the composition, with the remaining at most 10% by weight of the composition being comprised of other components including crosslinked glycosaminoglycan polymers. In aspects of this embodiment, a composition comprises a substantially uncrosslinked chondroitin sulfate polymer, a substantially uncrosslinked dermatan sulfate polymer, a substantially uncrosslinked keratan sulfate polymer, a substantially uncrosslinked heparan polymer, a substantially uncrosslinked heparan sulfate polymer, or a substantially uncrosslinked hyaluronan polymer. In other aspects of this embodiment, a composition comprises an uncrosslinked glycosaminoglycan where the uncrosslinked glycosaminoglycan represents, e.g., about 90% or more by weight, about 91% or more by weight, about 92% or more by weight, about 93% or more by weight, about 94% or more by weight, about 95% or more by weight, about 96% or more by weight, about 97% or more by weight, about 98% or more by weight, or about 99% or more, or about 100% by weight, of the total glycosaminoglycan present in the composition. In yet other aspects of this embodiment, a composition comprises an uncrosslinked glycosaminoglycan where the uncrosslinked glycosaminoglycan represents, e.g., about 90% to about 100% by weight, about 93% to about 100% by weight, about 95% to about 100% by weight, or about 97% to about 100% by weight, of the total glycosaminoglycan present in the composition.

Aspects of the present specification provide, in part, a hydrogel composition that is essentially free of a crosslinked glycosaminoglycan polymer. As used herein, the term "essentially free" (or "consisting essentially of") refers to a composition where only trace amounts of cross-linked matrix polymers can be detected. In an aspect of this embodiment, a composition comprises a chondroitin sulfate that is essentially free of a crosslinked chondroitin sulfate polymer, a dermatan sulfate essentially free of a crosslinked dermatan sulfate polymer, a keratan sulfate essentially free of a crosslinked keratan sulfate polymer, a heparan essentially free of a crosslinked heparan polymer, a heparan sulfate essentially free of a crosslinked heparan sulfate polymer, or a hyaluronan sulfate essentially free of a crosslinked hyaluronan polymer.

Aspects of the present specification provide, in part, a hydrogel composition that is entirely free of a crosslinked glycosaminoglycan polymer. As used herein, the term "entirely free" refers to a composition that within the detection range of the instrument or process being used, crosslinked glycosaminoglycan polymers cannot be detected or its presence cannot be confirmed. In an aspect of this embodiment, a composition comprises a chondroitin sulfate that is entirely free of a crosslinked chondroitin sulfate polymer, a dermatan sulfate entirely free of a crosslinked dermatan sulfate polymer, a keratan sulfate entirely free of a crosslinked keratan sulfate polymer, a heparan entirely free of a crosslinked heparan polymer, a heparan sulfate entirely free of a crosslinked heparan sulfate polymer, or a hyaluronan sulfate entirely free of a crosslinked hyaluronan polymer.

Aspects of the present specification provide, in part, a hydrogel composition comprising a ratio of crosslinked glycosaminoglycan polymer and uncrosslinked glycosaminoglycan polymer. This ratio of crosslinked and uncrosslinked glycosaminoglycan polymer is also known as the gel:fluid ratio. Any gel:fluid ratio is useful in making the compositions disclosed herein with the proviso that such ratio produces a composition disclosed herein that improves a skin condition as disclosed herein. Non-limiting examples of gel:fluid ratios include 100:0, 98:2, 90:10, 75:25, 70:30, 60:40, 50:50, 40:60, 30:70, 25:75, 10:90; 2:98, and 0:100.

In aspects of this embodiment, a composition comprises a crosslinked glycosaminoglycan polymer and an uncrosslinked glycosaminoglycan polymer where the gel:fluid ratio is, e.g., about 0:100, about 1:99, about 2:98, about 3:97, about 4:96, about 5:95, about 6:94, about 7:93, about 8:92, about 9:91, or about 10:90. In other aspects of this embodiment, a composition comprises a crosslinked glycosaminoglycan polymer and an uncrosslinked glycosaminoglycan polymer where the gel:fluid ratio is, e.g., at most 1:99, at most 2:98, at most 3:97, at most 4:96, at most 5:95, at most 6:94, at most 7:93, at most 8:92, at most 9:91, or at most 10:90. In yet other aspects of this embodiment, a composition comprises a crosslinked glycosaminoglycan polymer and an uncrosslinked glycosaminoglycan polymer where the gel:fluid ratio is, e.g., about 0:100 to about 3:97, about 0:100 to about 5:95, or about 0:100 to about 10:90.

In other aspects of this embodiment, a composition comprises a crosslinked glycosaminoglycan polymer and an uncrosslinked glycosaminoglycan polymer where the gel:fluid ratio is, e.g., about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 98:2, or about 100:0. In yet other aspects of this embodiment, a composition comprises a crosslinked glycosaminoglycan polymer and an uncrosslinked glycosaminoglycan polymer where the gel:fluid ratio is, e.g., at most 15:85, at most 20:80, at most 25:75, at most 30:70, at most 35:65, at most 40:60, at most 45:55, at most 50:50, at most 55:45, at most 60:40, at most 65:35, at most 70:30, at most 75:25, at most 80:20, at most 85:15, at most 90:10, at most 95:5, at most 98:2, or at most 100:0. In still other aspects of this embodiment, a composition comprises a crosslinked glycosaminoglycan polymer and an uncrosslinked glycosaminoglycan polymer where the gel:fluid ratio is, e.g., about 10:90 to about 70:30, about 15:85 to about 70:30, about 10:90 to about 55:45, about 80:20 to about 95:5, about 90:10 to about 100:0, about 75:25 to about 100:0, or about 60:40 to about 100:0.

Aspects of the present specification provide, in part, a hydrogel composition disclosed herein may further and optionally comprise another agent or combination of agents that provide a beneficial effect when the composition is administered to an individual. Such beneficial agents include, without limitation, an antioxidant, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, or a moisturizing agent.

Aspects of the present specification provide, in part, a hydrogel composition disclosed herein that may optionally comprise an anesthetic agent. An anesthetic agent is preferably a local anesthetic agent, i.e., an anesthetic agent that causes a reversible local anesthesia and a loss of nociception, such as, e.g., aminoamide local anesthetics and aminoester local anesthetics. The amount of an anesthetic agent included in a composition disclosed herein is an amount effective to mitigate pain experienced by an individual upon administration of the composition. As such, the amount of an anesthetic agent included in a composition disclosed in the present specification is between about 0.1% to about 5% by weight of the total composition. Non-limiting examples of anesthetic agents include lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof. Non-limiting examples of aminoester local anesthetics include procaine, chloroprocaine, cocaine, cyclomethycaine, dimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, and trimecaine. A composition disclosed herein may comprise a single anesthetic agent or a plurality of anesthetic agents. A non-limiting example of a combination local anesthetic is lidocaine/prilocaine (EMLA).

Thus in an embodiment, a composition disclosed herein comprises an anesthetic agent and salts thereof. In aspects of this embodiment, a composition disclosed herein comprises an aminoamide local anesthetic and salts thereof or an aminoester local anesthetic and salts thereof. In other aspects of this embodiment, a composition disclosed herein comprises procaine, chloroprocaine, cocaine, cyclomethycaine, dimethocaine, propoxycaine, procaine, proparacaine, tetracaine, or salts thereof, or any combination thereof. In yet other aspects of this embodiment, a composition disclosed herein comprises articaine, bupivacaine, cinchocaine, etidocaine, levobupivacaine, lidocaine, mepivacaine, piperocaine, prilocaine, ropivacaine, trimecaine, or salts thereof, or any combination thereof. In still other aspects of this embodiment, a composition disclosed herein comprises a lidocaine/prilocaine combination.

In other aspects of this embodiment, a composition disclosed herein comprises an anesthetic agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an anesthetic agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an anesthetic agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an anesthetic agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a composition disclosed herein does not comprise an anesthetic agent.

Aspects of the present specification provide, in part, a hydrogel composition disclosed herein that may optionally comprise an anti-oxidant agent. The amount of an anti-oxidant agent included in a composition disclosed herein is an amount effective to reduce or prevent degradation of a composition disclosed herein, such as, e.g., enzymatic degradation and/or chemical degradation of the composition. As such, the amount of an anti-oxidant agent included in a composition disclosed herein is between about 0.1% to about 10% by weight of the total composition. Non-limiting examples of antioxidant agents include a polyol, a flavonoid, a phytoalexin, an ascorbic acid agent, a tocopherol, a tocotrienol, a lipoic acid, a melatonin, a carotenoid, an analog or derivative thereof, and any combination thereof. A composition disclosed herein may comprise a single antioxidant agent or a plurality of antioxidant agents, a retinol, coenzyme, idebenone, allopurinol, glutathione, sodium selenite.

Aspects of the present specification provide, in part, a hydrogel composition disclosed herein that may optionally comprise a polyol. As used herein, the term "polyol" is synonymous with "sugar alcohol," "polyhydric alcohol," and "polyalcohol" and refers to a hydrogenated form of carbohydrate, whose carbonyl group (aldehyde or ketone, reducing sugar) has been reduced to a primary or secondary hydroxyl group (hence the alcohol), such as, e.g., mannitol from mannose, xylitol from xylose, and lactitol from lactulose. Polyols have the general formula $H(HCHO)_n+1H$. Both monosaccharides and disaccharides can form polyols; however, polyols derived from disaccharides are not entirely hydrogenated because only one aldehyde group is available for reduction. Non-limiting examples of polyols include glycerol, erythritol, threitol, arabitol, erythritol, ribitol, xylitol, galactitol (or dulcitol), glucitol (or sorbitol), iditol, inositol, mannitol, isomalt, lactitol, maltitol, and polyglycitol. Other non-limiting examples of polyols can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

Aspects of the present specification provide, in part, a hydrogel composition disclosed herein that may optionally comprise a flavonoid (Table 2). A flavonoid (or bioflavonoid) refers to the class of polyphenolic ketone-containing and non-ketone-containing secondary metabolites found in plants that are well known to have diverse beneficial biochemical and antioxidant effects. Non-limiting examples of flavonoids include C-methylated flavonoids, O-methylated flavonoids, isoflavonoids, neoflavonoids, flavonolignans, furanoflavonoids, pyranoflavonoids, methylenedioxyflavonoids, prenylated flavonoids, aurones, flavones, flavonols, flavanones, flavanonols, flavan-3-ols, flavan-4-ols, leucoanthocyanidin (flavan-3,4-diols), anthocyanidins, and tannins. It is understood that these and other substances known in the art of pharmacology can be included in a composition disclosed in the present specification. See for example, Remington's *Pharmaceutical Sciences* Mac Publishing Company, Easton, Pa. $16^{th}$ Edition 1980.

Aurones are compounds derived from 2-benzylidene-1-benzofuran-3-one. Non-limiting examples of aurones include 4,5,6-trihydroxy-aurone, aureusidin, hispidol, leptosidin, maritimetin, and sulfuretin.

Three major classes of ketone-containing flavonoids are flavones, compounds derived from 2-phenylchromen-4-one (2-phenyl-1,4-benzopyrone); isoflavones, compounds derived from 3-phenylchromen-4-one (3-phenyl-1,4-benzopyrone); and neoflavones, compounds derived from 4-phenylcoumarine (4-phenyl-1,2-benzopyrone)(Table 2). Flavones are themselves divided into four groups based on the presence or absence of 3-hydroxyl 2,3-dihydro functional groups: flavones, compounds derived from 2-phenylchromen-4-one lack both functional groups; flavonols (3-hydroxyflavone), compounds derived from 3-hydroxy-2-phenylchromen-4-one have the 3-hydroxyl group, but lack the 2,3-dihydro group; flavanones, compounds derived from 2,3-dihydro-2-phenylchromen-4-one have the 2,3-dihydro group, but lack the 3-hydroxyl group; and flavanonols (3-hydroxyflavanone or 2,3-dihydroflavonol), compounds derived from 3-hydroxy-2,3-dihydro-2-phenylchromen-4-one have both functional groups.

Non-limiting examples of flavones include acacetin, apiin, apigenin, apigetrin, artoindonesianin P, baicalein, baicalin, chrysin, cynaroside, diosmetin, diosmin, eupatilin, flavoxate, 6-hydroxyflavone, genkwanin, hidrosmin, luteolin, nepetin, nepitrin (nepetin 7-glucoside), nobiletin, orientin (isoorientin), oroxindin, oroxylin A, rhoifolin, scutellarein, scutellarin, tangeritin, techtochrysin, tetuin, tricin, veronicastroside, vitexin (isovitexin), and wogonin. Non-limiting examples of flavonols include 3-hydroxyflavone, azaleatin, fisetin, galangin, gossypetin, kaempferide, kaempferol, isorhamnetin, morin, myricetin, natsudaidain, pachypodol, quercetin, rhamnazin, rhamnetin, and sophorin. Non-limiting examples of flavanones include butin, eriodictyol, hesperetin, hesperidin, homoeriodictyol, isosakuranetin, naringenin, naringin, pinocembrin, poncirin, sakuranetin, sakuranin, and sterubin. Non-limiting examples of flavanonols include taxifolin (dihydroquercetin), and aromadedrin (dihydrokaempferol).

Isoflavonoids include isoflavones and isoflavanes (Table 2). Non-limiting examples of isoflavonoids include alpinumisoflavone, anagyroidisoflavone A and B, calycosin, daidzein, daidzin, derrubone, di-O-methylalpinumisoflavone, formononetin, genistein, genistin, glycitein, ipriflavone, irigenin, iridin, irilone, 4'-methyl-alpinumisoflavone, 5-O-methylgenistein, luteone, ononin, orobol, pratensein, prunetin, pseudobaptigenin, psi-tectorigenin, puerarin, retusin, tectoridin, tectorigenin, and wighteone.

Neoflavonoids include 4-arylcoumarins (neoflavones), 4-arylchromanes, dalbergiones and dalbergiquinols (Table 2). Neoflavones are compounds derived from 4-phenylcoumarin (or 4-Aryl-coumarin); neoflavenes compounds derived from 4-phenylchromen. Non-limiting examples of neoflavonoids include calophyllolide, coutareagenin, dalbergichromene, dalbergin, and nivetin.

Non-ketone-containing flavonoids, include flavan-3-ols and catechins. Flavan-3-ols (flavanols) are a class of flavonoids derived from 2-phenyl-3,4-dihydro-2H-chromen-3-ol skeleton. Catechin possesses two benzene rings (called the A- and B-rings) and a dihydropyran heterocycle (the C-ring) with an hydroxyl group on carbon 3. The A ring is similar to a resorcinol moiety while the B ring is similar to a catechol moiety. There are two chiral centers on the molecule on carbons 2 and 3. It has therefore four diastereoisomers. Two of the isomers are in trans configuration and are called catechin and the other two are in cis configuration and are called epicatechin. Non-limiting examples of non-ketone-containing flavonoids include afzelechin, arthromerin A, arthromerin B, catechin, epicatechin, epigallocatechin, epicatechin gallate, epigallocatechin gallate, epigallocatechin gallate, epiafzelechin, fisetinidol, gallocatechin, gallocatechin gallate, guibourtinidol, meciadanol (3-O-methylcatechin), mesquitol, propyl gallate, robinetinidol, and thearubigin.

Flavan-4-ols (3-deoxyflavonoids) are flavone-derived alcohols derived from 2-phenylchroman-4-ol. Non-limiting examples of flavan-4-ols include apiforol and luteoforol.

Leucoanthocyanidin (flavan-3,4-diols) are compounds derived from 2-phenyl-3,4-dihydro-2H-chromene-3,4-diol. Non-limiting examples of flavan-3,4-diols include leucocyanidin, leucodelphinidin, leucomalvidin, leucopelargonidin, leucopeonidin, leucorobinetinidin, and melacacidin.

Anthocyanidins are compounds derived from 2-phenylchromenylium. Non-limiting examples of anthocyanidins include antirrhinin, apigeninidin, aurantinidin, capensinidin, chrysanthenin, columnidin, commelinin, cyanidin, 6-hydroxycyanidin, cyanidin-3-(di-p-coumarylglucoside)-5-glucoside, cyanosalvianin, delphinidin, diosmetinidin, europinidin, fisetinidin, gesneridin, guibourtinidin, hirsutidin, luteolinidin, malvidin, 5-desoxy-malvidin, malvin, myrtillin, oenin, peonidin, 5-desoxy-peonidin, pelargonidin, petunidin, primulin, protocyanin, protodelphin, pulchellidin, pulchellidin 3-glucoside, pulchellidin 3-rhamnoside, robinetinidin, rosinidin, tricetinidin, tulipanin, and violdelphin.

Tannins are compounds derived from 2-phenylchromenylium. There are three major classes of tannins: hydrolyzable tannins; non-hydrolyzable tannins (condensed tannins; proanthocyanidins); and pseudotannins.

Hydrolyzable tannins are themselves divided into four groups: oligomer tannins including aglycone tannins and glycoside tannins; ellagitannins; gallotannins, and unclassified tannins. Non-limiting examples of aglycone tannins include ellagic acid, gallagic acid, and gallic acid. Non-limiting examples of glycoside tannins include glucose, quinic acid, and shikimic acid. Non-limiting examples of ellagitannins include castalagin (vescalagin), castalin, casuarictin, casuariin, casuarinin, cornusiin E, grandinin, pedunculagin, punicacortein C, punigluconin, punicalagin, punicalagin alpha, punicalin, 2-O-galloyl-punicalin, stachyurin, strictinin, and tellimagrandin II. Non-limiting examples of gallotannins include corilagin, galloyl glucose, digalloyl glucose, trigalloyl glucose, tetragalloyl glucose, pentagalloyl glucose, hexagalloyl glucose, heptagalloyl glucose, octagalloyl glucose, and tannic acid. Non-limiting examples of unclassified tannins include acutissimin A, acutissimin B, chebulagic acid, chebulinic acid, cinnamtannin B1, combreglutinin, geraniin, granatin B, roburin A, roburin B, roburin C, roburin D, roburin E, stachyurin, tercatin, terflavins A, terflavins B, tergallagin, vescalin, 1,3,4-tri-O-galloylquinic acid, 3,5-di-O-galloyl-shikimic acid, and 3,4,5-tri-O-galloylshikimic acid.

Condensed tannins (proanthocyanidins) are essentially polymer chains of flavonoids such as catechins. Non-limiting examples of condensed tannins include proanthocyanidin, prodelphinidin, profisetinidin, proguibourtinidin, and prorobinetidin.

TABLE 2

| Flavonoids | | |
|---|---|---|
| Flavonoids | Base compound | Examples |
| Aurones | 2-benzylidene-1-benzofuran-3-one | 4,5,6-trihydroxy-aurone, aureusidin, hispidol, leptosidin, maritimetin, and sulfuretin |
| Flavones | 2-phenylchromen-4-one | acacetin, apiin, apigenin, apigetrin, artoindonesianin P, baicalein, baicalin, chrysin, cynaroside, diosmetin, diosmin, eupatilin, flavoxate, 6-hydroxyflavone, genkwanin, hidrosmin, luteolin, nepetin, nepitrin, nobiletin, orientin, oroxindin, oroxylin A, rhoifolin, scutellarein, scutellarin, tangeritin, techtochrysin, tetuin, tricin, veronicastroside, vitexin, wogonin |
| Flavonols | 3-hydroxy-2-phenylchromen-4-one | 3-hydroxyflavone, azaleatin, fisetin, galangin, gossypetin, kaempferide, kaempferol, isorhamnetin, morin, myricetin, natsudaidain, pachypodol, quercetin, rhamnazin, rhamnetin, sophorin |
| Flavanones | 2,3-dihydro-2-phenylchromen-4-one | butin, eriodictyol, hesperetin, hesperidin, homoeriodictyol, isosakuranetin, naringenin, naringin, pinocembrin, poncirin, sakuranetin, sakuranin, sterubin |
| Flavanonols | 3-hydroxy-2,3-dihydro-2-phenylchromen-4-one | aromadedrin, taxifolin |
| Isoflavones | 3-phenylchromen-4-one | alpinumisoflavone, anagyroidisoflavone A and B, calycosin, daidzein, daidzin, derrubone, di-O-methylalpinumisoflavone, formononetin, genistein, genistin, glycitein, ipriflavone, irigenin, iridin, irilone, 4'-methyl-alpinumisoflavone, 5-O-methylgenistein, luteone, ononin, orobol, pratensein, |

TABLE 2-continued

Flavonoids

| Flavonoids | Base compound | Examples |
|---|---|---|
| Isoflavenes | 3-phenylchroman | prunetin, pseudobaptigenin, psi-tectorigenin, puerarin, retusin, tectoridin, tectorigenin, wighteone lonchocarpane, laxiflorane |
| Neoflavones | 4-phenylcoumarine | calophyllolide |
| Neoflavenes | 4-phenylchromen | dalbergichromene |
| Flavan-3-ols | 2-phenyl-3,4-dihydro-2H-chromen-3-ol | arthromerin A, arthromerin B, fisetinidol, guibourtinidol, meciadanol (3-O-methylcatechin), mesquitol, robinetinidol, thearubigin. |
| Catechins | (2R,3S)-2-(3,4-dihydroxyphenyl)-3,4-dihydro-2H-chromene-3,5,7-triol | (+)-catechin (2R-3S), (−)-catechin (2S-3R), (−)-Epicatechin (2R-3R), (+)-epicatechin (2S-3S) |
| Flavan-4-ols | 2-phenylchroman-4-ol | apiforol, luteoforol |
| Flavan-3,4-diols | 2-phenyl-3,4-dihydro-2H-chromene-3,4-diol | leucocyanidin, leucodelphinidin, leucomalvidin, leucopelargonidin, leucopeonidin, leucorobinetinidin, melacacidin |
| Anthocyanidins | 2-phenylchromenylium | antirrhinin, apigeninidin, aurantinidin, capensinidin, chrysanthenin, columnidin, commelinin, cyanidin, 6-hydroxycyanidin, cyanidin-3-(di-p-coumarylglucoside)-5-glucoside, cyanosalvianin, delphinidin, diosmetinidin, europinidin, fisetinidin, gesneridin, guibourtinidin, hirsutidin, luteolinidin, malvidin, 5-desoxy-malvidin, malvin, myrtillin, oenin, peonidin, 5-desoxy-peonidin, pelargonidin, petunidin, primulin, protocyanin, protodelphin, pulchellidin, pulchellidin 3-glucoside, pulchellidin 3-rhamnoside, robinetinidin, rosinidin, tricetinidin, tulipanin, violdelphin |
| Hydrolyzable tannins | gallic acid or ellagic acid | castalagin, castalin, casuarictin, casuariin, casuarinin, corilagin, cornusiin E, grandinin, galloyl glucose, digalloyl glucose, trigalloyl glucose, tetragalloyl glucose, pentagalloyl glucose, hexagalloyl glucose, heptagalloyl glucose, octagalloyl glucose, pedunculagin, punicacortein C, punigluconin, punicalagin, punicalagin alpha, punicalin, 2-O-galloyl-punicalin, stachyurin, strictinin, tannic acid, tellimagrandin II |
| Condensed tannins | polymer chains of flavonoid units | proanthocyanidin, prodelphinidin, profisetinidin, proguibourtinidin, prorobinetidin |

Aspects of the present specification provide, in part, a hydrogel composition disclosed herein that may optionally comprise a phytoalexin. A phytoalexin refers to the class of antimicrobial molecules with antioxidant effects synthesized de novo by plants in response to an incompatible pathogen infection. Non-limiting examples of phytoalexins include resveratrol (3,5,4'-trihydroxy-trans-stilbene), allixin (3-hydroxy-5-methoxy-6-methyl-2-pentyl-4H-pyran-4-one), glyceollin, phaseolin, and medicarpin.

Aspects of the present specification provide, in part, a hydrogel composition disclosed herein that may optionally comprise an ascorbic acid agent. Ascorbic acid (Vitamin C), (5R)-[(1S)-1,2-dihydroxyethyl]-3,4-dihydroxyfuran-2(5H)-one, is a monosaccharide oxidation-reduction (redox) catalyst found in both animals and plants that reduces, and thereby neutralize, reactive oxygen species such as hydrogen peroxide. Ascorbic acid also interconverts into two unstable ketone tautomers by proton transfer, although it is the most stable in the enol form. The proton of the hydroxyl of the enol is removed. Then a pair of electrons from the resulting oxide anion pushes down to form the ketone at the 2 or 3 position and the electrons from the double bond move to the 3 or 2 position, respectively, forming the carbanion, which picks up the proton resulting in two possible forms: 1-carboxyl-2-ketone and 1-carboxyl-3-ketone. Non-limiting examples of ascorbic acid agents include ascorbic acid agents include ascorbic acid and sodium, potassium, and calcium salts of ascorbic acid, fat-soluble esters of ascorbic acid with long-chain fatty acids (ascorbyl palmitate or ascorbyl stearate), magnesium ascorbyl phosphate (MAP), sodium ascorbyl phosphate (SAP), and ascorbic acid 2-glucoside (AA2G™) disodium ascorbyl sulfate, vitagen.

Aspects of the present specification provide, in part, a hydrogel composition disclosed herein that may optionally comprise a tocopherol and/or a tocotrienol. Tocopherols and tocotrienols comprise a group of antioxidant agents collectively referred to as Vitamin E. All feature a chromanol ring, with a hydroxyl group that can donate a hydrogen atom to reduce free radicals and a hydrophobic side chain which allows for penetration into biological membranes. Both the tocopherols and tocotrienols occur in alpha, beta, gamma and delta forms, determined by the number and position of methyl groups on the chromanol ring. The tocotrienols have the same methyl structure at the ring, but differ from the analogous tocopherols by the presence of three double bonds in the hydrophobic side chain. The unsaturation of the tails gives tocotrienols only a single stereoisomeric carbon (and thus two possible isomers per structural formula, one of which occurs naturally), whereas tocopherols have 3 centers (and eight possible stereoisomers per structural formula, one of which occurs naturally). In general, the unnatural 1-isomers of tocotrienols lack almost all vitamin activity, and half of the possible 8 isomers of the tocopherols (those with 2S chirality at the ring-tail junction) also lack vitamin activity. Of the stereoisomers which retain activity, increasing methylation, especially full methylation to the alpha-form, increases vitamin activity. Non-limiting examples of Vitamin E include tocopherols (like α-tocopherol, β-tocopherol, γ-tocopherol, and δ-tocopherol), tocopherols analogs and derivatives (like tocopheryl acetate, sodium tocopheryl phosphate (STP), polyoxyethanyl-α-tocopheryl sebacate, and tocopherol polyethylene glycol 1000 succinate (TPGS)), tocotrienols (like α-tocotrienol, β-tocotrienol, γ-tocotrienol, and δ-tocotrienol), tocotrienols analogs and derivatives.

Aspects of the present specification provide, in part, a hydrogel composition disclosed herein that may optionally comprise a lipoic acid (LA). Lipoic acid, (R)-5-(1,2-dithiolan-3-yl)pentanoic acid, is an organosulfur compound derived from octanoic acid that contains two vicinal sulfur atoms (at C6 and C8) attached via a disulfide bond and is thus considered to be oxidized (although either sulfur atom can exist in higher oxidation states). The carbon atom at C6 is chiral and the molecule exists as two enantiomers R-(+)-lipoic acid (RLA) and S-(−)-lipoic acid (SLA) and as a racemic mixture R/S-lipoic acid (R/S-LA). Only the R-(+)-enantiomer exists in nature and is an essential cofactor of four mitochondrial enzyme complexes.

Aspects of the present specification provide, in part, a hydrogel composition disclosed herein that may optionally comprise a melatonin. Melatonin, N-acetyl-5-methoxytryptamine, is a pervasive and powerful antioxidant found in animals, plants, and microbes.

Aspects of the present specification provide, in part, a hydrogel composition disclosed herein that may optionally comprise a carotenoid. Carotenoids are tetraterpenoid organic pigments that are naturally occurring in the chloroplasts and chromoplasts of plants and some other photosynthetic organisms like algae, some types of fungus some bacteria and at least one species of aphid. Structurally, tetraterpenes are synthesized biochemically from eight isoprene units resulting in a 40 carbon skeleton that can be terminated by hydrocarbon rings. There are over 600 known carotenoids; they are split into two classes, xanthophylls (which contain oxygen) and carotenes (which are purely hydrocarbons, and contain no oxygen).

Chemically, carotenes, including lycopenes, are polyunsaturated hydrocarbons containing 40 carbon atoms per molecule, variable numbers of hydrogen atoms, and no other elements. Some carotenes are terminated by hydrocarbon rings, on one or both ends of the molecule. Non-limiting examples of carotenes include α-carotene, β-carotene, γ-carotene, δ-carotene, ε-carotene, ζ-carotene, lycopene.

Xanthophylls hydrocarbons containing 40 carbon atoms per molecule that either contains hydroxyl groups and/or pairs of hydrogen atoms that are substituted by oxygen atoms. For this reason they are more polar than the purely hydrocarbon carotenes. Some xanthophylls are terminated by hydrocarbon rings, on one or both ends of the molecule. Non-limiting examples of xanthophylls include lutein, zeaxanthin, neoxanthin, violaxanthin, α-cryptoxanthin, and β-cryptoxanthin.

Aspects of the present specification provide, in part, a hydrogel composition disclosed herein that may optionally comprise a Vitamin A. Vitamin A includes retinol, retinal and retinoic acid and the different geometric isomers of retinol [(2E,4E,6E,8E)-3,7-dimethyl-9-(2,6,6-trimethylcyclohex-1-enyl)nona-2,4,6,8-tetraen-1-ol], retinal and retinoic acid resulting form either a trans or cis configuration of four of the five double bonds found in the polyene chain. Non-limiting examples of Vitamin A include retinol, retinal, retinoic acid, isomers of retinol, isomers of retinal, isomers of retinoic acid, tretinoin, isotretinoin, and retinyl palmitate.

In an embodiment, a composition disclosed herein comprises an antioxidant agent in an amount sufficient to reduce or prevent degradation of a glycosaminoglycan polymer. In aspects of this embodiment, a composition disclosed herein comprises a polyol, a flavonoid, a phytoalexin, an ascorbic acid agent, a tocopherol, a tocotrienol, a lipoic acid, a melatonin, a carotenoid, an analog or derivative thereof, or any combination thereof.

In other aspects of this embodiment, a composition disclosed herein comprises an antioxidant agent in an amount of, e.g., about 0.01% about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an antioxidant agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an antioxidant agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an antioxidant agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a composition disclosed herein does not comprise an antioxidant agent.

Aspects of the present specification provide, in part, a hydrogel composition disclosed herein that may optionally comprise a vasoconstrictor agent. The amount of a vasoconstrictor agent included in a composition disclosed herein is an amount effective to reduce, stop, and/or prevent bleeding experienced by an individual upon or after administration of the composition. Non-limiting examples of vasoconstrictor agents include al receptor agonists like 2-(1-naphthylmethyl)-2-imidazoline (naphazoline), (R)-4-(1-hydroxy-2-(methylamino)ethyl)benzene-1,2-diol (epinephrine), 2-amino-1-(2,5-dimethoxyphenyl)propan-1-ol (methoxamine), 4-[(1R,2S)-2-amino-1-hydroxypropyl]benzene-1,2-diol (methylnorepinephrine), 4-[(1R)-2-amino-1-hydroxyethyl]benzene-1,2-diol (norepinephrine), 3-(4,5-dihydro-1H-imidazol-2-ylmethyl)-2,4-dimethyl-6-tert-butyl-phenol (oxymetazoline), (R)-3-[-1-hydroxy-2-(methylamino)ethyl] phenol (phenylephrine or neo-synephrine), (R*,R*)-2-methylamino-1-phenylpropan-1-ol (pseudoephedrine), 4-[1-hydroxy-2-(methylamino)ethyl]phenol (synephrine or oxedrine), 2-[(2-cyclopropylphenoxy)methyl]-4,5-dihydro-1H-imidazole (cirazoline), 2-[(4-tert-butyl-2,6-dimethylphenyl)methyl]-4,5-dihydro-1H-imidazole (xylometazoline), analogs or derivatives thereof, and any combination thereof. A composition disclosed herein may comprise a single vasoconstrictor agent or a plurality of vasoconstrictor agents.

Thus in an embodiment, a composition disclosed herein comprises a vasoconstrictor agent. In aspects of this embodiment, a composition disclosed herein comprises an al receptor agonists. In aspects of this embodiment, a composition disclosed herein comprises naphazoline, epinephrine, methoxamine, methylnorepinephrine, norepinephrine, oxymetazoline, phenylephrine, pseudoephedrine, synephrine, cirazoline, xylometazoline, an analog or a derivative thereof, or any combination thereof.

In other aspects of this embodiment, a composition disclosed herein comprises a vasoconstrictor agent in an amount of, e.g., about 0.001%, about 0.01%, about 0.02%, about 0.03%, about 0.04%, about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0% by weight of the total composition. In yet other aspects, a composition disclosed herein comprises a vasoconstrictor agent in an amount of, e.g., at least about 0.01%, at least about 0.02%, at least about 0.03%, at least about 0.04%, at least about 0.1%, at least about 0.2%, at least about 0.3%, at least about 0.4%, at least about 0.5%, at least about 0.6%, at least about 0.7%, at least about 0.8% at least about 0.9%, at least about 1.0%, at least about 2.0%, at least about 3.0%, at least about 4.0%, or at least about 5.0% by weight of the total composition. In still other aspects, a composition disclosed herein comprises a vasoconstrictor agent in an amount of, e.g., at most about 0.1%, at most about 0.2%, at most about 0.3%, at most about 0.4%, at most about 0.5%, at most about 0.6%, at most about 0.7%, at most about 0.8% at most about 0.9%, at most about 1.0%, at most about 2.0%, at most about 3.0%, at most about 4.0%, or at most about 5.0% by weight of the total composition. In further aspects, a composition disclosed herein comprises a vasoconstrictor agent in an amount of, e.g., about 0.01% to about 0.1%, about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In a one embodiment, an injectable dermal filler composition is provided comprising a crosslinked hyaluronic acid-based polymer and phenylephrine present at a concentration of about 300 ppm to about 400 ppm. In some embodiments, the composition has been sterilized, for example, heat sterilized, in a process comprising a heat treatment of at least 100° C., and is substantially stable at room temperature for at least 12 months. The composition may further comprise lidocaine mixed with the crosslinked hyaluronic acid-based polymer and phenylephrine. The lidocaine may be present in an amount of between about 0.1% and about 1.0% w/w. For example, the lidocaine may be present in an amount of about 0.3% w/w.

In another embodiment, a composition disclosed herein does not comprise a vasoconstrictor agent.

Aspects of the present specification provide, in part, a hydrogel composition disclosed herein that may optionally comprise an antihemorrhagic agent. An antihemorrhagic agent includes hemostatic agents and antifibrinolytic agents. A hemostatic agent is a molecule that acts to reduce, stop, and/or prevent bleeding in the case of a ruptured blood vessel. One class of hemostatic agents is Vitamin K and its analogs or derivatives. Vitamin K and its 2-methyl-1,4-naphthoquinone derivatives is a group of lipophilic, hydrophobic vitamins that are needed for the posttranslational modification of certain proteins, mostly required for blood coagulation but also involved in metabolism pathways in bone and other tissue. The function of vitamin K in the cell is to convert glutamate in proteins to gamma-carboxyglutamate (gla). An antifibrinolytic agent is a molecule that acts to promote blood clot formation. Antifibrinolytics include aminocaproic acid (ε-aminocaproic acid) and tranexamic acid. These lysine-like drugs interfere with the formation of the fibrinolytic enzyme plasmin from its precursor plasminogen by plasminogen activators (primarily t-PA and u-PA). These drugs reversible block the lysine-binding sites of the enzymes or plasminogen and thus stop plasmin formation thereby preventing fibrinolysis and the breakdown of a blood clot. The amount of an antihemorrhagic agent included in a composition disclosed herein is an amount effective to reduce, stop, and/or prevent bleeding experienced by an individual upon or after administration of the composition. Ethamsylate (dicynene/dicynone) is another hemostatic agent. Non-limiting examples of antihemorrhagic agents include haemostatic agents like, chitosan, ethamsylate, desmopressin, a Vitamin K or a Vitamin K analog, such as, e.g., a Vitamin $K_1$ (phylloquinone, phytomenadione, or phytonadione), a Vitamin $K_2$ (menaquinone or menatetrenone), a Vitamin $K_3$ (menadione), a Vitamin $K_4$ (menadiol), a Vitamin $K_5$ (4-amino-2-methyl-1-naphthol hydrochloride), a Vitamin $K_6$, a Vitamin $K_7$, a Vitamin $K_8$, a Vitamin $K_9$, and a Vitamin $K_{10}$, antifibrinolytic agents like aminocaproic acid (ε-aminocaproic acid), tranexamic acid, serpins like aprotinin, α1-antitrypsin, C1-inhibitor, camostat, analogs or derivatives thereof, and any combination thereof. A composition disclosed herein may comprise a single antihemorrhagic agent or a plurality of antihemorrhagic agents.

Thus in an embodiment, a composition disclosed herein comprises an antihemorrhagic agent. In aspects of this embodiment, a composition disclosed herein comprises a hemostatic agent or an antifibrinolytic agent. In aspects of this embodiment, a composition disclosed herein comprises Vitamin K or a Vitamin K analog, such as, e.g., a Vitamin $K_1$, a Vitamin $K_2$, a Vitamin $K_3$, a Vitamin $K_4$, a Vitamin $K_5$, a Vitamin $K_6$, a Vitamin $K_7$, a Vitamin $K_8$, a Vitamin $K_9$, and a Vitamin $K_{10}$, ε-aminocaproic acid, tranexamic acid, serpins like aprotinin, α1-antitrypsin, C1-inhibitor, camostat, an analog or a derivative thereof, or any combination thereof.

In other aspects of this embodiment, a composition disclosed herein comprises antihemorrhagic agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises antihemorrhagic agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises antihemorrhagic agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises antihemorrhagic agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a composition disclosed herein does not comprise antihemorrhagic agent.

Aspects of the present specification provide, in part, a hydrogel composition disclosed herein that may optionally comprise an anti-itch agent. The amount of an anti-itch agent included in a composition disclosed herein is an amount effective to mitigate an itch response experienced by an individual upon administration of the composition. Non-limiting examples of anti-itch agents include methyl sulphonyl methane, sodium bicarbonate, calamine, allantoin, kaolin, peppermint, tea tree oil, camphor, menthol, hydrocortisone, analogs or derivatives thereof, and any combination thereof. A composition disclosed herein may comprise a single anti-itch agent or a plurality of anti-itch agents.

Thus in an embodiment, a composition disclosed herein comprises an anti-itch agent. In aspects of this embodiment, a composition disclosed herein comprises methyl sulphonyl methane, sodium bicarbonate, calamine, allantoin, kaolin, peppermint, tea tree oil, camphor, menthol, hydrocortisone, an analog or derivative thereof, or any combination thereof.

In other aspects of this embodiment, a composition disclosed herein comprises an anti-itch agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an anti-itch agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an anti-itch agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, or at most 10% by weight of the total composition. In further aspects, a composition disclosed herein comprises an anti-itch agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a composition disclosed herein does not comprise an anti-itch agent.

Aspects of the present specification provide, in part, a hydrogel composition disclosed herein that may optionally comprise an anti-cellulite agent. The amount of an anti-cellulite agent included in a composition disclosed herein is an amount effective to mitigate a fatty deposit experienced by an individual upon administration of the composition. Non-limiting examples of anti-cellulite agents include forskolin, xanthine compounds such as, but not limited to, caffeine, theophylline, theobromine, and aminophylline, analogs or derivatives thereof, and any combination thereof. A composition disclosed herein may comprise a single anti-cellulite agent or a plurality of anti-cellulite agents.

Thus in an embodiment, a composition disclosed herein comprises an anti-cellulite agent. In aspects of this embodiment, a composition disclosed herein comprises forskolin, a xanthine compound, an analog or derivative thereof, or any combination thereof.

In other aspects of this embodiment, a composition disclosed herein comprises an anti-cellulite agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an anti-cellulite agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an anti-cellulite agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an anti-cellulite agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a composition disclosed herein does not comprise an anti-cellulite agent.

Aspects of the present specification provide, in part, a hydrogel composition disclosed herein that may optionally comprise an anti-scarring agent. The amount of an anti-scarring agent included in a composition disclosed herein is an amount effective to mitigate a scaring response experienced by an individual upon administration of the composition. Non-limiting examples of anti-scarring agents include IFN-γ, fluorouracil, poly(lactic-co-glycolic acid), methylated polyethylene glycol, polylactic acid, polyethylene glycol, analogs or derivatives thereof, and any combination thereof. A composition disclosed herein may comprise a single anti-scarring agent or a plurality of anti-scarring agents.

Thus in an embodiment, a composition disclosed herein comprises an anti-scarring agent. In aspects of this embodiment, a composition disclosed herein comprises IFN-γ, fluorouracil, poly(lactic-co-glycolic acid), methylated polyethylene glycol, polylactic acid, polyethylene glycol, an analog or derivative thereof, or any combination thereof.

In other aspects of this embodiment, a composition disclosed herein comprises an anti-scarring agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an anti-scarring agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an anti-scarring agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an anti-scarring agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a disclosed herein does not comprise an anti-scarring agent.

Aspects of the present specification provide, in part, a hydrogel composition disclosed herein that may optionally comprise an anti-inflammatory agent. The amount of an anti-inflammatory agent included in a composition disclosed herein is an amount effective to mitigate an inflammatory and/or irritating response experienced by an individual upon administration of the composition. Non-limiting examples of anti-inflammatory agents include dexamethasone, prednisolone, corticosterone, budesonide, estrogen, sulfasalazine, mesalamine, cetirizine, diphenhydramine, antipyrine, methyl salicylate, loratadine, thymol (2-isopropyl-5-methylphenol), carvacrol (5-isopropyl-2-methylphenol), bisabolol (6-Methyl-2-(4-methylcyclohex-3-enyl)hept-5-en-2-ol), allantoin, eucalyptol, phenazone (antipyrin), propyphenazone, and Non-steroidal anti-inflammatory drugs (NSAIDs) include, without limitation, propionic acid derivatives like ibuprofen, naproxen, fenoprofen, ketoprofen, flurbiprofen, and oxaprozin; acetic acid derivatives like indomethacin, sulindac, etodolac, ketorolac, diclofenac, and nabumetone; enolic acid (oxicam) derivatives like piroxicam, meloxicam, tenoxicam, droxicam, lornoxicam, isoxicam; fenamic acid derivatives like mefenamic acid, meclofenamic acid, flufenamic acid, and tolfenamic acid; and selective COX-2 inhibitors (coxibs) like celecoxib, rofecoxib, valdecoxib, parecoxib, lumiracoxib, etoricoxib, and firocoxib, analogs or derivatives thereof, and any combination thereof. A composition disclosed herein may comprise a single anti-inflammatory agent or a plurality of anti-inflammatory agents.

Thus in an embodiment, a composition disclosed herein comprises an anti-inflammatory agent. In aspects of this embodiment, a composition disclosed herein comprises dexamethasone, prednisolone, corticosterone, budesonide, estrogen, sulfasalazine, mesalamine, cetirizine, diphenhydramine, antipyrine, methyl salicylate, loratadine, thymol (2-isopropyl-5-methylphenol), carvacrol (5-isopropyl-2-methylphenol), bisabolol (6-Methyl-2-(4-methylcyclohex-3-enyl)hept-5-en-2-ol), allantoin, eucalyptol, phenazone (antipyrin), propyphenazone, a NSAID, an analog or derivative thereof, or any combination thereof.

In other aspects of this embodiment, a composition disclosed herein comprises an anti-inflammatory agent in an amount of, e.g., at least about 0.001%, at least about 0.01%, about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an anti-inflammatory agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an anti-inflammatory agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an anti-inflammatory agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a composition disclosed herein does not comprise an anesthetic agent.

Aspects of the present specification provide, in part, a hydrogel composition disclosed herein that exhibits a complex modulus, an elastic modulus, a viscous modulus and/or a tan δ. The compositions as disclosed herein are viscoelastic in that the composition has an elastic component (solid-like such as, e.g., crosslinked glycosaminoglycan polymers) and a viscous component (liquid-like such as, e.g., uncrosslinked glycosaminoglycan polymers or a carrier phase) when a force is applied (stress, deformation). The rheological attribute that described this property is the complex modulus ($G^*$), which defines a composition's total resistance to deformation. The complex modulus is a complex number with a real and imaginary part: $G^* = G' + iG''$. The absolute value of $G^*$ is $Abs(G^*) = Sqrt(G'^2 + G''^2)$. The complex modulus can be defined as the sum of the elastic modulus ($G'$) and the viscous modulus ($G''$). Falcone, et al., *Temporary Polysaccharide Dermal Fillers: A Model for Persistence Based on Physical Properties*, Dermatol Surg. 35(8): 1238-1243 (2009); Tezel, supra, 2008; Kablik, supra, 2009; Beasley, supra, 2009; each of which is hereby incorporated by reference in its entirety.

Elastic modulus, or modulus of elasticity, refers to the ability of a hydrogel material to resists deformation, or, conversely, an object's tendency to be non-permanently deformed when a force is applied to it. Elastic modulus characterizes the firmness of a composition and is also known as the storage modulus because it describes the storage of energy from the motion of the composition. The elastic modulus describes the interaction between elasticity and strength (G'=stress/strain) and, as such, provides a quantitative measurement of a composition's hardness or softness. The elastic modulus of an object is defined as the slope of its stress-strain curve in the elastic deformation region: A=stress/strain, where A is the elastic modulus in Pascal's; stress is the force causing the deformation divided by the area to which the force is applied; and strain is the ratio of the change caused by the stress to the original state of the object. Although depending on the speed at which the force is applied, a stiffer composition will have a higher elastic modulus and it will take a greater force to deform the material a given distance, such as, e.g., an injection. Specifying how stresses are to be measured, including directions, allows for many types of elastic moduli to be defined. The three primary elastic moduli are tensile modulus, shear modulus, and bulk modulus.

Viscous modulus is also known as the loss modulus because it describes the energy that is lost as viscous dissipation. Tan $\delta$ is the ratio of the viscous modulus and the elastic modulus, tan $\delta$=G"/G'. Falcone, supra, 2009. For tan $\delta$ values disclosed in the present specification, a tan $\delta$ is obtained from the dynamic modulus at a frequency of 1 Hz. A lower tan $\delta$ corresponds to a stiffer, harder, or more elastic composition.

In another embodiment, a hydrogel composition disclosed herein exhibits an elastic modulus. In aspects of this embodiment, a hydrogel composition exhibits an elastic modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, about 800 Pa, about 850 Pa, about 900 Pa, about 950 Pa, about 1,000 Pa, about 1,200 Pa, about 1,300 Pa, about 1,400 Pa, about 1,500 Pa, about 1,600 Pa, about 1700 Pa, about 1800 Pa, about 1900 Pa, about 2,000 Pa, about 2,100 Pa, about 2,200 Pa, about 2,300 Pa, about 2,400 Pa, or about 2,500 Pa. In other aspects of this embodiment, a hydrogel composition exhibits an elastic modulus of, e.g., at least 25 Pa, at least 50 Pa, at least 75 Pa, at least 100 Pa, at least 125 Pa, at least 150 Pa, at least 175 Pa, at least 200 Pa, at least 250 Pa, at least 300 Pa, at least 350 Pa, at least 400 Pa, at least 450 Pa, at least 500 Pa, at least 550 Pa, at least 600 Pa, at least 650 Pa, at least 700 Pa, at least 750 Pa, at least 800 Pa, at least 850 Pa, at least 900 Pa, at least 950 Pa, at least 1,000 Pa, at least 1,200 Pa, at least 1,300 Pa, at least 1,400 Pa, at least 1,500 Pa, at least 1,600 Pa, at least 1700 Pa, at least 1800 Pa, at least 1900 Pa, at least 2,000 Pa, at least 2,100 Pa, at least 2,200 Pa, at least 2,300 Pa, at least 2,400 Pa, or at least 2,500 Pa. In yet other aspects of this embodiment, a hydrogel composition exhibits an elastic modulus of, e.g., at most 25 Pa, at most 50 Pa, at most 75 Pa, at most 100 Pa, at most 125 Pa, at most 150 Pa, at most 175 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, at most 700 Pa, at most 750 Pa, at most 800 Pa, at most 850 Pa, at most 900 Pa, at most 950 Pa, at most 1,000 Pa, at most 1,200 Pa, at most 1,300 Pa, at most 1,400 Pa, at most 1,500 Pa, or at most 1,600 Pa. In still other aspects of this embodiment, a hydrogel composition exhibits an elastic modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, about 125 Pa to about 800 Pa, about 500 Pa to about 1,600 Pa, about 600 Pa to about 1,600 Pa, about 700 Pa to about 1,600 Pa, about 800 Pa to about 1,600 Pa, about 900 Pa to about 1,600 Pa, about 1,000 Pa to about 1,600 Pa, about 1,100 Pa to about 1,600 Pa, about 1,200 Pa to about 1,600 Pa, about 500 Pa to about 2,500 Pa, about 1,000 Pa to about 2,500 Pa, about 1,500 Pa to about 2,500 Pa, about 2,000 Pa to about 2,500 Pa, about 1,300 Pa to about 1,600 Pa, about 1,400 Pa to about 1,700 Pa, about 1,500 Pa to about 1,800 Pa, about 1,600 Pa to about 1,900 Pa, about 1,700 Pa to about 2,000 Pa, about 1,800 Pa to about 2,100 Pa, about 1,900 Pa to about 2,200 Pa, about 2,000 Pa to about 2,300 Pa, about 2,100 Pa to about 2,400 Pa, or about 2,200 Pa to about 2,500 Pa.

In another embodiment, a hydrogel composition disclosed herein exhibits a viscous modulus. In aspects of this embodiment, a hydrogel composition exhibits a viscous modulus of, e.g., about 10 Pa, about 20 Pa, about 30 Pa, about 40 Pa, about 50 Pa, about 60 Pa, about 70 Pa, about 80 Pa, about 90 Pa, about 100 Pa, about 150 Pa, about 200 Pa, about 250 Pa, about 300 Pa, about 350 Pa, about 400 Pa, about 450 Pa, about 500 Pa, about 550 Pa, about 600 Pa, about 650 Pa, or about 700 Pa. In other aspects of this embodiment, a hydrogel composition exhibits a viscous modulus of, e.g., at most 10 Pa, at most 20 Pa, at most 30 Pa, at most 40 Pa, at most 50 Pa, at most 60 Pa, at most 70 Pa, at most 80 Pa, at most 90 Pa, at most 100 Pa, at most 150 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, or at most 700 Pa. In yet other aspects of this embodiment, a hydrogel composition exhibits a viscous modulus of, e.g., about 10 Pa to about 30 Pa, about 10 Pa to about 50 Pa, about 10 Pa to about 100 Pa, about 10 Pa to about 150 Pa, about 70 Pa to about 100 Pa, about 50 Pa to about 350 Pa, about 150 Pa to about 450 Pa, about 250 Pa to about 550 Pa, about 350 Pa to about 700 Pa, about 50 Pa to about 150 Pa, about 100 Pa to about 200 Pa, about 150 Pa to about 250 Pa, about 200 Pa to about 300 Pa, about 250 Pa to about 350 Pa, about 300 Pa to about 400 Pa, about 350 Pa to about 450 Pa, about 400 Pa to about 500 Pa, about 450 Pa to about 550 Pa, about 500 Pa to about 600 Pa, about 550 Pa to about 650 Pa, or about 600 Pa to about 700 Pa.

In another embodiment, a hydrogel composition disclosed herein exhibits a tan $\delta$. In aspects of this embodiment, a hydrogel composition exhibits a tan $\delta$ of, e.g., about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5. In other aspects of this embodiment, a hydrogel composition exhibits a tan $\delta$ of, e.g., at most 0.1, at most 0.2, at most 0.3, at most 0.4, at most 0.5, at most 0.6, at most 0.7, at most 0.8, at most 0.9, at most 1.0, at most 1.1, at most 1.2, at most 1.3, at most 1.4, at most 1.5, at most 1.6, at most 1.7, at most 1.8, at most 1.9, at most 2.0, at most 2.1, at most 2.2, at most 2.3, at most 2.4, or at most 2.5. In yet other aspects of this embodiment, a hydrogel composition exhibits a tan $\delta$ of, e.g., about 0.1 to about 0.3, about 0.3 to about 0.5, about 0.5 to about 0.8, about 1.1 to about 1.4, about 1.4 to about 1.7, about 0.3 to about 0.6, about 0.1 to about 0.5, about 0.5 to about 0.9, about 0.1 to about 0.6, about 0.1 to about 1.0, about 0.5 to about 1.5, about 1.0 to about 2.0, or about 1.5 to about 2.5.

Aspects of the present specification provide, in part, a hydrogel composition disclosed herein having a transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The silk fibroin hydrogels disclosed herein may, or may not, exhibit optical properties such as transparency and translucency. In certain cases, e.g., superficial line filling, it would be an advantage to have an opaque hydrogel. In other cases such as development of a lens or a "humor" for filling the eye, it would be an advantage to have a translucent hydrogel. These properties could be modified by affecting the structural distribution of the hydrogel material. Factors used to control a hydrogel's optical properties include, without limitation, polymer concentration, gel crystallinity, and hydrogel homogeneity.

When light encounters a material, it can interact with it in several different ways. These interactions depend on the nature of the light (its wavelength, frequency, energy, etc.) and the nature of the material. Light waves interact with an object by some combination of reflection, and transmittance with refraction. As such, an optically transparent material allows much of the light that falls on it to be transmitted, with little light being reflected. Materials which do not allow the transmission of light are called optically opaque or simply opaque.

In an embodiment, a hydrogel composition disclosed herein is optically transparent. In aspects of this embodiment, a hydrogel composition transmits, e.g., about 75% of the light, about 80% of the light, about 85% of the light, about 90% of the light, about 95% of the light, or about 100% of the light. In other aspects of this embodiment, a hydrogel composition transmits, e.g., at least 75% of the light, at least 80% of the light, at least 85% of the light, at least 90% of the light, or at least 95% of the light. In yet other aspects of this embodiment, a hydrogel composition transmits, e.g., about 75% to about 100% of the light, about 80% to about 100% of the light, about 85% to about 100% of the light, about 90% to about 100% of the light, or about 95% to about 100% of the light.

In another embodiment, a hydrogel composition disclosed herein is optically opaque. In aspects of this embodiment, a hydrogel composition transmits, e.g., about 5% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, or about 70% of the light. In other aspects of this embodiment, a hydrogel composition transmits, e.g., at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a hydrogel composition transmits, e.g., about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 65%, about 5% to about 70%, about 5% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%, of the light.

In an embodiment, a hydrogel composition disclosed herein is optically translucent. In aspects of this embodiment, a hydrogel composition diffusely transmits, e.g., about 75% of the light, about 80% of the light, about 85% of the light, about 90% of the light, about 95% of the light, or about 100% of the light. In other aspects of this embodiment, a hydrogel composition diffusely transmits, e.g., at least 75% of the light, at least 80% of the light, at least 85% of the light, at least 90% of the light, or at least 95% of the light. In yet other aspects of this embodiment, a hydrogel composition diffusely transmits, e.g., about 75% to about 100% of the light, about 80% to about 100% of the light, about 85% to about 100% of the light, about 90% to about 100% of the light, or about 95% to about 100% of the light.

A hydrogel composition disclosed herein may be further processed by pulverizing the hydrogel into particles and optionally mixed with a carrier phase such as, e.g., water or a saline solution to form an injectable or topical substance like a solution, oil, lotion, gel, ointment, cream, slurry, salve, or paste. As such, the disclosed hydrogel compositions may be monophasic or multiphasic compositions. A hydrogel may be milled to a particle size from about 10 μm to about 1000 μm in diameter, such as about 15 μm to about 30 μm, about 50 μm to about 75 μm, about 100 μm to about 150 μm, about 200 μm to about 300 μm, about 450 μm to about 550 μm, about 600 μm to about 700 μm, about 750 μm to about 850 μm, or about 900 μm to about 1,000 μm.

Aspects of the present specification provide, in part, a composition disclosed herein is injectable. As used herein, the term "injectable" refers to a material having the properties necessary to administer the composition into a skin region of an individual using an injection device with a fine needle. As used herein, the term "fine needle" refers to a needle that is 27 gauge or smaller. Injectability of a composition disclosed herein can be accomplished by sizing the hydrogel particles as discussed above.

In aspect of this embodiment, a hydrogel composition disclosed herein is injectable through a fine needle. In other aspects of this embodiment, a hydrogel composition disclosed herein is injectable through a needle of, e.g., about 27 gauge, about 30 gauge, or about 32 gauge. In yet other aspects of this embodiment, a hydrogel composition disclosed herein is injectable through a needle of, e.g., 22 gauge or smaller, 27 gauge or smaller, 30 gauge or smaller, or 32 gauge or smaller. In still other aspects of this embodiment, a hydrogel composition disclosed herein is injectable through a needle of, e.g., about 22 gauge to about 35 gauge, 22 gauge to about 34 gauge, 22 gauge to about 33 gauge, 22 gauge to about 32 gauge, about 22 gauge to about 27 gauge, or about 27 gauge to about 32 gauge.

In aspects of this embodiment, a hydrogel composition disclosed herein can be injected with an extrusion force of about 60 N, about 55 N, about 50 N, about 45 N, about 40 N, about 35 N, about 30 N, about 25 N, about 20 N, or 15 N at speeds of 100 mm/min. In other aspects of this embodiment, a hydrogel composition disclosed herein can be injected through a 27 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In yet other aspects of this embodiment, a hydrogel composition disclosed herein can be injected through a 30 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In still other aspects of this embodiment, a hydrogel composition disclosed herein can be injected through a 32 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less.

Aspects of the present specification provide, in part, a hydrogel composition disclosed herein that exhibits cohesivity. Cohesivity, also referred to as cohesion cohesive attraction, cohesive force, or compression force is a physical property of a material, caused by the intermolecular attraction between like-molecules within the material that acts to unite the molecules. Cohesivity is expressed in terms of grams-force (gmf). Cohesiveness is affected by, among other factors, the molecular weight ratio of the initial free glycosaminoglycan polymer, the degree of crosslinking of glycosaminoglycan polymers, the amount of residual free glycosaminoglycan polymers following crosslinking, and the pH of the hydrogel composition. A composition should be sufficiently cohesive as to remain localized to a site of administration. Additionally, in certain applications, a sufficient cohesiveness is important for a composition to retain its shape, and thus functionality, in the event of mechanical load cycling. As such, in one embodiment, a hydrogel composition disclosed herein exhibits cohesivity, on par with water. In yet another embodiment, a hydrogel composition disclosed herein exhibits sufficient cohesivity to remain localized to a site of administration. In still another embodiment, a hydrogel composition disclosed herein exhibits sufficient cohesivity to retain its shape. In a further embodiment, a hydrogel composition disclosed herein exhibits sufficient cohesivity to retain its shape and functionality.

Aspects of the present specification provide, in part, a hydrogel composition disclosed herein that exhibits a physiologically-acceptable osmolarity. As used herein, the term "osmolarity" refers to the concentration of osmotically active solutes in solution. As used herein, the term "a physiologically-acceptable osmolarity" refers to an osmolarity in accord with, or characteristic of, the normal functioning of a living organism. As such, administration of a hydrogel composition as disclosed herein exhibits an osmolarity that has substantially no long term or permanent detrimental effect when administered to a mammal. Osmolarity is expressed in terms of osmoles of osmotically active solute per liter of solvent (Osmol/L or Osm/L). Osmolarity is distinct from molarity because it measures moles of osmotically active solute particles rather than moles of solute. The distinction arises because some compounds can dissociate in solution, whereas others cannot. The osmolarity of a solution can be calculated from the following expression: $Osmol/L = \Sigma \phi_i \eta_i C_i$, where $\phi$ is the osmotic coefficient, which accounts for the degree of non-ideality of the solution; $\eta$ is the number of particles (e.g. ions) into which a molecule dissociates; and C is the molar concentration of the solute; and i is the index representing the identity of a particular solute. The osmolarity of a hydrogel composition disclosed herein can be measured using a conventional method that measures solutions.

In an embodiment, a hydrogel composition disclosed herein exhibits a physiologically-acceptable osmolarity. In aspects of this embodiment, a hydrogel composition exhibits an osmolarity of, e.g., about 100 mOsm/L, about 150 mOsm/L, about 200 mOsm/L, about 250 mOsm/L, about 300 mOsm/L, about 350 mOsm/L, about 400 mOsm/L, about 450 mOsm/L, or about 500 mOsm/L. In other aspects of this embodiment, a hydrogel composition exhibits an osmolarity of, e.g., at least 100 mOsm/L, at least 150 mOsm/L, at least 200 mOsm/L, at least 250 mOsm/L, at least 300 mOsm/L, at least 350 mOsm/L, at least 400 mOsm/L, at least 450 mOsm/L, or at least 500 mOsm/L. In yet other aspects of this embodiment, a hydrogel composition exhibits an osmolarity of, e.g., at most 100 mOsm/L, at most 150 mOsm/L, at most 200 mOsm/L, at most 250 mOsm/L, at most 300 mOsm/L, at most 350 mOsm/L, at most 400 mOsm/L, at most 450 mOsm/L, or at most 500 mOsm/L. In still other aspects of this embodiment, a hydrogel composition exhibits an osmolarity of, e.g., about 100 mOsm/L to about 500 mOsm/L, about 200 mOsm/L to about 500 mOsm/L, about 200 mOsm/L to about 400 mOsm/L, about 300 mOsm/L to about 400 mOsm/L, about 270 mOsm/L to about 390 mOsm/L, about 225 mOsm/L to about 350 mOsm/L, about 250 mOsm/L to about 325 mOsm/L, about 275 mOsm/L to about 300 mOsm/L, or about 285 mOsm/L to about 290 mOsm/L.

spects of the present specification provide, in part, a hydrogel composition disclosed herein that exhibits a physiologically-acceptable osmolality. As used herein, the term "osmolality" refers to the concentration of osmotically active solutes per kilo of solvent in the body. As used herein, the term "a physiologically-acceptable osmolality" refers to an osmolality in accord with, or characteristic of, the normal functioning of a living organism. As such, administration of a hydrogel composition disclosed herein exhibits an osmolality that has substantially no long term or permanent detrimental effect when administered to a mammal. Osmolality is expressed in terms of osmoles of osmotically active solute per kilogram of solvent (osmol/kg or Osm/kg) and is equal to the sum of the molalities of all the solutes present in that solution. The osmolality of a solution can be measured using an osmometer. The most commonly used instrument in modern laboratories is a freezing point depression osmometer. This instruments measure the change in freezing point that occurs in a solution with increasing osmolality (freezing point depression osmometer) or the change in vapor pressure that occurs in a solution with increasing osmolality (vapor pressure depression osmometer).

In an embodiment, a hydrogel composition disclosed herein exhibits a physiologically-acceptable osmolality. In aspects of this embodiment, a hydrogel composition exhibits an osmolality of, e.g., about 100 mOsm/kg, about 150 mOsm/kg, about 200 mOsm/kg, about 250 mOsm/kg, about 300 mOsm/kg, about 350 mOsm/kg, about 400 mOsm/kg, about 450 mOsm/kg, or about 500 mOsm/kg. In other aspects of this embodiment, a hydrogel composition exhibits an osmolality of, e.g., at least 100 mOsm/kg, at least 150 mOsm/kg, at least 200 mOsm/kg, at least 250 mOsm/kg, at least 300 mOsm/kg, at least 350 mOsm/kg, at least 400 mOsm/kg, at least 450 mOsm/kg, or at least 500 mOsm/kg. In yet other aspects of this embodiment, a hydrogel composition exhibits an osmolality of, e.g., at most 100 mOsm/ kg, at most 150 mOsm/kg, at most 200 mOsm/kg, at most 250 mOsm/kg, at most 300 mOsm/kg, at most 350 mOsm/kg, at most 400 mOsm/kg, at most 450 mOsm/kg, or at most 500 mOsm/kg. In still other aspects of this embodiment, a hydrogel composition exhibits an osmolality of, e.g., about 100 mOsm/kg to about 500 mOsm/kg, about 200 mOsm/kg to about 500 mOsm/kg, about 200 mOsm/kg to about 400 mOsm/kg, about 300 mOsm/kg to about 400 mOsm/kg, about 270 mOsm/kg to about 390 mOsm/kg, about 225 mOsm/kg to about 350 mOsm/kg, about 250 mOsm/kg to about 325 mOsm/kg, about 275 mOsm/kg to about 300 mOsm/kg, or about 285 mOsm/kg to about 290 mOsm/kg.

Aspects of the present specification provide, in part, a hydrogel composition disclosed herein that exhibits substantial stability. As used herein, the term "stability" or "stable" when referring to a hydrogel composition disclosed herein refers to a composition that is not prone to degrading, decomposing, or breaking down to any substantial or significant degree while stored before administration to an individual. As used herein, the term "substantial heat stability", "substantially heat stable", "autoclave stable", or "steam sterilization stable" refers to a hydrogel composition disclosed herein that is substantially stable when subjected to a heat treatment as disclosed herein.

Stability of a hydrogel composition disclosed herein can be determined by subjecting a hydrogel composition to a heat treatment, such as, e.g., steam sterilization at normal pressure or under pressure (e.g., autoclaving). Preferably the heat treatment is carried out at a temperature of at least about 100° C. for between about one minute and about 10 minutes. Substantial stability of a hydrogel composition disclosed herein can be evaluated 1) by determining the change in the extrusion force ($\Delta F$) of a hydrogel composition disclosed herein after sterilization, where the change in extrusion force less 2N is indicative of a substantially stable hydrogel composition as measured by (the extrusion force of a hydrogel composition with the specified additives) minus (the extrusion force of the a hydrogel composition without the added additives); and/or 2) by determining the change in rheological properties of a hydrogel composition disclosed herein after sterilization, where the change in tan $\delta$ 1 Hz of less than 0.1 is indicative of a substantially stable hydrogel composition as measured by (tan $\delta$ 1 Hz of gel formulation with additives) minus (tan $\delta$ 1 Hz of gel formulation without additives). As such, a substantially stable hydrogel composition disclosed herein retains one or more of the following characteristics after sterilization: homogeneousness, extrusion force, cohesiveness, hyaluronan concentration, agent(s) concentration, osmolarity, pH, or other rheological characteristics desired by the hydrogel before the heat treatment.

In an embodiment, a hydrogel composition comprising a glycosaminoglycan polymer and the at least one agent disclosed herein is processed using a heat treatment that maintains the desired hydrogel properties disclosed herein. In aspects of this embodiment, a hydrogel composition comprising a glycosaminoglycan polymer and the at least one agent disclosed herein is processed using a heat treatment of, e.g., about 100° C., about 105° C., about 110° C., about 115° C., about 120° C., about 125° C., or about 130° C. In other aspects of this embodiment, a hydrogel composition comprising a glycosaminoglycan polymer and the at least one agent disclosed herein is processed using a heat treatment of, e.g., at least 100° C., at least 105° C., at least 110° C., at least 115° C., at least 120° C., at least 125° C., or at least 130° C. In yet other aspects of this embodiment, a hydrogel composition comprising a glycosaminoglycan polymer and the at least one agent disclosed herein is processed using a heat treatment of, e.g., about 100° C. to about 120° C., about 100° C. to about 125° C., about 100° C. to about 130° C., about 100° C. to about 135° C., about 110° C. to about 120° C., about 110° C. to about 125° C., about 110° C. to about 130° C., about 110° C. to about 135° C., about 120° C. to about 125° C., about 120° C. to about 130° C., about 120° C. to about 135° C., about 125° C. to about 130° C., or about 125° C. to about 135° C.

Long term stability of a hydrogel composition disclosed herein can be determined by subjecting a hydrogel composition to a heat treatment, such as, e.g., storage in an about 45° C. environment for about 60 days. Long term stability of a hydrogel composition disclosed herein can be evaluated 1) by assessing the clarity and color of a hydrogel composition after the 45° C. heat treatment, with a clear and uncolored hydrogel composition being indicative of a substantially stable hydrogel composition; 2) by determining the change in the extrusion force ($\Delta F$) of a hydrogel composition disclosed herein after the 45° C. heat treatment, where the change in extrusion force less 2N is indicative of a substantially stable hydrogel composition as measured by (the extrusion force of a hydrogel composition with the specified additives before the 45° C. heat treatment) minus (the extrusion force of the a hydrogel composition with the specified additives after the 45° C. heat treatment); and/or 3) by determining the change in rheological properties of a hydrogel composition disclosed herein after sterilization, where the change in tan $\delta$ 1 Hz of less than 0.1 is indicative of a substantially stable hydrogel composition as measured by (tan $\delta$ 1 Hz of gel formulation with the specified additives before the 45° C. heat treatment) minus (tan $\delta$ 1 Hz of gel formulation with the specified additives after the 45° C. heat treatment). As such, a long term stability of a hydrogel composition disclosed herein is evaluated by retention of one or more of the following characteristics after the 45° C. heat treatment: clarity (transparency and translucency), homogeneousness, and cohesiveness.

In aspects of this embodiment, a hydrogel composition is substantially stable at room temperature for, e.g., about 3 months, about 6 months, about 9 months, about 12 months, about 15 months, about 18 months, about 21 months, about 24 months, about 27 months, about 30 months, about 33 months, or about 36 months. In other aspects of this embodiment, a hydrogel composition is substantially stable at room temperature for, e.g., at least 3 months, at least 6 months, at least 9 months, at least 12 months, at least 15 months, at least 18 months, at least 21 months, at least 24 months, at least 27 months, at least 30 months, at least 33 months, or at least 36 months. In other aspects of this embodiment, a hydrogel composition is substantially stable at room temperature for, e.g., about 3 months to about 12 months, about 3 months to about 18 months, about 3 months to about 24 months, about 3 months to about 30 months, about 3 months to about 36 months, about 6 months to about 12 months, about 6 months to about 18 months, about 6 months to about 24 months, about 6 months to about 30 months, about 6 months to about 36 months, about 9 months to about 12 months, about 9 months to about 18 months, about 9 months to about 24 months, about 9 months to about 30 months, about 9 months to about 36 months, about 12 months to about 18 months, about 12 months to about 24 months, about 12 months to about 30 months, about 12 months to about 36 months, about 18 months to about 24 months, about 18 months to about 30 months, or about 18 months to about 36 months.

Aspects of the present specification provide, in part, a hydrogel composition disclosed herein that is a pharmaceutically-acceptable composition. As used herein, the term "pharmaceutically acceptable" means any molecular entity or composition that does not produce an adverse, allergic or other untoward or unwanted reaction when administered to an individual. A pharmaceutically-acceptable hydrogel composition is useful for medical and veterinary applications. A pharmaceutically-acceptable hydrogel composition may be administered to an individual alone, or in combination with other supplementary active ingredients, agents, drugs or hormones.

Aspects of the present specification provide, in part, a hydrogel composition as disclosed herein comprising a pharmacologically acceptable excipient. As used herein, the term "pharmacologically acceptable excipient" is synonymous with "pharmacological excipient" or "excipient" and refers to any excipient that has substantially no long term or permanent detrimental effect when administered to mammal and encompasses compounds such as, e.g., stabilizing agent, a bulking agent, a cryo-protectant, a lyo-protectant, an additive, a vehicle, a carrier, a diluent, or an auxiliary. An excipient generally is mixed with an active ingredient, or permitted to dilute or enclose the active ingredient and can be a solid, semi-solid, or liquid agent. It is also envisioned that a pharmaceutical composition as disclosed herein can include one or more pharmaceutically acceptable excipients that facilitate processing of an active ingredient into pharmaceutically acceptable compositions. Insofar as any pharmacologically acceptable excipient is not incompatible with the active ingredient, its use in pharmaceutically acceptable compositions is contemplated. Non-limiting examples of pharmacologically acceptable excipients can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

It is further envisioned that a hydrogel composition disclosed herein may optionally include, without limitation, other pharmaceutically acceptable components, including, without limitation, buffers, preservatives, tonicity adjusters, salts, antioxidants, osmolality adjusting agents, emulsifying agents, wetting agents, sweetening or flavoring agents, and the like.

A pharmaceutically acceptable buffer is a buffer that can be used to prepare a hydrogel composition disclosed herein, provided that the resulting preparation is pharmaceutically acceptable. Non-limiting examples of pharmaceutically acceptable buffers include acetate buffers, borate buffers, citrate buffers, neutral buffered salines, phosphate buffers, and phosphate buffered salines. Any concentration of a pharmaceutically acceptable buffer can be useful in formulating a pharmaceutical composition disclosed herein, with the proviso that a therapeutically effective amount of the active ingredient is recovered using this effective concentration of buffer. Non-limiting examples of concentrations of physiologically-acceptable buffers occur within the range of about 0.1 mM to about 900 mM. The pH of pharmaceutically acceptable buffers may be adjusted, provided that the resulting preparation is pharmaceutically acceptable. It is understood that acids or bases can be used to adjust the pH of a pharmaceutical composition as needed. Any buffered pH level can be useful in formulating a pharmaceutical composition, with the proviso that a therapeutically effective amount of the matrix polymer active ingredient is recovered using this effective pH level. Non-limiting examples of physiologically-acceptable pH occur within the range of about pH 5.0 to about pH 8.5. For example, the pH of a hydrogel composition disclosed herein can be about 5.0 to about 8.0, or about 6.5 to about 7.5, about 7.0 to about 7.4, or about 7.1 to about 7.3.

Pharmaceutically acceptable preservatives include, without limitation, sodium metabisulfite, sodium thiosulfate, acetylcysteine, butylated hydroxyanisole and butylated hydroxytoluene. Pharmaceutically acceptable preservatives include, without limitation, benzalkonium chloride, chlorobutanol, thimerosal, phenylmercuric acetate, phenylmercuric nitrate, a stabilized oxy chloro composition, such as, e.g., PURITE® (Allergan, Inc. Irvine, Calif.) and chelants, such as, e.g., DTPA or DTPA-bisamide, calcium DTPA, and CaNaDTPA-bisamide.

Pharmaceutically acceptable tonicity adjustors useful in a hydrogel composition disclosed herein include, without limitation, salts such as, e.g., sodium chloride and potassium chloride; and glycerin. The composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition disclosed herein. Other non-limiting examples of pharmacologically acceptable components can be found in, e.g., Ansel, supra, (1999); Gennaro, supra, (2000); Hardman, supra, (2001); and Rowe, supra, (2003), each of which is hereby incorporated by reference in its entirety.

Aspects of the present specification provide, in part, a method of treating a soft tissue condition of an individual by administering a hydrogel composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a hydrogel composition disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A hydrogel composition is administered to an individual. An individual is typically a human being of any age, gender or race. Typically, any individual who is a candidate for a conventional procedure to treat a soft tissue condition is a candidate for a method disclosed herein. Although a subject experiencing the signs of aging skin is an adult, subjects experiencing premature aging or other skin conditions suitable for treatment (for example, a scar) can also be treated with a hydrogel composition disclosed herein. In addition, the presently disclosed hydrogel compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The hydrogel composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, a mesotherapy, Parry-Romberg syndrome, lupus erythematosus profundus, dermal divots, scars, sunken cheeks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD). As used herein, the term "mesotherapy" refers to a non-surgical cosmetic treatment technique of the skin involving intra-epidermal, intradermal, and/or subcutaneous injection of an agent administered as small multiple droplets into the epidermis, dermo-epidermal junction, and/or the dermis.

The amount of a hydrogel composition used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

For example, for breast augmentation procedures, effectiveness of the compositions and methods may be manifested by one or more of the following clinical and/or cosmetic measures: increased breast size, altered breast shape, altered breast contour, sustained engraftment, reduction in the risk of capsular contraction, decreased rate of liponecrotic cyst formation, improved patient satisfaction and/or quality of life, and decreased use of breast implant.

As another example, effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

As yet another example, for urinary incontinence procedures, effectiveness of the compositions and methods for sphincter support may be manifested by one or more of the following clinical measures: decreased frequency of incontinence, sustained engraftment, improved patient satisfaction and/or quality of life, and decreased use of implantable foreign filler.

In aspects of this embodiment, the amount of a hydrogel composition administered is, e.g., about 0.01 g, about 0.05 g, about 0.1 g, about 0.5 g, about 1 g, about 5 g, about 10 g, about 20 g, about 30 g, about 40 g, about 50 g, about 60 g, about 70 g, about 80 g, about 90 g, about 100 g, about 150 g, or about 200 g. In other aspects of this embodiment, the amount of a hydrogel composition administered is, e.g., about 0.01 g to about 0.1 g, about 0.1 g to about 1 g, about 1 g to about 10 g, about 10 g to about 100 g, or about 50 g to about 200 g. In yet other aspects of this embodiment, the amount of a hydrogel composition administered is, e.g., about 0.01 mL, about 0.05 mL, about 0.1 mL, about 0.5 mL, about 1 mL, about 5 mL, about 10 mL, about 20 mL, about 30 mL, about 40 mL, about 50 mL, about 60 mL, about 70 g, about 80 mL, about 90 mL, about 100 mL, about 150 mL, or about 200 mL. In other aspects of this embodiment, the amount of a hydrogel composition administered is, e.g., about 0.01 mL to about 0.1 mL, about 0.1 mL to about 1 mL, about 1 mL to about 10 mL, about 10 mL to about 100 mL, or about 50 mL to about 200 mL.

The duration of treatment will typically be determined based on the cosmetic and/or clinical effect desired by the individual and/or physician and the body part or region being treated. In aspects of this embodiment, administration of a hydrogel composition disclosed herein can treat a soft tissue condition for, e.g., about 6 months, about 7 months, about 8 months, about 9 months, about 10 months, about 11 months, about 12 months, about 13 months, about 14 months, about 15 months, about 18 months, or about 24 months. In other aspects of this embodiment, administration of a hydrogel composition disclosed herein can treat a soft tissue condition for, e.g., at least 6 months, at least 7 months, at least 8 months, at least 9 months, at least 10 months, at least 11 months, at least 12 months, at least 13 months, at least 14 months, at least 15 months, at least 18 months, or at least 24 months. In yet aspects of this embodiment, administration of a hydrogel composition disclosed herein can treat a soft tissue condition for, e.g., about 6 months to about 12 months, about 6 months to about 15 months, about 6 months to about 18 months, about 6 months to about 21 months, about 6 months to about 24 months, about 9 months to about 12 months, about 9 months to about 15 months, about 9 months to about 18 months, about 9 months to about 21 months, about 6 months to about 24 months, about 12 months to about 15 months, about 12 months to about 18 months, about 12 months to about 21 months, about 12 months to about 24 months, about 15 months to about 18 months, about 15 months to about 21 months, about 15 months to about 24 months, about 18 months to about 21 months, about 18 months to about 24 months, or about 21 months to about 24 months.

Aspects of the present specification provide, in part, administering a hydrogel composition disclosed herein. As used herein, the term "administering" means any delivery mechanism that provides a composition disclosed herein to an individual that potentially results in a clinically, therapeutically, or experimentally beneficial result. The actual delivery mechanism used to administer a composition to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof. In an aspect of this embodiment, a composition disclosed herein is administered to a skin region of an individual by injection.

The route of administration of a hydrogel composition to an individual patient will typically be determined based on the cosmetic and/or clinical effect desired by the individual and/or physician and the body part or region being treated. A composition disclosed herein may be administered by any means known to persons of ordinary skill in the art including, without limitation, syringe with needle, a pistol (for example, a hydropneumatic-compression pistol), catheter, topically, or by direct surgical implantation. The hydrogel composition disclosed herein can be administered into a skin region such as, e.g., a dermal region or a hypodermal region. For example, a hydrogel composition disclosed herein can be injected utilizing needles with a diameter of about 0.26 mm to about 0.4 mm and a length ranging from about 4 mm to about 14 mm. Alternately, the needles can be 21 to 32 G and have a length of about 4 mm to about 70 mm. Preferably, the needle is a single-use needle. The needle can be combined with a syringe, catheter, and/or a pistol.

In addition, a composition disclosed herein can be administered once, or over a plurality of times. Ultimately, the timing used will follow quality care standards. For example, a hydrogel composition disclosed herein can be administered once or over several sessions with the sessions spaced apart by a few days, or weeks. For instance, an individual can be administered a hydrogel composition disclosed herein every 1, 2, 3, 4, 5, 6, or 7 days or every 1, 2, 3, or 4 weeks. The administration a hydrogel composition disclosed herein to an individual can be on a monthly or bi-monthly basis or administered every 3, 6, 9, or 12 months.

For a breast soft tissue replacement procedure, the route of administration may include axillary, periareolar, and/or inframammary routes. Alternatively or in addition, a composition may be delivered through a transaxillary endoscopic subpectoral approach. For a facial soft tissue replacement procedure, the route of administration can be frontal, temporal, zygomatic, periocular, mandibula, perioral or chin routes. In urinary incontinence procedures, the route of administration may include transurethral or periurethral routes. Alternatively or in addition, administration may be delivered via an antegrade route. The routes discussed herein do not exclude the use of multiple routes to achieve the desired clinical effect.

Aspects of the present specification provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In an aspect of this embodiment, a hydrogel composition disclosed herein is administered to a skin region of an individual by injection into a dermal region or a hypodermal region. In aspects of this embodiment, a hydrogel composition disclosed herein is administered to a dermal region of an individual by injection into, e.g., an epidermal-dermal junction region, a papillary region, a reticular region, or any combination thereof.

Aspects of the present specification disclose, in part, a method of treating a soft tissue condition of an individual, the method comprising the steps of administering a hydrogel composition disclosed herein to a site of the soft tissue condition of the individual, wherein the administration of the composition improves the soft tissue condition, thereby treating the soft tissue condition. In aspects of this embodiment, a soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

Other aspects of the present specification disclose, in part, a method of treating a skin condition comprises the step of administering to an individual suffering from a skin condition a hydrogel composition disclosed herein, wherein the administration of the composition improves the skin condition, thereby treating the skin condition. In an aspect of this embodiment, a skin condition is a method of treating skin dehydration comprises the step of administering to an individual suffering from skin dehydration a hydrogel composition disclosed herein, wherein the administration of the composition rehydrates the skin, thereby treating skin dehydration. In another aspect of this embodiment, a method of treating a lack of skin elasticity comprises the step of administering to an individual suffering from a lack of skin elasticity a hydrogel composition disclosed herein, wherein the administration of the composition increases the elasticity of the skin, thereby treating a lack of skin elasticity. In yet another aspect of this embodiment, a method of treating skin roughness comprises the step of administering to an individual suffering from skin roughness a hydrogel composition disclosed herein, wherein the administration of the composition decreases skin roughness, thereby treating skin roughness. In still another aspect of this embodiment, a method of treating a lack of skin tautness comprises the step of administering to an individual suffering from a lack of skin tautness a hydrogel composition disclosed herein, wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a hydrogel composition disclosed herein, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a hydrogel composition disclosed herein, wherein the administration of the composition increases skin tone or radiance, thereby treating skin paleness. In another aspect of this embodiment, a method of treating skin wrinkles comprises the step of administering to an individual suffering from skin wrinkles a hydrogel composition disclosed herein, wherein the administration of the composition reduces or eliminates skin wrinkles, thereby treating skin wrinkles. In yet another aspect of this embodiment, a method of treating skin wrinkles comprises the step of administering to an individual a hydrogel composition disclosed herein, wherein the administration of the composition makes the skin resistant to skin wrinkles, thereby treating skin wrinkles.

EXAMPLES

The following examples illustrate representative embodiments now contemplated, but should not be construed to limit the disclosed hydrogel compositions, and methods of soft tissue augmentation using such hydrogel compositions.

Example 1

Method for Determining Gel Cohesivity

This example illustrates tests that may be performed in order to evidence or quantify cohesivity of a HA-based gel composition.

First, 0.2 g or 0.4 g of a gel composition to be tested is placed in a glass syringe. Next, 0.2 g or more of phosphate buffer is added to the syringe and the mixture is thoroughly mixed for about 1 hour to obtain a homogenous mixture. Then, the homogenized mixture is centrifuged for 5 min at 2000 tr/min to remove the air bubbles and to allow the decantation of any particles. The syringe is then held in a vertical position and one drop of eosin colorant is deposited at the surface of the gel by means of a syringe and an 18G needle. After 10 min, the dye has slowly diffused through the gel.

After dilution of the gel, homogenization and decantation, a relatively low cohesivity gel shows a phase separation (an upper diluted less viscous phase without particles and a lower one composed of decanted particles that are visible with the naked eye or under microscope). Under the same conditions, a highly cohesive gel shows substantially no phase separation, and the dye is prevented from diffusing into the cohesive formulation. A relatively less cohesive gel, on the other hand, shows a clear phase separation.

Example 2

Effect of Water Soluble Molecules on HA-Based Gel Formulation Extrudability

The active ingredient was incorporated into a HA-based gel matrix and autoclaved by steam sterilization at a temperature between about 130° C. to about 135° C. for between about one minute and about 10 minutes. The hydrogel properties, aspect (i.e., color/clarity/homogeneity), and extrusion force were analyzed after autoclaving and at 3 years equivalent at room temperature. All formulations were clear, homogenous, uncolored, and had acceptable extrusion force properties after autoclaving and at the 3-year equivalent mark (Table 3). These results show that the test gels exhibited no degradation, indicating that the gels were stable and incorporation of the ingredients had no impact on hydrogel properties and structure.

TABLE 3

| Ingredient | Concentration (%) | Aspect | Extrusion force (N) after autoclaving | Extrusion force (N) 3 years~room T ° C. |
|---|---|---|---|---|
| Allantoin | 0.3 | Clear | PASSED | PASSED |
|  | 0.5 | Homogeneous | PASSED | PASSED |
| Cytidine | 0.5 | Uncolored | PASSED | PASSED |
|  | 1 |  | PASSED | PASSED |
| Thymidine | 0.5 |  | PASSED | PASSED |
|  | 1 |  | PASSED | PASSED |
| Uridine | 0.5 |  | PASSED | PASSED |
|  | 1 |  | PASSED | PASSED |
| Antipyrin | 0.5 |  | PASSED | PASSED |
|  | 1 |  | PASSED | PASSED |
| Aminocaproic acid | 0.5 |  | PASSED | PASSED |
|  | 1 |  | PASSED | PASSED |
| Tranexamic acid | 0.5 |  | PASSED | PASSED |

TABLE 3-continued

| Ingredient | Concentration (%) | Aspect | Extrusion force (N) after autoclaving | Extrusion force (N) 3 years~room T ° C. |
|---|---|---|---|---|
| Eucalyptol | 0.5 | | PASSED | PASSED |
| Sodium selenite | 0.1 | | PASSED | PASSED |
| Glycerin | 0.5 | | PASSED | PASSED |

"PASSED" means that the change of extrusion force (ΔF) was less than two Newtons (<2 N). In other words the measured ΔF of the extrusion force of the HA gel with the specified ingredients minus the extrusion force of the HA gel without the added ingredients was <2 N

Example 3

Effect of Vitamin C Derivative on HA-Based Gel Formulation Extrudability and Stability Ascorbic acid, at a concentration of 1% (w/w), was, incorporated in a HA-based gel matrix, and the pH of the gel adjusted to about 7 and then autoclaved by steam sterilization at a temperature between about 130° C. to about 135° C. for between about one minute and about 10 minutes. Although clear and uncolored before autoclaving, the gel was clear but yellowed after autoclaving indicating that the test gel was degraded.

Example 4

Effect of Vitamin C Derivative on HA-Based Gel Formulation Extrudability and Stability Magnesium Ascorbyl Phosphate (MAP), at a concentration of 0.6% (w/w), 1% (w/w) or 2% (w/w), was incorporated in a HA-based gel matrix, and the pH of the gel adjusted to about 7 and then autoclaved as in Example 3. The gel was clear and uncolored both before and after autoclaving. Both extrusion force and degradation were used to access the rheological properties of a gel. Degradation was determined as a function of time using a controlled stress rheometer according to the following method: frequency sweep from 0.05 Hz to 10 Hz with 0.8% (w/w) controlled strain.

Δ Tan δ 1 Hz=(Tan δ 1 Hz test gel)−(Tan δ 1 Hz control gel) where Tan δ 1 Hz is the ratio of viscous modulus to elastic modulus. A Δ Tan δ 1 Hz of less than 0.1 demonstrates no detectable degradation, indicating that a test gel was stable. Rheology analysis showed that although the test gels has acceptable extrusion force properties, the test gels exhibited degradation after autoclaving indicating that the gel was unstable (Table 4).

TABLE 4

| | After Autoclaving | |
|---|---|---|
| Formulation | Extrusion force (N) | Δ Tan δ 1 Hz |
| HA gel + 0.6% (w/w) MAP | PASSED | ND |
| HA gel + 1% (w/w) MAP | PASSED | ND |
| HA gel + 2% (w/w) MAP | PASSED | 0.344 |

"PASSED": ΔF < 2 N
Stable if Δ Tan δ 1 Hz < 0.1
ND, not determined

Example 5

Effect of Vitamin C Derivative on HA-Based Gel Formulation Extrudability and Stability Sodium Ascorbyl Phosphate (SAP), at a concentration of 0.6% (w/w), 1% (w/w), or 2% (w/w), was incorporated in a HA-based gel matrix, and the pH of the gel adjusted to about 7 and then autoclaved as in Example 3. The gel was clear and uncolored both before and after autoclaving. Rheology analysis showed that the test gels had acceptable extrusion force properties, and that the test gels exhibited no degradation relative to controls indicating that the gels were stable (Table 5).

TABLE 5

| | After Autoclaving | |
|---|---|---|
| Formulation | Extrusion force (N) | Δ Tan δ 1 Hz |
| HA gel + 0.6% (w/w) SAP | PASSED | ND |
| HA gel + 1% (w/w) SAP | PASSED | ND |
| HA gel + 2% (w/w) SAP | PASSED | 0.089 |

"PASSED": ΔF < 2 N
Stable if Δ Tan δ 1 Hz < 0.1
ND, not determined

Example 6

Effect of Vitamin C Derivative on HA-Based Gel Formulation Extrudability and Stability Ascorbic acid 2-Glucoside (AA2G™), at a concentration of 0.6% (w/w), 1% (w/w), or 2% (w/w), was incorporated in a HA-based gel matrix, and the pH of the gel adjusted to about 7 and then autoclaved as in Example 3. The gel was clear and uncolored both before and after autoclaving. Rheology analysis showed that the test gels had acceptable extrusion force properties, and that the test gels exhibited no degradation relative to controls indicating that the gels were stable (Table 6). The degradation of the test gels decreased as the concentration of ascorbic acid 2-glucoside increased indicating that higher ascorbic acid 2-glucoside concentrations increased gel stability.

TABLE 6

| | After Autoclaving | |
|---|---|---|
| Formulation | Extrusion force (N) | Δ Tan δ 1 Hz |
| HA gel + 0.6% (w/w) AA-2G ™ | PASSED | −0.010 |
| HA gel + 1% (w/w) AA-2G ™ | PASSED | −0.014 |
| HA gel + 2% (w/w) AA-2G ™ | PASSED | −0.016 |

"PASSED": ΔF < 2 N
Stable if Δ Tan δ 1 Hz < 0.1

Example 7

Effect of Vitamin C Derivative on HA-Based Gel Formulation Long-Term Stability

The formulations prepared in Example 6 were tested for shelf-life at 45° C. for 32 days and compared to a HA-based gel matrix without any additives. After the test period, the gel was clear and uncolored. Surprisingly, rheology analysis showed that all test gels with ascorbic acid 2-glucoside (AA2G™) not only exhibited no degradation during the test period, but that these gels showed increased stability over time (compare Δ Tan δ 1 Hz values from Table 4 with Δ Tan δ 1 Hz values from Table 7).

TABLE 7

| Formulation | Δ Tan δ 1 Hz |
|---|---|
| HA gel + 0.6% (w/w) AA2G ™ | −0.050 |
| HA gel + 1% (w/w) AA2G ™ | −0.045 |
| HA gel + 2% (w/w) AA2G ™ | −0.059 |

"PASSED": ΔF < 2 N
Stable if Δ Tan δ 1 Hz < 0.1

Example 8

Effect of Vitamin E Derivative on HA-Based Gel Formulation Extrudability and Stability Tocopheryl Acetate, at a concentration of 0.5% (w/w) or 1.2% (w/w), was incorporated in a HA-based gel matrix and the gel was autoclaved as in Example 3. The gel was unclear and white after autoclaving.

Example 9

Effect of Vitamin E Derivative on HA-Based Gel Formulation Extrudability and Stability Sodium Tocopheryl Phosphate (STP), at a concentration of 0.4% (w/w) or 1.2% (w/w), was incorporated in a HA-based gel matrix and the gel was autoclaved as in Example 3. The gel was unclear and white after autoclaving.

Example 10

Effect of Vitamin E Derivative on HA-Based Gel Formulation Extrudability and Stability Polyoxyethanyl-α-tocopheryl sebacate 0.7% (w/w) was incorporated in a HA-based gel matrix and the gel was autoclaved as in Example 3. The gel was clear, but heterogeneous after autoclaving.

Example 11

Effect of Vitamin E Derivative on HA-Based Gel Formulation Extrudability and Stability Tocopherol polyethylene glycol 1000 succinate (TPGS) at a concentration of 1% (w/w), 3.5% (w/w), or 7% (w/w) was incorporated in a HA-based gel matrix and the gel was autoclaved as in Example 3. The gel was clear and uncolored both before and after autoclaving. Rheology analysis showed that the test gels had acceptable extrusion force properties, and that the test gels exhibited no degradation relative to controls indicating that the gels were stable (Table 8).

TABLE 8

| | After Autoclaving | |
|---|---|---|
| Formulation | Extrusion force (N) | Δ Tan δ 1 Hz |
| HA gel + 1% (w/w) TPGS | PASSED | 0.008 |
| HA gel + 3.5% (w/w) TPGS | PASSED | −0.007 |
| HA gel + 7% (w/w) TPGS | PASSED | −0.011 |

"PASSED": ΔF < 2 N
Stable if Δ Tan δ 1 Hz < 0.1

Example 12

Effect of Vitamin C Derivative, Vitamin E Derivative, and Anesthetic Agent on HA-Based Gel Formulation Extrudability and Stability Lidocaine, at a concentration of 0.3% (w/w), was incorporated in a HA-based gel matrix comprising either 0.6% (w/w) ascorbic acid 2-glucoside (AA2G™) or 0.6% (w/w) ascorbic acid 2-glucoside (AA2G™) and 1.5% (w/w) TPGS, and the gels were autoclaved as in Example 3. The gels were clear and uncolored both before and after autoclaving. Rheology analysis showed that the test gels had acceptable extrusion force properties, and that the test gels exhibited no degradation relative to controls indicating that the gels were stable (Table 9).

TABLE 9

| | After Autoclaving | |
|---|---|---|
| Formulation | Extrusion force (N) | Δ Tan δ 1 Hz |
| HA gel + 0.6% (w/w) AA2G ™ + 0.3% (w/w) Lidocaine | PASSED | 0.059 |
| HA gel + 0.6% (w/w) AA2G ™ + 1.5% (w/w) TPGS + 0.3% (w/w) Lidocaine | PASSED | 0.016 |

"PASSED": ΔF < 2 N
Stable if Δ Tan δ 1 Hz < 0.1

Example 13

Effect of Vitamin C Derivative, Vitamin E Derivative, and Anesthetic Agent on HA-Based Gel Formulation Long-Term Stability The formulations prepared in Example 12 were tested for shelf-life at 45° C. for 48 days and compared to a HA-based gel matrix without any additives. After the test period, the gel was clear and uncolored. Surprisingly, rheology analysis showed that the test gel comprising 0.3% (w/w) lidocaine and either 0.6% (w/w) ascorbic acid 2-glucoside (AA2G™) or 0.6% (w/w) ascorbic acid 2-glucoside (AA2G™) and 1.5% (w/w) TPGS not only exhibited no degradation during the test period. (Table 10),

TABLE 10

| Formulation | Δ Tan δ 1 Hz |
|---|---|
| HA gel + 0.6% (w/w) AA2G ™ + 0.3% (w/w) Lidocaine | 0.020 |
| HA gel + 0.6% (w/w) AA2G ™ + 1.5% (w/w) TPGS + 0.3% (w/w) Lidocaine | 0.007 |

Stable if Δ Tan δ 1 Hz < 0.1

Figure 3:
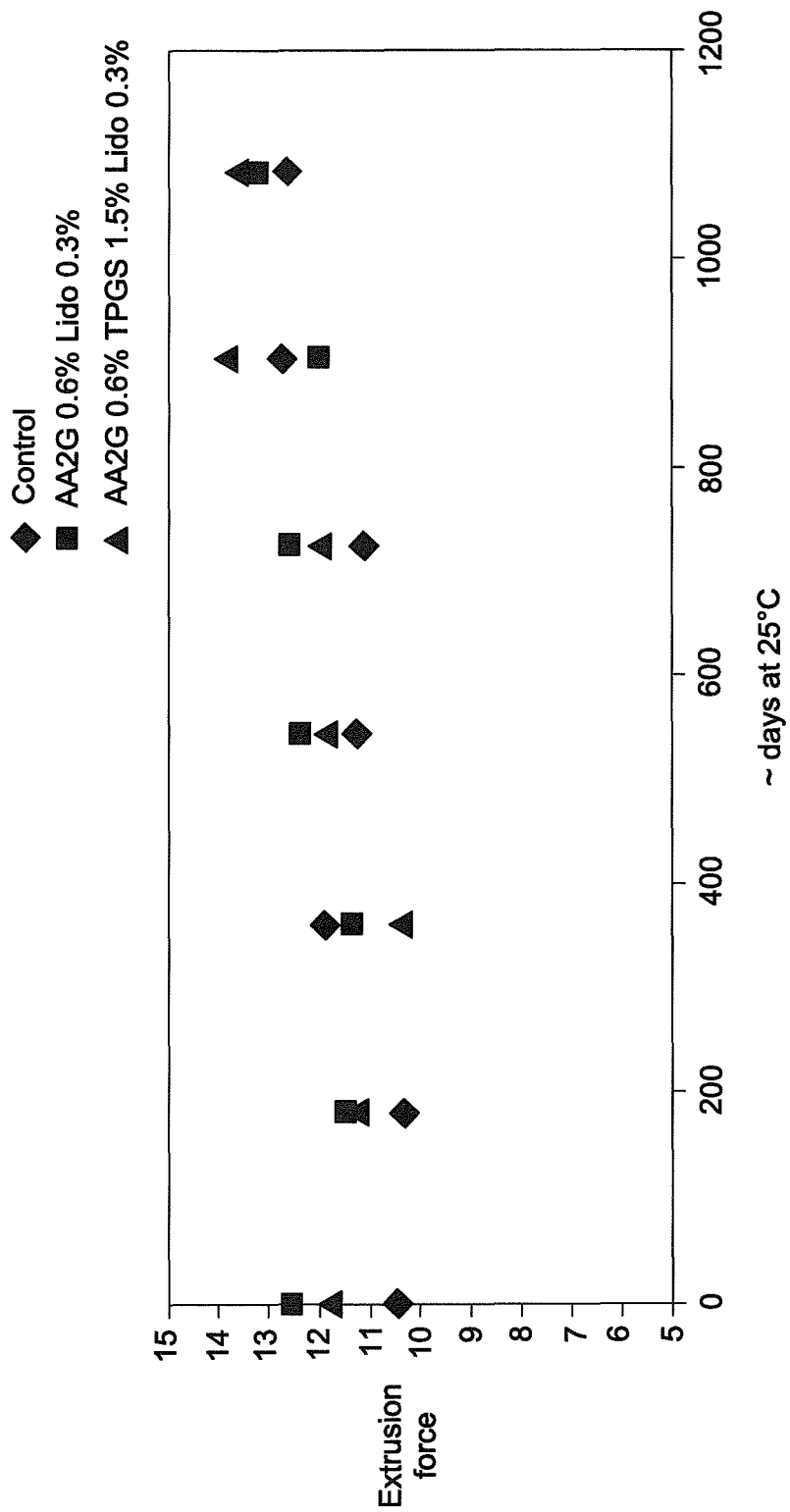
FIG. 3 is a graph showing the extrusion force over time (3 year equivalent at 25° C.) in compositions: control; a HA-based hydrogel with ascorbyl-2-glucoside (AA2G™) and lidocaine; and a HA-based hydrogel with ascorbyl-2-glucoside (AA2G™), lidocaine and TPGS.
Figure 4:
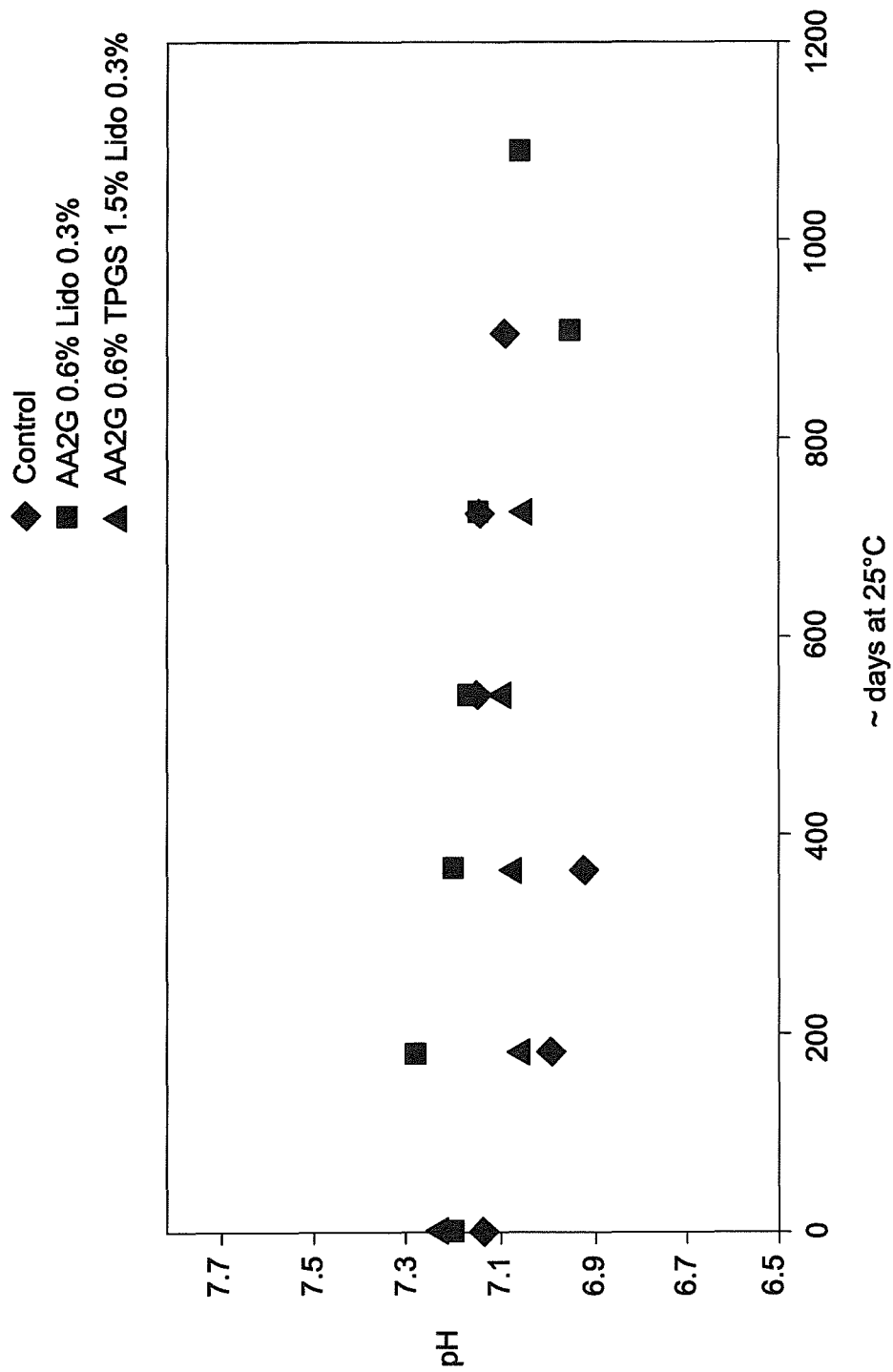
FIG. 4 is a graph showing the pH over time (3 year equivalent at 25° C.) in compositions: control; a HA-based hydrogel with ascorbyl-2-glucoside (AA2G™) and lidocaine; and a HA-based hydrogel with ascorbyl-2-glucoside (AA2G™) lidocaine and TPGS.
Figure 5:
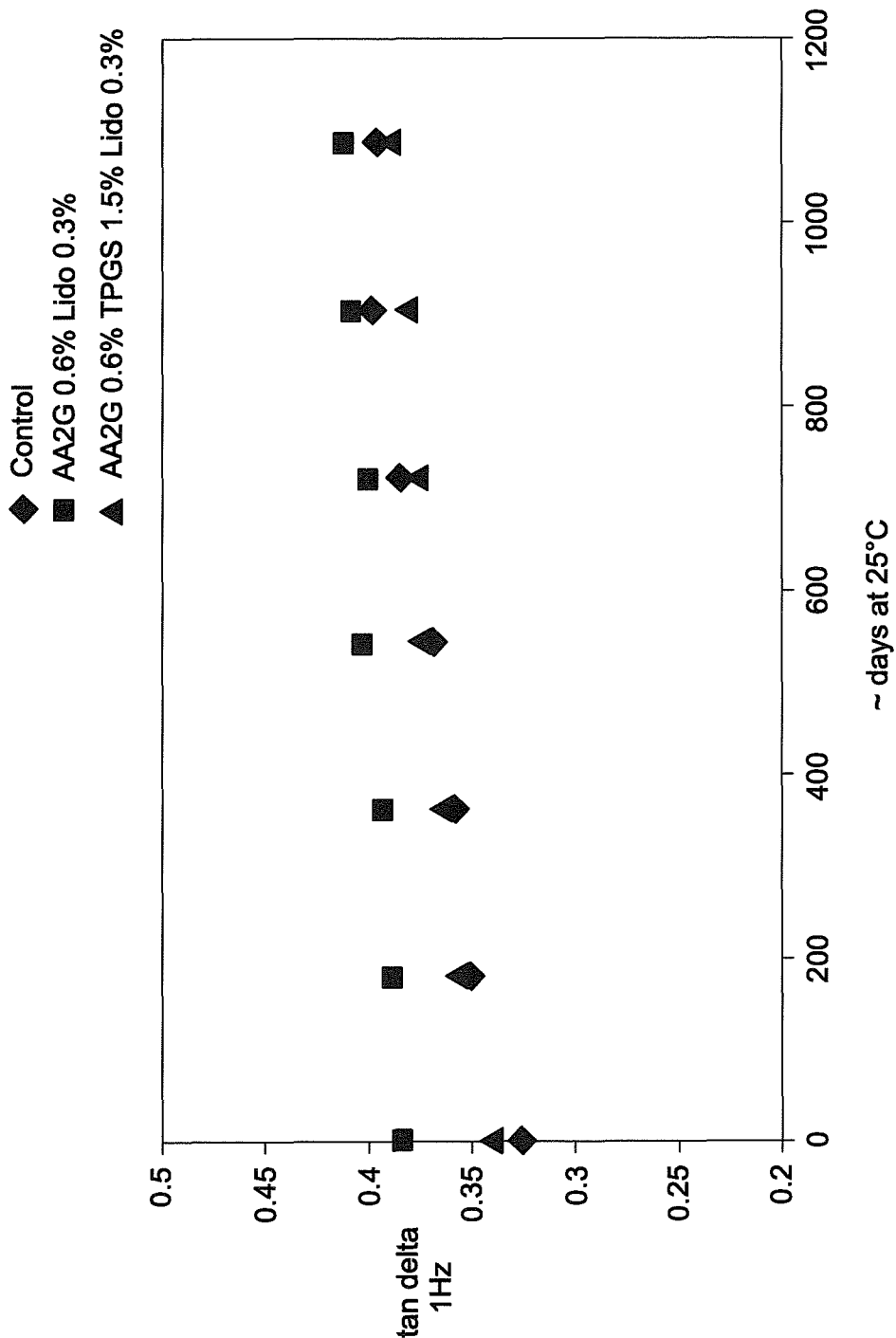
FIG. 5 is a graph of tan delta 1 Hz over time (3 yr equivalent at 25° C.) in compositions: control, a HA-based hydrogel with ascorbyl-2-glucoside (AA2G™); a HA-based hydrogel with ascorbyl-2-glucoside (AA2G™) and lidocaine; and a HA-based hydrogel with ascorbyl-2-glucoside (AA2G™), lidocaine and TPGS.
Figure 6:
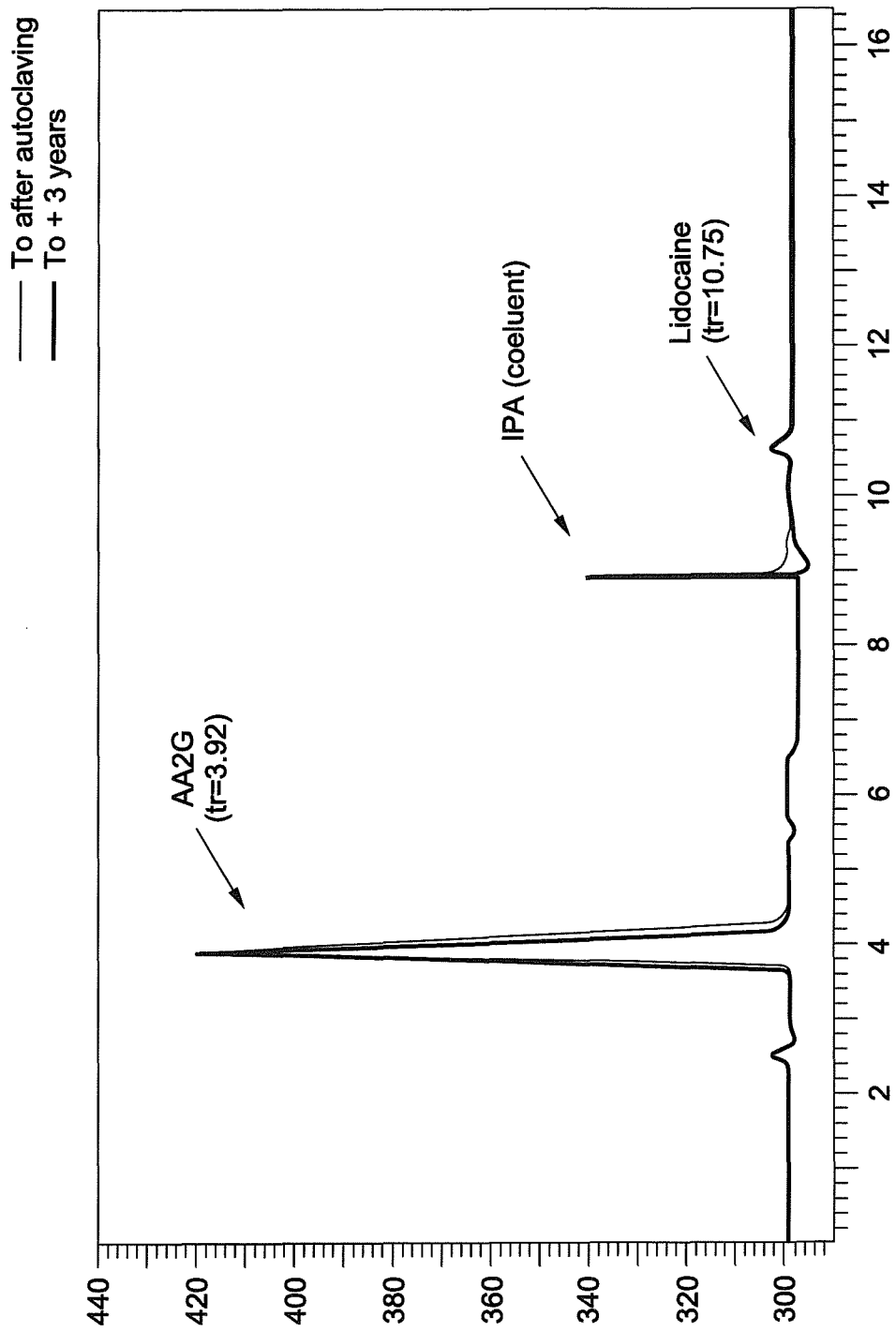
FIG. 6 is an HPLC analysis (C18 column, eluent: sodium phosphate buffer (pH=2.2)/2-propanol 10%, 0.7 ml/min; detection at 260 nm) of ascorbyl-2-glucoside (AA2G™), lidocaine, and IPA (coeluent) after autoclaving (3 year equivalent at 25° C.).

The stability of extrusion force, pH, and degradation are shown over time in FIGS. 3, 4, and 5, respectively. HPLC analysis (C18 column; eluent: sodium phosphate buffer (pH 2.2), 2-propanol 10%, 0.7 ml/min; detection at 260 nm) confirmed the ingredients after autoclaving and 3-year shelf-life are shown in FIG. 6.

Example 14

Vitamin C Derivative Promotes Collagen Synthesis

Figure 2:
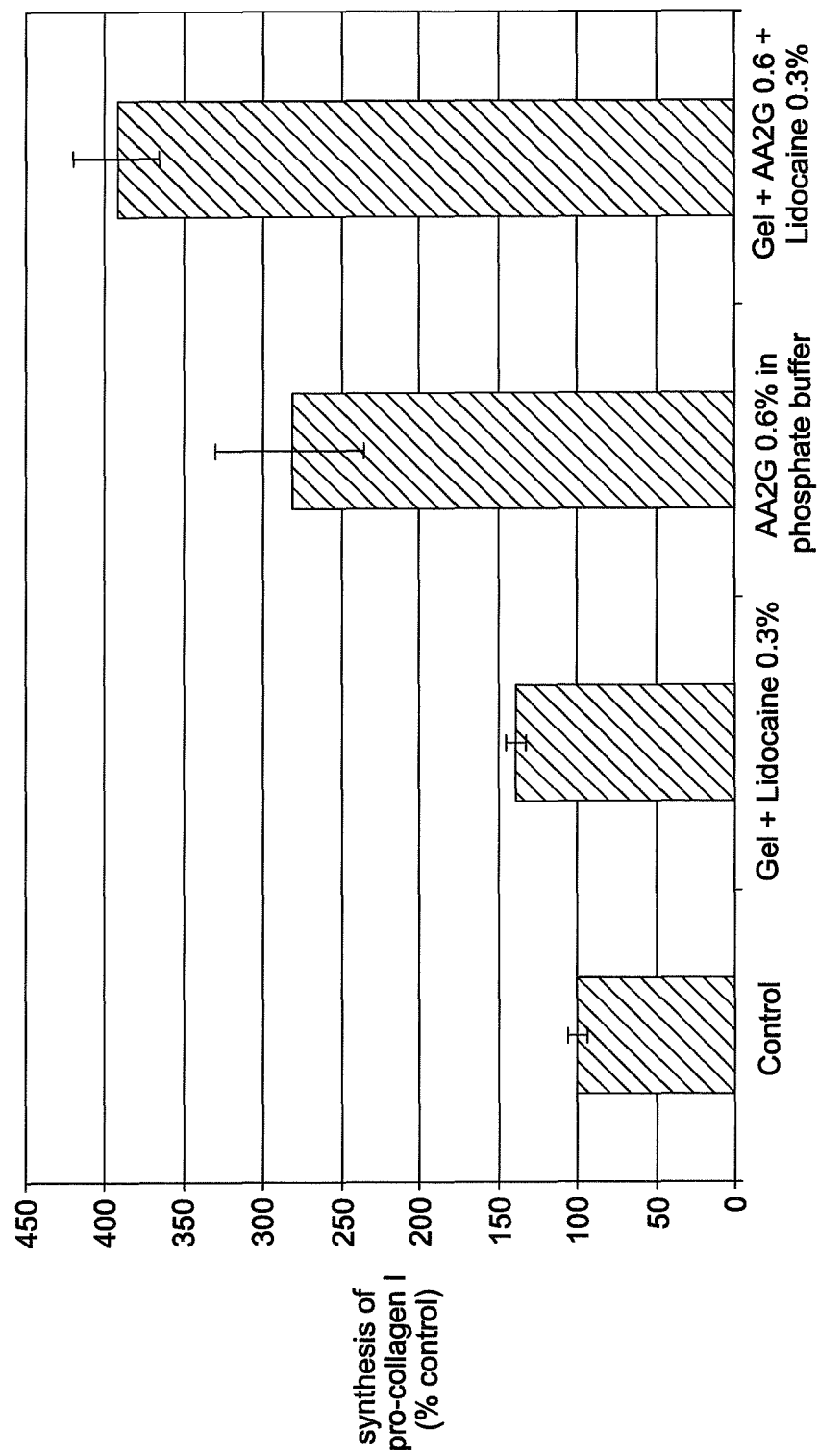
FIG. 2 is a graph showing the synthesis of pro-collagen (% control) for control; a HA-based hydrogel with 0.3% (w/w) lidocaine and 0.6% (w/w) ascorbyl-2-glucoside (AA2G™) in phosphate buffer; and a HA-based hydrogel with 0.6% (w/w) ascorbyl-2-glucoside (AA2G™) and 0.3% (w/w) lidocaine.

Human skin fibroblasts were cultured in a 12 wells plate. At confluence, 100 µL of each compound HA-based gel matrix w 0.3% (w/w) lidocaine; HA-based gel matrix with 0.3% (w/w) lidocaine and 0.6% (w/w) ascorbic acid 2-glucoside (AA2G™); and Phosphate Buffer with 0.6% (w/w) ascorbic acid 2-glucoside (AA2G™) was deposited in a culture insert (porosity of 0.4 µm), which was itself laid on the fibroblast monolayers. In parallel, a control without treatment was performed. Cultures were incubated for 72 hours and each experimental condition was conducted done in triplicate. At the end of incubation, cell viability was verified by microscopic observation and MTT reduction assay. Pro-collagen I secretion was measured using ELISA kit. The presence of 0.6% (w/w) ascorbic acid 2-glucoside (AA2G™) in a hyaluronic acid gel containing 0.3% (w/w) lidocaine increased pro-collagen synthesis by a factor 3 (+292%), whereas gel with 0.3% (w/w) lidocaine showed an increase of 40% of the pro-collagen secretion (see FIG. 2).

Example 15

Figure 7:
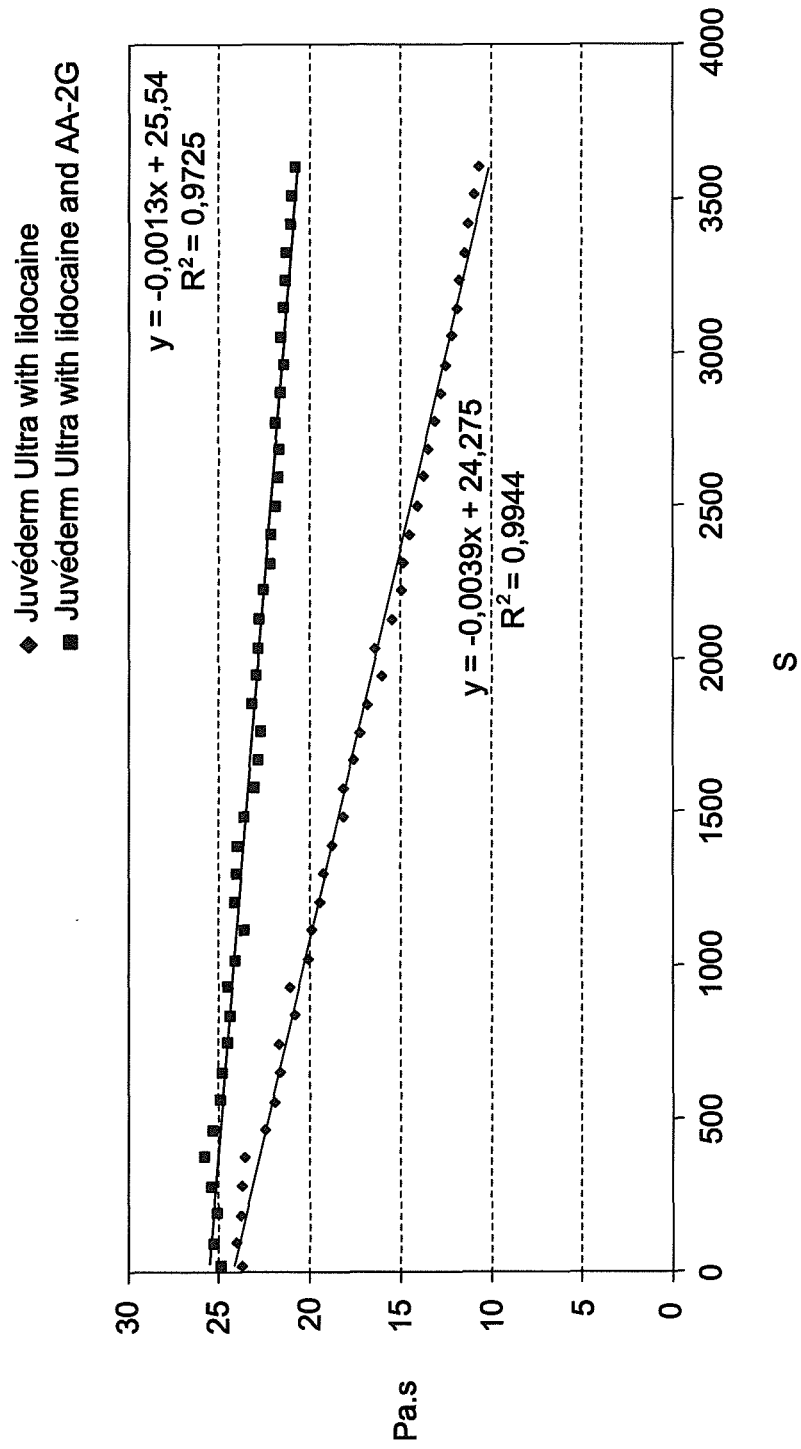
FIG. 7 is a graph comparing antioxidant properties in compositions: control versus JUVEDERM® Ultra with lidocaine, an ascorbyl-2-glucoside (AA2G™) and JUVEDERM® Ultra with lidocaine.

Vitamin C Derivative Protects HA-Based Gel Formulation from Oxidative Degradation The effect of ascorbic acid 2-glucoside (AA2G™) on HA-based gel matrix oxidative degradation was studied. Oxidation testing was used as it allows testing of the resistance of a HA-based gel matrix to free radicals. Degradation by free radicals was simulated on a rheometer (Haake Rheostress 600) by addition of 1/7 ratio of H2O2 30% on the surface of a spread gel measured with a controlled stress rheometer according to the following method: frequency of 1 Hz with 0.8% controlled strain, during 3600 s at 35° C. The time value is taken at 5 Pa/s. Further, a comparison of antioxidant properties for a HA-based gel matrix with 0.3% (w/w) lidocaine and 0.06% (w/w) ascorbic acid 2-glucoside (AA2G™) (15 800 s) versus a HA-based gel matrix with 0.3% (w/w) lidocaine (4 942 s) showed that the gel containing ascorbic acid 2-glucoside (AA2G™) and lidocaine is more stable with respect to free radical activity (FIG. 7). Ascorbic acid 2-glucoside (AA2G™) protected against oxidative degradation by a factor of 3.

Example 16

Implantation Study

A gel containing 0.6% (w/w) ascorbic acid 2-glucoside (AA2G™) was implanted in the deep dermis and subcutaneous tissues in rats. Histological evaluation at 1 week showed some mononuclear cells (lymphocytes and plasmocytes) around the implants in all implantation sites (test and control). They were also associated with macrophages. The gel containing ascorbic acid 2-glucoside (AA2G™) appeared to be less inflammatory. The irritation index in test samples (sodium HA with AA2G™) was 9.9 compared to 12.3 in controls (sodium HA only). Table 11 shows the histological results at 1 week, 1 month, and 3 months. The irritation scores of test gel for each implantation time are lower than control.

TABLE 11

| Biocompatibility ISO 10993 | Sodium HA + AA2G ™ + Lidocaine |
| --- | --- |
| Cytotoxicity | ✓ (non cytotoxic) |
| Irritation | ✓ (non irritant) |
| Sensitization | ✓ (non sensitizing) |
| Implantation Test | |
| One week | ✓ (no skin reaction) |
| Three weeks | ✓ (no skin reaction) |
| Three months | ✓ (no skin reaction) |

Example 17

Effect of Moisturizing Agent on HA-Based Gel Formulation Extrudability and Stability Dexpanthenol, at a concentration of 1% (w/w), was incorporated into a HA-based gel matrix comprising 0.3% (w/w) lidocaine and the gel was autoclaved as in Example 3. The gel was clear and uncolored both before and after autoclaving. Rheology analysis showed that the test gel had acceptable extrusion force properties, and that the test gel exhibited no degradation relative to controls indicating that the test gel was stable (Table 12).

TABLE 12

| | After Autoclaving | |
| --- | --- | --- |
| Formulation | Extrusion force (N) | Δ Tan δ 1 Hz |
| HA gel + 0.3% (w/w) Lidocaine + 1% (w/w) Dexpanthenol | PASSED | 0.026 |

"PASSED": ΔF < 2 N
Stable if Δ Tan δ 1 Hz < 0.1

Example 18

Effect of Moisturizing Agent on HA-Based Gel Formulation Long-Term Stability

The formulations prepared in Example 17 were tested for shelf-life at 45° C. for 30 days and compared to a HA-based gel matrix without any additives. After the test period, the gel was clear and uncolored. Surprisingly, rheology analysis showed that the test gel with dexpanthenol not only exhibited no degradation during the test period, but that this gel showed increased stability over time (compare Δ Tan δ1 Hz value from Table 12 with Δ Tan δ 1 Hz value from Table 13).

TABLE 13

| Formulation | Δ Tan δ 1 Hz |
| --- | --- |
| HA gel + 0.3% (w/w) Lidocaine (w/w) + 1% (w/w) Dexpanthenol | −0.071 |

Stable if Δ Tan δ 1 Hz < 0.1

Example 19

Effect of Vasoconstrictor Agent on HA-Based Gel Formulation Extrudability and Stability Epinephrine bitartrate, at a concentration of 10 ppm (1 ppm is approximately 0.1 mg/g), was incorporated into a HA-based gel matrix) and the gel was autoclaved as in Example 3. The gel obtained both before and after autoclaving was clear and uncolored. Rheology analysis showed that although the test gel comprising 10 ppm epinephrine bitartrate had acceptable extrusion force properties, the test gel exhibited degradation after autoclaving indicating that the gel was unstable (Table 14).

TABLE 14

|  | After Autoclaving | |
|---|---|---|
| Formulation | Extrusion force (N) | Δ Tan δ 1 Hz |
| HA gel + 10 ppm epinephrine bitartrate | PASSED | 0.165 |

"PASSED": ΔF < 2 N
Stable if Δ Tan δ 1 Hz < 0.1

Example 20

Effect of Vasoconstrictor Agent and Anesthetic Agent on HA-Based Gel Formulation Extrudability and Stability Epinephrine bitartrate, at a concentration of 10 ppm, was incorporated into a HA-based gel matrix comprising 0.3% (w/w) lidocaine and the gel was autoclaved as in Example 3. Although the gel obtained before autoclaving was clear and uncolored, the gel obtained after autoclaving was clear but colored. Rheology analysis showed that although the test gels has acceptable extrusion force properties (Table 15).

TABLE 15

|  | After Autoclaving | |
|---|---|---|
| Formulation | Extrusion force (N) | Δ Tan δ 1 Hz |
| HA gel + 0.3% (w/w) Lidocaine + 10 ppm epinephrine bitartrate | PASSED | 0.092 |

"PASSED": ΔF < 2 N
Stable if Δ Tan δ 1 Hz < 0.1

Example 21

Effect of Vasoconstrictor Agent and Anesthetic Agent on HA-Based Gel Formulation Long-Term Stability The formulations prepared in Example 20 were tested for shelf-life at 45° C. for 60 days and compared to a HA-based gel matrix without any additives. After the test period, the gel was clear and slightly colored. Rheology analysis showed that gels with 0.3% (w/w) lidocaine and 10 ppm epinephrine bitartrate exhibited degradation of the test gel during the test period indicating that the gel was unstable over time (compare Δ Tan δ 1 Hz value from Table 13 with Δ Tan δ 1 Hz value from Table 16).

TABLE 16

| Formulation | Δ Tan δ 1 Hz |
|---|---|
| HA gel + 0.3% (w/w) Lidocaine + 10 ppm epinephrine bitartrate | 0.185 |

"PASSED": ΔF < 2 N
Stable if Δ Tan δ 1 Hz < 0.1

Example 22

Effect of Vasoconstrictor Agent and Antioxidant on HA-Based Gel Formulation Extrudability and Stability Epinephrine, at a concentration of 10 ppm, was incorporated into a HA-based gel matrix comprising either 0.9 (w/w) or 4.5% (w/w) mannitol and the gel was autoclaved as in Example 3. The gel with 4.5% (w/w) mannitol was clear and uncolored before and after autoclaving whereas the gel with 0.9% (w/w) mannitol was slightly colored. Rheology analysis showed that the test gels with 0.3% (w/w) lidocaine, 10 ppm epinephrine bitartrate, and either 0.9 (w/w) or 4.5% (w/w) mannitol had acceptable extrusion force properties, and that the test gels exhibited no degradation relative to controls indicating that the gels were stable (Table 17).

TABLE 17

|  | After Autoclaving | |
|---|---|---|
| Formulation | Extrusion force (N) | Δ Tan δ 1 Hz |
| HA gel + 10 ppm epinephrine bitartrate + 0.9% (w/w) mannitol | PASSED | 0.047 |
| HA gel + 10 ppm epinephrine bitartrate + 4.5% (w/w) mannitol | PASSED | 0.015 |

"PASSED": ΔF < 2 N
Stable if Δ Tan δ 1 Hz < 0.1

Example 23

Effect of Vasoconstrictor Agent and Antioxidant on HA-Based Gel Formulation Long-Term Stability The formulations prepared in Example 22 were tested for shelf-life at 45° C. for 60 days and compared to a HA-based gel matrix without any additives. After the test period, the gel was clear and slightly colored. Rheology analysis showed that gels with 0.3% (w/w) lidocaine, 10 ppm epinephrine bitartrate, and either 0.9 (w/w) or 4.5% (w/w) mannitol exhibited no degradation during the test period indicating that the test gels were stable over time (Table 18). The gel with 4.5% (w/w) mannitol was more stable over time (compare Δ Tan δ1 Hz value from Table 17 with Δ Tan δ 1 Hz value from Table 18).

TABLE 18

| Formulation | Δ Tan δ 1 Hz |
|---|---|
| HA gel + 10 ppm epinephrine bitartrate + 0.9% (w/w) mannitol | 0.061 |
| HA gel + 10 ppm epinephrine bitartrate + 4.5% (w/w) mannitol | 0.006 |

Stable if Δ Tan δ 1 Hz < 0.1

Example 24

Effect of Vasoconstrictor Agent, Antioxidant, and Anesthetic Agent on HA-Based Gel Formulation Extrudability and Stability Epinephrine bitartrate, at a concentration of 20 ppm, was incorporated into a HA-based gel matrix comprising 0.3% (w/w) lidocaine and 4.5% (w/w) mannitol and the gel was autoclaved as in Example 3. The gel was clear and uncolored before autoclaving, but was slightly colored after autoclaving. Rheology analysis showed that the test gel with 20 ppm epinephrine bitartrate, 0.3% (w/w) lidocaine, and 4.5% (w/w) mannitol had acceptable extrusion force properties, and that the test gel exhibited no degradation relative to controls indicating that the gel was stable (Table 19)

TABLE 19

| | After Autoclaving | |
|---|---|---|
| Formulation | Extrusion force (N) | Δ Tan δ 1 Hz |
| HA gel + 20 ppm epinephrine bitartrate + 4.5% (w/w) mannitol + 0.3% (w/w) Lidocaine | PASSED | 0.026 |

"PASSED": ΔF < 2 N
Stable if Δ Tan δ 1 Hz < 0.1

Example 25

Effect of Vasoconstrictor Agent, Antioxidant, and Anesthetic Agent on HA-Based Gel Formulation Long-Term Stability The formulation prepared in Example 24 was tested for shelf-life at 45° C. for 60 days and compared to a HA-based gel matrix without any additives. After the test period, the gel was clear and slightly colored. Rheology analysis showed that the test gel with 20 ppm epinephrine bitartrate, 0.3% (w/w) lidocaine, and 4.5% (w/w) mannitol exhibited no degradation during the test period.

TABLE 20

| Formulation | Δ Tan δ 1 Hz |
|---|---|
| HA gel + 20 ppm epinephrine bitartrate + 4.5% (w/w) mannitol + 0.3% (w/w) Lidocaine | −0.030 |

Stable if Δ Tan δ 1 Hz < 0.1

Example 26

Effect of Vasoconstrictor Agent and Anesthetic Agent on HA-Based Gel Formulation Extrudability and Stability Synephrine, at a concentration of 100 ppm, was incorporated into a HA-based gel matrix comprising 0.3% (w/w) lidocaine and the gel was autoclaved as in Example 3. The gel was clear and uncolored both before and after autoclaving. Rheology analysis showed that the test gel with 100 ppm synephrine and 0.3% (w/w) lidocaine had acceptable extrusion force properties, and that the test gel exhibited no degradation relative to controls indicating that the gel was stable (Table 21)

TABLE 21

| | After Autoclaving | |
|---|---|---|
| Formulation | Extrusion force (N) | Δ Tan δ 1 Hz |
| HA gel + Lidocaine 0.3% + 100 ppm synephrine | PASSED | −0.006 |

"PASSED": ΔF < 2 N
Stable if Δ Tan δ 1 Hz < 0.1

Example 27

Effect of Vasoconstrictor Agent and Anesthetic Agent on HA-Based Gel Formulation Long-Term Stability The formulations prepared in Example 26 were tested for shelf-life at 45° C. for 60 days and compared to a HA-based gel matrix with 0.3% (w/w) lidocaine. After the test period, the gel was clear and uncolored. Rheology analysis showed that the test gel with 100 ppm synephrine and 0.3% (w/w) lidocaine exhibited no degradation during the test period.

TABLE 22

| Formulation | Δ Tan δ 1 Hz |
|---|---|
| HA gel + 0.3% (w/w) Lidocaine + 100 ppm synephrine | −0.028 |

Stable if Δ Tan δ 1 Hz < 0.1

Example 28

Effect of Vasoconstrictor Agent and Anesthetic Agent on HA-Based Gel Formulation Extrudability and Stability Over Autoclaving Phenylephrine, at a concentration of 100 ppm or 400 ppm, was incorporated into HA-based gel matrixes comprising 0.3% (w/w) lidocaine and the gel were autoclaved as in Example 3. The gels were clear and uncolored both before and after autoclaving. Rheology analysis showed that the tested gels with 100 ppm or 400 ppm phenylephrine and 0.3% (w/w) lidocaine had acceptable extrusion force properties, and that the tested gels exhibited no degradation relative to controls indicating that the gels were stable (Table 23)

TABLE 23

| | After Autoclaving | |
|---|---|---|
| Formulation | Extrusion force (N) | Δ Tan δ 1 Hz |
| HA gel + Lidocaine 0.3% + 100 ppm Phenylephrine | PASSED | −0.002 |
| HA gel + Lidocaine 0.3% + 400 ppm Phenylephrine | PASSED | 0.061 |

"PASSED": ΔF < 2 N
Stable if Δ Tan δ 1 Hz < 0.1

Example 28A

Biocompatibility of Formulations with Phenylephrine

The formulations prepared in Example 28 were submitted to the 4 basic tests required by the ISO 10993 norm to test the biocompatibility of implantable medical devices. It comprises a cytotoxicity test (cellular assay), an irritation test (skin observation in animal), a sensitization test (animal test for allergic reactions) and an acute/systemic toxicity test (intra-peritoneal injection in an animal). Both formulations passed all four tests with no significant differences when compared to similar formulations without phenylephrine.

TABLE 23A

| Biocompatibility ISO 10993 | HA gel + 0.3% Lidocaine + 100 ppm or 400 ppm Phenylephrine |
|---|---|
| Cytotoxicity | ✓ (non cytotoxic) |
| Irritation | ✓ (non irritant) |
| Sensitization | ✓ (non sensitizing) |
| Acute toxicity | ✓ (no acute toxicity) |

Example 29

Effect of Vasoconstrictor Agent and Anesthetic Agent on HA-Based Gel Formulation Long-Term Stability The formulations prepared in Example 28 were tested for shelf-life at 45° C. for 60 days and compared to a HA-based gel matrix with 0.3% (w/w) lidocaine. After the test period, the gels were clear and uncolored. Rheology analysis showed that the tested gels with 100 ppm or 400 ppm phenylephrine and 0.3% (w/w) lidocaine exhibited no degradation during the test period.

TABLE 24

| Formulation | Δ Tan δ 1 Hz |
|---|---|
| HA gel + 0.3% (w/w) Lidocaine + 100 ppm Phenylephrine | −0.017 |
| HA gel + 0.3% (w/w) Lidocaine + 400 ppm Phenylephrine | 0.025 |

Stable if Δ Tan δ 1 Hz < 0.1

Example 30

Effect of Vasoconstrictor Agent and Anesthetic Agent on HA-Based Gel Formulation Extrudability and Stability Naphazoline, at a concentration of 100 ppm, was incorporated into a HA-based gel matrix comprising 0.3% (w/w) lidocaine and the gel was autoclaved as in Example 3. The gel was clear and uncolored both before and after autoclaving. Rheology analysis showed that the test gel with 100 ppm naphazoline and 0.3% (w/w) lidocaine had acceptable extrusion force properties, and that the test gel exhibited no degradation relative to controls indicating that the gel was stable (Table 25)

TABLE 25

| | After Autoclaving | |
|---|---|---|
| Formulation | Extrusion force (N) | Δ Tan δ 1 Hz |
| HA gel + Lidocaine 0.3% + 100 ppm Naphazoline | PASSED | −0.003 |

"PASSED": ΔF < 2 N
Stable if Δ Tan δ 1 Hz < 0.1

Example 31

Effect of Vasoconstrictor Agent and Anesthetic Agent on HA-Based Gel Formulation Long-Term Stability The formulations prepared in Example 30 were tested for shelf-life at 45° C. for 60 days and compared to a HA-based gel matrix with 0.3% (w/w) lidocaine. After the test period, the gel was clear and uncolored. Rheology analysis showed that the test gel with 100 ppm naphazoline and 0.3% (w/w) lidocaine exhibited no degradation during the test period.

TABLE 26

| Formulation | Δ Tan δ 1 Hz |
|---|---|
| HA gel + 0.3% (w/w) Lidocaine + 100 ppm Naphazoline | −0.008 |

Stable if Δ Tan δ 1 Hz < 0.1

Example 32

Effect of Antihemorrhagic Agent and Anesthetic Agenton HA-Based Gel Formulation Extrudability and Stability Tranexamic acid, at a concentration of 0.4% (w/w), was incorporated into a HA-based gel matrix comprising 0.3% (w/w) lidocaine and the gel was autoclaved as in Example 3. The gel was clear and uncolored both before and after autoclaving. Rheology analysis showed that the test gel with 0.4% (w/w) tranexamic acid and 0.3% (w/w) lidocaine had acceptable extrusion force properties, and that the test gel exhibited no degradation relative to controls indicating that the gel was stable (Table 27)

TABLE 27

| | After Autoclaving | |
|---|---|---|
| Formulation | Extrusion force (N) | Δ Tan δ 1 Hz |
| HA gel + 0.3% (w/w) Lidocaine + 0.4% (w/w) Tranexamic acid | PASSED | 0.003 |

"PASSED": ΔF < 2 N
Stable if Δ Tan δ 1 Hz < 0.1

Example 33

Effect of Antihemorrhagic Agent and Anesthetic Agenton HA-Based Gel Formulation Long-Term Stability The formulations prepared in Example 32 were tested for shelf-life at 45° C. for 60 days and compared to a HA-based gel matrix with 0.3% (w/w) lidocaine. After the test period, the gel was clear and uncolored. Rheology analysis showed that the gel is stable during the test period.

TABLE 28

| Formulation | Δ Tan δ 1 Hz |
|---|---|
| HA gel + 0.3% (w/w) Lidocaine + 0.4% (w/w) Tranexamic acid | 0.053 |

Stable if Δ Tan δ 1 Hz < 0.1

Example 34

Use of Dermal Filler Composition for Treating Wrinkles

This example illustrates the use of compositions and methods disclosed herein for treating wrinkles.

A 37-year-old woman presents with fine lines around her eyes and deeper wrinkles on the sides of her mouth. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g. one of the compositions of Examples 11, 12, 17, 22, 14, 26, 28, 30 and 32, is administered subcutaneously and under superficial musculature of the affected regions once a week for three weeks; about 1.0 mL to about 2.0 mL of composition into the affected cheek region. The individual is then monitored for approximately 7 days. The physician evaluates the facial regions and determines that the treatment was successful. Both the woman and her physician are satisfied with the results of the procedure because she looked younger. Approximately one month after the procedure, the woman indicates that his quality of life has improved.

Example 35

Use of Dermal Filler Composition for Treating Wrinkles

This example illustrates the use of compositions and methods disclosed herein for treating a wrinkles.

A 59-year-old man presents with wrinkles between his eyebrows and in the nasolabial folds. Pre-operative evaluation of the person includes routine history and physical examination in addition to thorough informed consent disclosing all relevant risks and benefits of the procedure. The physician evaluating the individual determines that he is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the affected regions once every 3 months; about 1.5 mL to about 3.0 mL of composition into each affected region. The individual is then monitored for approximately 7 days. The physician evaluates the facial regions and determines that the treatment was successful. Both the man and his physician are satisfied with the results of the procedure because he looked younger. Approximately one month after the procedure, the man indicates that his quality of life has improved.

Example 36

Use of Dermal Filler Composition for Treating Wrinkles

This example illustrates the use of compositions and methods disclosed herein for treating wrinkles.

A 35-year-old woman presents with fine lines across her forehead. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the affected regions once a week for two weeks; about 1.0 mL to about 2.0 mL of composition into the affected cheek region. The individual is then monitored for approximately 7 days. The physician evaluates the facial regions and determines that the treatment was successful. Both the woman and her physician are satisfied with the results of the procedure because she looked younger. Approximately one month after the procedure, the woman indicates that his quality of life has improved.

Example 37

Use of Dermal Filler Composition for Treating Wrinkles

This example illustrates the use of compositions and methods disclosed herein for treating wrinkles.

A 44-year-old woman presents with uneven texture on her right cheek resulting from a loss of collagen due to aging. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the affected regions once a week for three weeks; about 3.0 mL to about 4.0 mL of composition into the affected cheek region. The individual is then monitored for approximately 7 days. The physician evaluates the facial regions and determines that the treatment was successful. Both the woman and her physician are satisfied with the results of the procedure because she looked younger. Approximately one month after the procedure, the woman indicates that his quality of life has improved.

Example 38

Use of Dermal Filler Composition for Treating Wrinkles

This example illustrates the use of compositions and methods disclosed herein for treating wrinkles.

A 62-year-old woman presents with wrinkles across her forehead, on the sides of her eyes, and in the nasolabial folds. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the affected regions; about 1.5 mL to about 2.5 mL of composition into each affected region. The individual is then monitored for approximately 7 days. The physician evaluates the facial regions and determines that the treatment was successful. Both the woman and her physician are satisfied with the results of the procedure because she looked younger. Approximately one month after the procedure, the woman indicates that his quality of life has improved.

Example 39

Use of Dermal Filler Composition for Treating a Scar

This example illustrates the use of compositions and methods disclosed herein for treating a scar.

A 35-year-old man presents with a deep scar across his chin. Pre-operative evaluation of the person includes routine history and physical examination in addition to thorough informed consent disclosing all relevant risks and benefits of the procedure. The physician evaluating the individual determines that he is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the affected regions; about 1.0 mL to about 2.0 mL of composition into the affected region. The individual is then monitored for approximately 7 days. The physician evaluates the facial regions and determines that the treatment was successful. Both the man and his physician are satisfied with the results of the procedure because he looked younger. Approximately one month after the procedure, the man indicates that his quality of life has improved.

Example 40

Use of Dermal Filler Composition for Treating a Facial Defect of the Cheek

This example illustrates the use of compositions and methods disclosed herein for treating a facial defect of the cheek.

A 28-year-old woman presents with a lean face. She felt her face looked old, sad and bitter because of the less fullness of her cheek contour. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the cheeks regions; about 15 mL of composition into the left and right cheeks. The individual is then monitored for approximately 7 days. The physician evaluates the cheeks tissue and determines that the treatment was successful. Both the woman and her physician are satisfied with the results of the procedure because she looked younger. Approximately one month after the procedure, the woman indicates that his quality of life has improved.

Example 41

Use of Dermal Filler Composition for Treating Facial Imperfection of Eyelids

This example illustrates the use of compositions and methods disclosed herein for treating a facial imperfection of the eyelids.

A 37-year-old woman presents with sunken eyes and this appearance made her look old and fierce. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the upper eyelid regions; about 2.5 mL of composition into the left and right eyelid regions. The individual is then monitored for approximately 7 days. The physician evaluates the eyelid regions and determines that the treatment was successful. Both the woman and her physician are satisfied with the results of the procedure because she looked younger. Approximately one month after the procedure, the woman indicates that his quality of life has improved.

Example 42

Use of Dermal Filler Composition for Treating Wrinkles

This example illustrates the use of compositions and methods disclosed herein for treating wrinkles.

A 55-year-old woman presents with wrinkles around the eyes and cheek areas. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously and under superficial musculature of the upper eyelid and cheek regions; about 1.5 mL of composition into the left and right eyelid and cheek regions. The individual is then monitored for approximately 7 days. The physician evaluates the facial regions and determines that the treatment was successful. Both the woman and her physician are satisfied with the results of the procedure because she looked younger. Approximately one month after the procedure, the woman indicates that his quality of life has improved.

Example 43

Use of Dermal Filler Composition for Treating a Breast Defect

This example illustrates the use of compositions and methods disclosed herein for treating a breast defect.

A 32-year-old woman presents with complaints that the medial portions of her breast implants are visible, which accentuated the "bony" appearance of her sternum. In addition she felt her breast are too far apart. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously over the lateral sternum and medial breast bilaterally, 15 mL on the right and 10 mL on the left. The composition is administered in a tear like fashion to increase the surface area to volume ratio. The individual is then monitored for approximately 7 days. The physician evaluates the breasts and determines that the treatment was successful. Both the woman and her physician are satisfied with the results of the procedure. Approximately one month after the procedure, the woman indicates that his quality of life has improved.

Example 44

Use of Dermal Filler Composition for Breast Augmentation

This example illustrates the use of compositions and methods disclosed herein for breast augmentation.

A 28-year-old woman presents micromastia or breast hypoplasia. Pre-operative evaluation of the person includes routine history and physical examination in addition to thorough informed consent disclosing all relevant risks and benefits of the procedure. The physician evaluating the individual determines that she is a candidate for soft tissue treatment using the compositions and methods disclosed herein. A hydrogel composition as disclosed herein, such as, e.g., the compositions of Examples 11, 12, 17, 22, 24, 26, 28, 30, and 32, is administered subcutaneously using axillary, periareolar, and inframammary routes bilaterally, 90 mL on the right and 145 mL on the left. The composition is administered in a tear like fashion to increase the surface area to volume ratio. The individual is then monitored for approximately 7 days. The physician evaluates the breasts and determines that the treatment was successful. Both the woman and her physician are satisfied with the results of the procedure. Approximately one month after the procedure, the woman indicates that his quality of life has improved.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, those skilled in the art could make numerous and various modifications or changes to or alternative configurations of the disclosed subject matter can be made in accordance with the teachings herein without departing from the spirit of the present specification. Changes in detail may be made without departing from the spirit of the invention as defined in the appended claims. Lastly, the terminology used herein is for the purpose of describing particular embodiments only, and is not intended to limit the scope of the present invention, which is defined solely by the claims. In addition, it is intended that all matter contained in the above description or shown in the accompanying drawings shall be interpreted as illustrative only and not limiting. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

What is claimed is:

1. A dermal filler composition comprising a crosslinked hyaluronic acid-based polymer, oxymetazoline, and an ascorbic acid agent selected from ascorbic acid 2-glucoside, magnesium ascorbyl phosphate, sodium ascorbyl phosphate and L-ascorbic acid, 2-(3-aminopropyl hydrogen phosphate.

2. The composition of claim 1 which has been sterilized by heat treatment, pressure treatment, or both.

3. The composition of claim 2, wherein the heat treatment comprises heating to at least 100° C.

4. The composition of claim 3 which is substantially stable at room temperature for at least about 3 months, at least about 12 months, at least about 24 months or at least about 36 months.

5. The composition of claim 1, further comprising an anesthetic agent.

6. The composition of claim 5, wherein the anesthetic agent is lidocaine.

7. The composition of claim 6, wherein the lidocaine is present in an amount of between about 0.1% w/w and about 1.0% w/w.

8. The composition of claim 7, wherein the lidocaine is present in an amount of about 0.3% w/w.

9. The composition of claim 1, wherein the oxymetazoline is present in an amount of between about 0.01% w/w and about 0.1% w/w.

10. The composition of claim 1, wherein the ascorbic acid agent is ascorbic acid 2-glucoside.

11. The composition of claim 1, wherein the ascorbic acid agent is present in an amount of about 0.01% (w/w) to about 5% (w/w).

12. The composition of claim 1, wherein the hyaluronic acid-based polymer is crosslinked with 1,4-butanediol diglycidyl ether.

13. The composition of claim 1, wherein the hyaluronic acid-based polymer is present at a concentration of about 5 mg/g to about 40 mg/g.

14. The composition of claim 1, wherein the hyaluronic acid-based polymer has a mean molecular weight of about 300,000 Da to about 800,000 Da, or about 2,000,000 Da to about 5,000,000 Da.

15. The composition of claim 1, wherein the hyaluronic acid-based polymer comprises both high molecular weight hyaluronan and low molecular weight hyaluronan, wherein the high molecular weight hyaluronan has a molecular weight of greater than 2,000,000 Da and wherein the low molecular weight hyaluronan has a molecular weight of less than 1,000,000 Da.

16. A method for treating a skin condition, the method comprising injecting a dermal filler composition according to claim 1 into a dermal region of a subject in need thereof, thereby improving the skin condition.

17. The method of claim 16, wherein the skin condition is wrinkles.

18. The composition of claim 1, wherein the ascorbic acid agent is magnesium ascorbyl phosphate.

19. The composition of claim 1, wherein the ascorbic acid agent is sodium ascorbyl phosphate.

20. The composition of claim 1, wherein the ascorbic acid agent is L-ascorbic acid, 2-(3-aminopropyl hydrogen phosphate.

* * * * *